US008470965B2

(12) United States Patent
Schmidt et al.

(10) Patent No.: US 8,470,965 B2
(45) Date of Patent: Jun. 25, 2013

(54) METHODS AND COMPOSITIONS RELATED TO CYCLIC PEPTIDE SYNTHESIS

(75) Inventors: Eric W. Schmidt, Salt Lake City, UT (US); Brian Hathaway, Salt Lake City, UT (US); James T. Nelson, South Euclid, OH (US); Mohamed S. Donia, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 549 days.

(21) Appl. No.: 12/426,652

(22) Filed: Apr. 20, 2009

(65) Prior Publication Data
US 2010/0209414 A1 Aug. 19, 2010

Related U.S. Application Data

(63) Continuation-in-part of application No. 12/281,373, filed as application No. PCT/US2007/063089 on Mar. 1, 2007.

(60) Provisional application No. 60/777,954, filed on Mar. 1, 2006.

(51) Int. Cl.
C07K 14/00 (2006.01)

(52) U.S. Cl.
USPC ............................................ 530/324; 530/300

(58) Field of Classification Search
USPC .................................. 530/300, 324
See application file for complete search history.

(56) References Cited

U.S. PATENT DOCUMENTS

| | | | |
|---|---|---|---|
| 3,610,795 A | 10/1971 | Antoine | |
| 4,342,566 A | 8/1982 | Theofilopoulos | |
| 4,816,567 A | 3/1989 | Cabilly | |
| 4,868,116 A | 9/1989 | Morgan | |
| 4,897,355 A | 1/1990 | Epstein | |
| 4,980,286 A | 12/1990 | Morgan | |
| 5,556,768 A | 9/1996 | Yamashita | |
| 5,565,332 A | 10/1996 | Hoogenboom | |
| 5,596,079 A | 1/1997 | Smith | |
| 5,721,367 A | 2/1998 | Kay | |
| 5,804,440 A | 9/1998 | Burton | |
| 5,824,520 A | 10/1998 | Mulligan-Kehoe | |
| 5,837,243 A | 11/1998 | Deo | |
| 5,939,598 A | 8/1999 | Kuchrlpati | |
| 6,031,071 A | 2/2000 | Mandeville | |
| 6,096,441 A | 8/2000 | Hauser | |
| 6,130,364 A | 10/2000 | Jakobovits | |
| 6,180,377 B1 | 1/2001 | Morgan | |
| 6,261,834 B1 | 7/2001 | Srivastava | |
| 2004/0014100 A1 | 1/2004 | Lorenz et al. | |
| 2005/0260626 A1 | 11/2005 | Lorens et al. | |
| 2005/0266399 A1* | 12/2005 | Berndt et al. | ............ 435/5 |

FOREIGN PATENT DOCUMENTS

| | | |
|---|---|---|
| CA | 2345407 | 4/2000 |
| WO | WO89/07136 | 8/1989 |
| WO | WO90/02806 | 3/1990 |
| WO | WO92/03566 | 3/1992 |
| WO | WO93/22434 | 11/1993 |
| WO | WO94/29348 | 6/1994 |
| WO | WO94/19478 | 9/1994 |
| WO | WO95/24489 | 3/1995 |

OTHER PUBLICATIONS

Abel-Santos E, Scott CP, Benkovic SJ, Use of inteins for the in vivo production of stable cyclic peptide libraries in E. coli, Methods Mol Biol. 205:281-94 (2003).
Baggiohni M, et al., Interleukin-8, a chemotactic and inflammatory cytokine. FEBS Lett 307 97-101, (1992).
Banker, R., and S. Carmeli, Tenuecyclamides A-D, cyclic hexapeptides from the cyanobacterium Nostoc spongiaforme var. tenue, J. Nat. Prod. 61:1248-1251 (1998).
Baumann, Biology bacteriocyte-associated endosymbionts of plant sap-sucking insects, p. Annu Rev Microbiol 59:155-189 (2005).
Biard, J.F., C. Grivois, J.F. Verbist, C. Debitus & J.B. Cane, Origin of bistramide A identified in Lissoclinum bistratum (Urochordata): possible involvement of symbiotic Prochlorophyta. J. Mar. Biol. Ass. U. K. 70:741-746 (1990).
Blunt, J. W., B. R. Copp, M. H. G. Munro, P. T. Northcote, and M. R. Prinsep. Marine natural products. Nat. Prod. Rep. 23:26-78 (2006).
Bourne GT, Nielson JL, Coughlan JF, Darwen P, Campitelli MR, Horton DA, Rhumann A, Love SG, Tran TT, Smythe MLA convenient method for synthesis of cyclic peptide libraries, Methods Mol Biol. 298:151-65 (2005).
Bout, Lung Gene Therapy: In Vivo Adenovirus-Mediated Gene Transfer to Rhesus Monkey Airway Epithelium, Human Gene Therapy 5:3-10 (1994).
Carmichael, W. W., Cyanobacteria secondary metabolites—the cyanotoxins. J Appl Bacteriol. 72(6):445-59 (1992).
Carroll, A.R. et al., Patellins 1-6 and Trunkamide A: Novel Cyclic Hexa-, Hepta-and Octa-peptides from Colonial Ascidians, Lissoclinum sp., Aust. J. Chem, 49(6):659-667 (1996).
Choate KA, Kinsella TM, Wiliams ML, Nolan GP, Khavari PA. Transglutaminase 1 delivery to lamellar ichthyosis keratinocytes. Hum. Gene Ther 7:2247-53. (1996).
Cohen BA, Colas P, Brent R, An artificial cell-cycle inhibitor isolated from a combinatorial library, PNAS 1Proc Natl Acad Sci USA 95(24) 14272-7 (1998).
Davidson, B. S., Ascidians: producers of amino acid derived metabolites, Chem. Rev. 93, 1771-1791 (1993).
Davies et al., The cyclization of peptides and depsipeptides, J Peptide Sci 9(8):471-501 (2003).
Degnan, B. M., Hawkins, C. J., Lavin, M. F., McCaffrey, E. J., Parry, D. L., van den Brenk, A. L. & Watters, D. J. (1989. ) J. Med. Chem. 32, 1349-1354.
Devassy, V. P., P. M. Bhattathiri, and S. Z. Qasim. Succession of organisms following Trichodesmium phenomenon. Indian J. Mar. Sci. 8:88-93 (1979).
Donia M, Hathaway BJ, Sudek S, Haygood MG, Rosovitz MJ, Ravel J, Schmidt EW Natural combinatorial peptide libraries in cyanobacterial symbionts of marine ascidians, N at. Chem. Biol. 2:729-735 (2006).

(Continued)

Primary Examiner — David Lukton
(74) Attorney, Agent, or Firm — Ballard Spahr LLP

(57) ABSTRACT

Disclosed are compositions and methods for prenylation of polymers such as peptides.

7 Claims, 19 Drawing Sheets

OTHER PUBLICATIONS

Faulkner, D.J.; He, H.; Unson, M.D.; Bewley, C.A.; Garson, M.J. New metabolites from marine sponges: Are symbionts important? Gazz. Chim. Ital. 123, 301-307 (1993).

Feigner et al., Lipofection: A highly efficient, lipid-mediated DNA-transfection procedure. Proc Natl Acad Set USA 84 '413-7 '417 (1987).

Floss, Combinatorial biosynthesis—Potential and problems. Journal of Biotechnology 124 (2006) 242-257 (2006).

Fu, X., T. Do, F. J. Schmitz, V. Andrusevich, and M. H. Engel. 1998. New cyclic peptide from the ascidian *Lissoclinum patella*, J. Nat. Prod. 61:1547-1551 (1998).

Fuller, J. D., Camus, A. C., Duncan, C. L., Nizet, V., Bast, D. J., Thune, R. L., Low, D. E., de Azavedo, J. C. S., Identification of a Streptolysin S-Associated Gene Cluster and Its Role in the Pathogenesis of *Streptococcus iniae* Disease. Infect. Immun. 70:5730-5739 (2002).

Gehring, I. Mori, R. Perry, C. Walsh, The Nonribosomal Peptide Synthetase HMWP2 Forms a Thiazoline Ring During Biogenesis of Yersiniabactin, an Iron Chelating Virulence Factor of *Y. pestis*, Biochemistry 37:11637-11650 (1998).

Gerwick, W. H., L. T. Tan, and N. Sitachitta, Nitrogen-containing metabolites from marine cyanobacteria. Alkaloids Chem. Biol. 57:75-184, (2001).

Gonzalez-Pastor, J. E., San Millan, J. L., Castilla, M. A. & Moreno, F. Structure and Organization of Plasmid Genes Required to Produce the Translation Inhibitor Microcin. Journal of Bacteriology, p. 7131-7140 (Dec. 1995).

Guo C, P A, Tester Toxic effect of the bloom-forming *Tnchodesmium* sp (Cyanophyta) to the copepod *Acartia tonsa*, Nat Toxins 2 222-227 (1994).

Hahn J., Selective interaction between nonribosomal peptide synthetases is facilitated by short communication-mediating domains Chem Soc Perkm Trans 1307-314 (1982).

Hawser, S. P., E. J. Carpenter, G. A. Codd, and D. G. Capone, . A neurotoxic factor associated with the bloom-forming cyanobacterium *Trichodesmium*. Toxicon 29:277-278 (1991).

Hawser, S. P., J. M. O'Neil, M. R. Roman, and G. A. Codd., Toxicity of blooms of the cyanobacterium Trichodesmium to zooplankton, J. Appl. Phycol. 4:79-86 (1992).

Haygood, M.G.; Schmidt, E.W.; Davidson, S.K.; Faulkner, D.J. Microbial Symbionts of Marine Invertebrates: Opportunities for Microbial Biotechnology. J. Mol. Microbiol. Biotechnol. 1:33-34 (1999).

Hildebrand, M., L. Waggoner, H. Liu, S. Sudek, S. Allen, C. Anderson, D. Sherman, and M. Haygood, bryA: An Unusual Modular Polyketide Synthase Gene from the Uncultivated Bacterial Symbiont of the Marine Bryozoan *Bugula neritina* Chemistry and Biology, 11:1543-1552 (2004).

Hoogenboom et al, Human Antibodies from Synthetic Repertoires of Germline Vh Gene Segments Rearranged in Vitro. J Mol Biol. 227: 381 (1991).

Horswill AR, Benkovic SJ, Cyclic peptides, a chemical genetics tool for biologists, Cell Cycle, (4):552-5. Epub (2005).

Horton DA, Bourne GT, Smythe ML, Exploring privileged structures: the combinatorial synthesis of cyclic peptides, J Comput Aided Mol Des. 16(5-6):415-30 (2002).

Ibba and Hennecke, Towards engineering proteins by site directed incorporation in vivo of non natural amino acids. Review, Bio/technology, 12 678-682 (1994).

Ibba, Strategies for in vitro and in vivo translation with non-natural amino acids. Biotechnology & Genetic Engineering Reviews 13 197-216 (1995).

Ichinose, K., Bedford, D. J., Tornus, D., Bechthold, A., Bibb, M. J., Revill, W. P., Floss, H. G. & Hopwood, D. A. (1998) Chem. Biol. 5, 647-659.

Ireland CM, Durso AR, Newman RA and Hacker MP Antineoplastic cyclic peptides from the marine tunicate *Lissoclinum patella*. J Org Chem 47:1807-1811(1982).

Jack, R W & Jung, G, Lantibiotics and microcins: polypeptides with unusual chemical diversity, Curr Opm Chem Biol 4:310-317 (2000).

Karl, D., A. Michaels, B. Bergman, D. Capone, E. Carpenter, R. Letelier, F. Lipschultz, H. Paerl, D. Sigman, and L. Stal, Dinitrogen fixation in the world's oceans. Biogeochemistry 57/58:47-98 (2002).

Kimura R, Camarero JA, Expressed protein ligation: a new tool for the biosynthesis of cyclic polypeptides, Protein Pept Lett. 12(8):789-94 (2005).

Kinsella, T. M., Nolan, G. P., Episomal vectors rapidly and stably produce high-titer recombinant retrovirus. Hum. Gene Ther. 7:1405-1413 (1996).

Kirshenbaum, Highly efficient gene transfer into adult ventricular myocytes by recombinant adenovirus, J. Clin. Invest. 92:381-387 (1993).

Kleinkauf H, von Dohren H, Applications of peptide synthetases in the synthesis of peptide analogues, Acta Biochim Pol. 44(4):839-47 (1997).

Kline, T. C. and Lewin, R. A. Natural 15N/14N abundance as evidence for N2 fixation by Prochloron (Prochlorophyta) endosymbiotic with didemnid ascidians, Symbiosis 26:193-198 (1999).

Kobayashi and Ishibashi, Bioactive metabolites of symbiotic marine organisms, Chem. Rev. 93:1753-1770 (1993).

Koike, I., Yamamuro, M. & Pollard, P. C., Carbon and nitrogen budgets of two Ascidians and their symbiont, Prochloron, in a tropical seagrass meadow, Australian Journal of Marine and Freshwater Research, 44, 173-182 44, 173-182 (1993).

Lenes, et al., Iron fertilization and the *Trichodesmium* response on the West Florida shelf. Limnol. Oceanogr. 46: 1261-1277 (2001).

Letsinger et al, Cholesteryl-conjugated oligonucleotides: Synthesis, properties, and activity as inhibitors of replication of human immunodeficiency virus in cell culture Proc Natl Acad Sci USA, 86, 6553-6556 (1989).

Li, Y.-M., Milne, J. C., Madison, L. L., Kolter, R., Walsh, C. T., From Peptide Precursors to Oxazole and Thiazole-Containing Peptide Antibiotics: Microcin B17 Synthase. Science 274:1188-1193 (1996).

Litzinger and Huang, Biodistribution and immunotargetability of ganglioside-stabilized dioleoylphosphatidylethanolamine liposomes. Biochimica et Biophysica Acta, 1104: 179-187 (1992).

Long PF, Dunlap WC, Battershill CN, Jaspars M, Shotgun cloning and heterologous expression of the patellamide gene cluster as a strategy to achieving sustained metabolite production, Chembiochem 6(10):1760-1765 (2005).

Lusky, M L, et al, Bovine Papilloma Virus Contains an Activator of Gene Expression at the Distal End of the Early Transcription Unit. Molecular and Cellular Biology, p. 1108-1122 (Jun. 1983).

Madison, L. L. Vivas, E. I., Li, Yue-M, Walsh, C. T., and Kolter, R. Mol. Microbiol. 23, 161-168 (1997).

Milne J C, A C Eliot, N L Kelleher, C T Walsh, ATP/GTP hydrolysis is required for oxazole and thiazole biosynthesis m the peptide antibiotic microcosm B17 Biochemistry 37 13250-13261 (1998).

Milne, J. C., Roy, R. S., Eliot, A. C., Kelleher, N. L., Wokhlu, A., Nickels, B. & Walsh, C. T., Cofactor requirements and reconstitution of microcin B17 synthetase: a multienzyme complex that catalyzes the formation of oxazoles and thiazoles in the antibiotic microcin B17 Biochemistry 38, 4768-4781(1999).

Morley, J. S., Modulation of the Action of Regulatory Peptides by Structural Modification, Trends Pharm Sci., 463-468, (1980).

Namikoshi et al., Bioactive compounds produced by cyanobacteria J Ind Microbiol 17 373-384 (1996).

Newman DJ, Cragg GM: Marine natural products and related compounds in clinical and advanced preclinical trials. J Nat Prod 67:1216-1238 (2004).

Onaka H, M Nakaho, K Hayashi, Y Igarashi, T Furumai, Cloning and charactenzation of the goadsponn biosynthetic gene cluster from *Streptomyces* sp TP-A0584 Microbiology 151 3923-3933 (2005).

Pear et al, Production of high-titer helper-free retroviruses by transient transfection, PNAS USA 90(18) 8392-6 (1993).

Piel, J., Hui, D., Wen, G., Butzke, D., Platzer, M., Fusetani, N., Matsunaga, S., Antitumor polyketide biosynthesis by an uncultivated bacterial symbiont of the marine sponge *Theonella swinhoei*, Proc. Natl. Acad. Sci. USA 101:16222-16227 (2004).

Prufert-Bebout et al., Growth, nitrogen fixation, and spectral attenuation in cultivated *Trichodesmium* species, Appl. Environ. Microbiol. 59:1367-1375 (1993).

Rizo, J. & Gierasch, L.M., Constrained peptides—models of bioactive peptides and protein substructures, Ann. Rev. Biochem. 61:387-418 (1992).

Salomon, C. E. and Faulkner, D. J., Localization studies of bioactive cyclic peptides in the ascidian Lissoclinum patella, J. Nat. Prod. 65: 689-692 (2002).

Salvatella, X., J. M. Caba, F. Albericio, and E. Giralt, Solution of the antitumor candidate trunkamide A by 2D NMR restrained simulated annealing methods. J. Org. Chem. 68:211-215 (2003).

Schmidt, E. W., Nelson, J. T., Rasko, D. A., Sudek, S., Eisen, J. A., Haygood, M. G., Ravel, Patellamide A and C biosynthesis by a microcin-like pathway in Prochloron didemni, the cyanobacterial symbiont of Lissoclinum patella, J. Proc. Nat. Acad. Sci. USA, 102, 7315-7320 (2005).

Schmidt, E.W.; Sudek, S.; Haygood, M.G., Genetic evidence supports secondary metabolic diversity in Prochloron spp., the cyanobacterial symbiont of a tropical ascidian, J. Nat. Prod. 67:1341-1345 (2004).

Schnell, N., K.-D. Entian, U. Schneider, F. Götz, H. Zähner, R. Kellner, and G. Jung., Prepeptide sequence of epidermin, a ribosomally synthesized antibiotic with four sulphide-rings, Nature 333:276-278 (1988).

Scott CP, Abel-Santos E, Wall M, Wahnon DC, Benkovic SJ, Production of cyclic peptides and proteins in vivo, Proc Natl Acad Sci U S A. 96(24):13638-43 (1999).

Simmons, et al., Marine natural products as anticancer drugs, MoI Cancer Ther 4, 333-342 (2005).

Sings HL, Rinehart KL, Compounds produced from potential tunicate-blue-green algal symbiosis: a review, J Ind Microbiol Biotechnol 17: 385-396 (1996).

Solbiati, J. O., Ciaccio, M., Farías, R. N., González-Pastor, J. E., Moreno, F., Salomón, R. A., Sequence analysis of the four plasmid genes required to produce the circular peptide antibiotic microcin J25, J. Bacteriol. 181:2659-2662 (1999).

Sudek, S., Haygood, M. G., Youssef, D. T. A., Schmidt, E. W., Structure of Trichamide, a Cyclic Peptide from the Bloom-Forming Cyanobacterium Trichodesmium erythraeum, Predicted from the Genome Sequence.. Appl. Environ. Microbiol. 72: 4382-4387 (2006).

Swift, H. and D.L. Robertson, Structural aspects of a Prochloron-tunicate symbiosis. Symbiosis, 10:95-113 (1991).

Tan, L. T., Bioactive natural products from marine cyanobacteria for drug discovery. Phytochemistry 68:954-979 (2007).

Thorson et al , A Biosynthetic approach for the incorporation of unnatural amino acids into proteins. Methods in Molec Biol 77 43-73 (1991).

Tomitani, A., Okada, K., Miyashita, H., Matthijs, H. C. P., Ohno, T. & Tanaka, A., Chlorophyll b and phycobilins in the common ancestor of cyanobacteria and chloroplasts Nature 400, 159-162 (1999).

Trauger, et al., Peptide cyclization catalysed by the thioesterase domain of tyrocidine synthetase, Nature 407:215-218, (2000).

Williams et al., A marine natural product, patellamide D, reverses multidrug resistance in a human leukemic cell line, Cancer Lett 71, 97-102 (1993).

Wipf et al., Conformational studies and structure—activity analysis of lissoclinamide 7 and related cyclopeptide alkaloids, J Am Chem Soc 120, 4105-4112 (1998).

Withers et al., Pigment composition, photosynthesis and fine structure of a non-blue-green procaryotec algal symbiont (Prochloron sp_ in a didemnid ascidian from Hawaiian waters, Phycologia 17, 167-171 (1978).

Withers, N. W., Alberte, R. S., Lewin, R. A., Thornber, J. P., Britton, G. & Goodwin, T. W., Photosynthetic unit size, carotenoids, and chlorophyll-protein composition of Prochloron sp., a prokaryotic green alga, Proc. Natl. Acad. Sci. USA 75, 2301-2305 (1978).

Yokoboria, Kurabayashib, Neilanc, Maruyamad and Hirose, Multiple origins of the ascidian-Prochloron symbiosis: Molecular phylogeny of photosymbiotic and non-symbiotic colonial ascidians inferred from 18S rDNA sequences, Molecular Phylogenetics and Evolution 40(1):8-19 (2006).

Zabriskie, Foster, Stout, Clardy and Ireland, Studies on the Solution and Solid State Structure of Patellin 2, J. Am. Chem. Soc. 112, 8080-8084 (1990).

Preliminary Amendment filed May 28, 2010 with the USPTO for U.S. Appl. No. 12/281,373, filed Sep. 21, 2007 (1st Named Inventor—Schmidt) (13 pages).

Requirement for Restriction/Election mailed Jul. 14, 2011 by the USPTO for U.S. Appl. No. 12/281,373, filed Sep. 21, 2007 (1st Named Inventor—Schmidt) (11 pages).

Response to Requirement for Restriction/Election filed Nov. 11, 2011 with the USPTO for U.S. Appl. No. 12/281,373, filed Sep. 21, 2007 (1st Named Inventor—Schmidt) (8 pages).

Amended Response to Requirement for Restriction/Election filed Feb. 17, 2012 with the USPTO for U.S. Appl. No. 12/281,373, filed Sep. 21, 2007 (1st Named Inventor—Schmidt) (3 pages).

Non-final Rejection mailed Feb. 28, 2012 by the USPTO for U.S. Appl. No. 12/281,373, filed Sep. 21, 2007 (1st Named Inventor—Schmidt) (6 pages).

Response to Non-final Rejection filed Aug. 28, 2012 with the USPTO for U.S. Appl. No. 12/281,373, filed Sep. 21, 2007 (1st Named Inventor—Schmidt) (15 pages).

Non-final Rejection mailed Nov. 20, 2012 by the USPTO for U.S. Appl. No. 12/281,373, filed Sep. 21, 2007 (1st Named Inventor—Schmidt) (6 pages).

Examination Report No. 2 issued Jul. 2, 2012 by the Australian Patent Office for application 2007223427 filed on Mar. 1, 2007 (Applicant—University of Utah Research Foundation // 1st Named Inventor—Schmidt) (3 pages).

Response to Examination Report No. 1 filed Jun. 22, 2012 by the Australian Patent Office for application 2007223427 filed on Mar. 1, 2007 (Applicant—University of Utah Research Foundation // 1st Named Inventor—Schmidt) (31 pages).

Examination Report No. 1 issued Jun. 22, 2011 by the Australian Patent Office for application 2007223427 filed on Mar. 1, 2007 (Applicant—University of Utah Research Foundation // 1st Named Inventor—Schmidt) (3 pages).

European Search Report and Opinion issued Jul. 29, 2011 by the European Patent Office for application 07757735 filed on Mar. 1, 2007 (Applicant—University of Utah Research Foundation // 1st Named Inventor—Schmidt) (15 pages).

Noting of Loss of Rights issued Apr. 3, 2012 by the European Patent Office for application 07757735 filed on Mar. 1, 2007 (Applicant—University of Utah Research Foundation // 1st Named Inventor—Schmidt) (1 page).

Amendment before Examination filed Jun. 13, 2012 with the European Patent Office for application 07757735 filed on Mar. 1, 2007 (Applicant—University of Utah Research Foundation // 1st Named Inventor—Schmidt) (11 pages).

Decision to Allow Further Processing issued Jun. 26, 2012 by the European Patent Office for application 07757735 filed on Mar. 1, 2007 (Applicant—University of Utah Research Foundation // 1st Named Inventor—Schmidt) (1 page).

Communication from the Examining Division issued Oct. 1, 2012 by the European Patent Office for application 07757735 filed on Mar. 1, 2007 (Applicant—University of Utah Research Foundation // 1st Named Inventor—Schmidt) (7 pages).

* cited by examiner

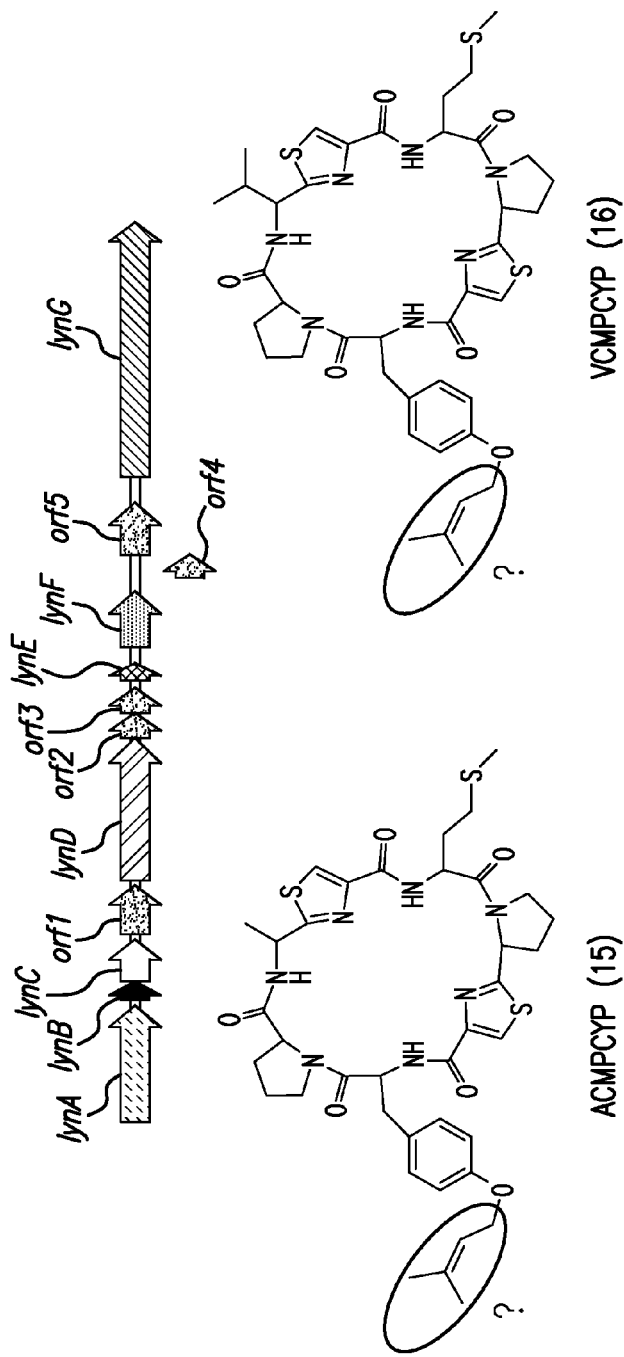

PatE1: MNKKNILPQQGQPVIRLTAGQLSSQLAELSEEALGDAGLEASVTACITFCAYDGVEPSITVCISVCAYDGE
TruE1: MNKKNILPQLGQPVIRLTAGQLSSQLAELSEEALGEALG--GVDASTLPVPTLCSYDGVDAS--TVPTLCSYDD
TenE: MDKKNILPQQGKPVIRITTGQLPSFLAELSEEALGDAGVGAS--ATGCMCAYDGAGAS--ATGCMCAYDGAGAS--ATACACAYDGAGASATACACAYE
LynE: MDKKNILPHQGKPVLRTTNGKLPSHLAELSEEALGGNGVDAS--ACMPCYPSYDGVDAS-VCMPCYPSYDGVDASVCMPCYPSYDDAE
TriG: MGKKNIQPNSSQPVFRSLVARPALEELREENLTEGNQGHGPLANGPGPSGDGLHPRLCSCSYDGDDE

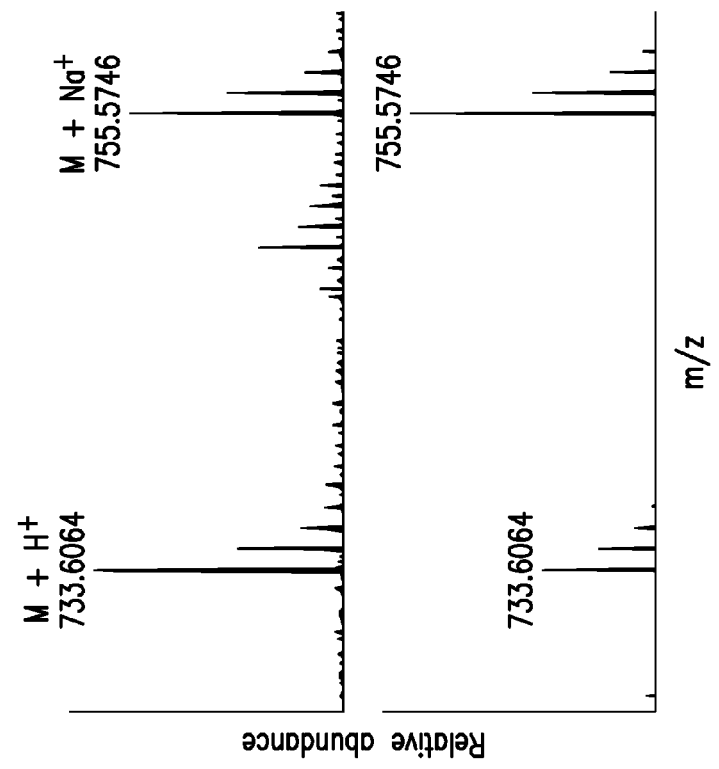
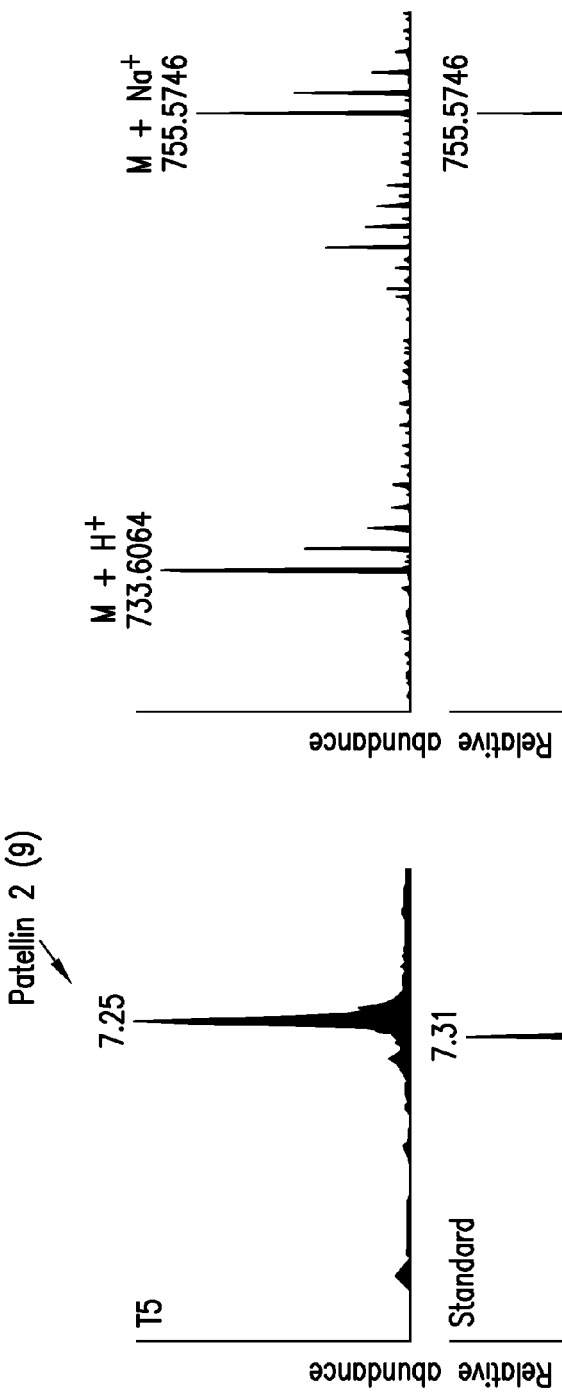
TruE2: MNKKNILPQLGQPVIRLTAGQLSSQLAELSEEALGGVDASTFPVPTVCSYDGVDASTSIAPFCSYDD
TruE3: MNKKNILPQLGQPVIRLTAGQLSSQLAELSEEALGGVDASTSIAPFCSYDGVDASTSIAPFCSYDD
TruE1: MNKKNILPQLGQPVIRLTAGQLSSQLAELSEEALGGVDASTLPVPTLCSYDGVDAS—TVPTLCSYDD
FIG.2a
FIG.2b
FIG.2c

METHODS AND COMPOSITIONS RELATED TO CYCLIC PEPTIDE SYNTHESIS

CROSS REFERENCE TO RELATED APPLICATIONS

This application is a continuation-in-part of U.S. patent application Ser. No. 12/281,373 filed Jan. 21, 2009, which is a national stage application of PCT US2007/063089, filed Mar. 1, 2007, which claims priority to U.S. Provisional Application Ser. No. 60/777,954 filed Mar. 1, 2006, all of which are hereby incorporated by reference.

ACKNOWLEDGEMENTS

This invention was made with government support under federal grant NIH R01 GM07142501A1 awarded by the NIH and NSF EF-0412226 subcontract from the Institute for Genomic Research. The Government has certain rights to this invention.

BACKGROUND

Marine ascidians are an excellent source of natural products (Davidson. S. Chem. Rev. 93, 1771-1791 (1993)), including ~60 cyclic peptides of the patellamide class, which constitute about 6% of natural products isolated from ascidians (MarinLit). Patellamide-containing ascidians harbor cyanobacterial symbionts, *Prochloron* spp., that have eluded cultivation. Recently, it was shown that *Prochloron didemni* is responsible for synthesizing cyclic peptides (Schmidt, E. W. et al. Proc. Nat. Acad. Sci. USA 102, 7315-7320 (2005); Long, P. F., Dunlap, W. C., Battershill, C. N. & Jaspars, M. ChemBioChem 6, 1760-1765 (2005)) that were originally isolated from the host ascidians (Ireland, C. M., Durso, A. R., Newman, R. A. & Hacker, M. P. J. Org. Chem. 47, 1807-1811 (1982); Degnan, B. M. et al. J. Med. Chem. 32, 1349-1354 (1989)). Surprisingly, single point mutations in short cassettes in the biosynthetic gene clusters resulted in a diverse product library (Donia, M. S. et al. *Nat. Chem. Biol.* 2, 729-735 (2006)). By mimicking this natural evolution, a new cyclic peptide was made using rational genetic engineering (Donia 2006.). A homologous pathway was found in the genome of a free-living cyanobacterium encoding a new natural product, trichamide (FIG. 1, peptide 2) (Sudek, S., Haygood, M. G., Youssef, D. T. & Schmidt, E. W. *Appl. Environ. Microbiol.* (2006)).

The patellamides (FIG. 1, peptides 3-8) are biosynthesized through a unique ribosomal route (Long et al.) with some similarity to microcin pathways (FIG. 1) (Li, Y.-M., Milne, J. C., Madison, L. L., Kolter, R. & Walsh, C. T. Science 274, 1188-1193 (1996)). The products' amino acid sequence is encoded directly on a precursor peptide, PatE (FIG. 1*f*) (Long et al). Short cassettes within the precursor peptide gene are hypervariable, resulting in a natural combinatorial library of cyclic peptides (Donia 2006). Outside of these cassettes, all known patellamide pathways are 99% identical to each other over their entire lengths (~11 kb) (Donia 2006). The following biosynthetic hypothesis was proposed (Long 2005; Sudek 2006). The encoding cassettes are flanked by recognition sequences that recruit enzymes for post-translational modifications. Among those are two proteases, PatA and PatG, which catalyze N—C terminal cyclization. PatD is responsible for heterocyclization of cysteine to thiazoline, which is then oxidized to thiazole by an oxidase domain in PatG. PatF may be involved in serine and threonine heterocyclization to oxazoline, among other possibilities. The proteins PatB and PatC were shown to be nonessential (Donia 2006).

Bacterial secondary metabolites are bioactive small molecules that often find use as pharmaceuticals. (Newman et al. J. Nat. Prod. 66, 1022-1037 (2003)). Numerous studies of secondary metabolite biosynthetic genes have led to an increasing ability to synthesize new small molecules through rational pathway engineering (Floss J. Biotechnol. epub (2006); Walsh, C. T. ChemBioChem, 124-134 (2002)). Much of this capability comes from gene sequence comparison, in which the observation of evolution of these pathways has enabled engineering. Despite the advances, a weakness of this approach is that most described pathways are relatively distantly related, making an analysis of single evolutionary events difficult to discern. This difficulty is compounded by the large number of dedicated enzymatic steps (up to approximately 60 or so) commonly required to synthesize individual secondary metabolites.

Small, cyclic peptides are valuable pharmaceuticals, biotechnological products, and tools for scientific research (Davies, J. S. Amino Acids, Peptides and Proteins 2003, 34, 149-217). Cyclic peptides in general have advantages over their linear relatives in that they sample a more constricted conformational and configurational space. (Payne et al. Curr. Org. Chem. 2002, 6, 1221-1246). Stemming from this basic property, cyclic peptides often have stronger binding constants and favorable pharmacological properties such as resistance to proteases (Fairlie, D. P.; Tyndall, J. D. A.; Reid, R. C.; Wong, A. K.; Abbenante, G.; Scanlon, M. J.; March, D. R.; Bergman, D. A.; Chai, C. L. L.; Burkett, B. A. J. Med. Chem. 2000, 43, 1271-1281). Because of this, numerous investigators have developed means to produce arrays of small, cyclic peptides. Synthetic and enzymatic systems, as well as combinations of the two, have been used successfully on small and medium scale (Davies et al. J. Peptide Sci. 2003, 9, 471-501; Hahn et al. Proc. Nat. Acad. Sci. USA 2004, 101, 15585-15590). At the large scale, peptides in phage-display libraries have been cyclized via disulfide bonds or via semi-synthesis from the same libraries (Kehoe, J. W.; Kay, B. K. Chem. Rev. 2005, 105, 4056-4072; Ho, K. L.; Yusoff, K.; Seow, H. F.; Tan, W. S. J. Med. Virol. 2003, 69, 27-32).

There is a great need for new methods for making cyclic peptides, particularly for the manufacture of synthetic cyclic peptides for clinical investigations and therapeutic use, and for the production of cyclic peptide libraries that can be screened to identify cyclic peptides with a desired activity. What is needed in the art are methods for the in vivo construction of cyclic peptide libraries, as well as the compounds resulting therefrom.

SUMMARY

Disclosed are methods and compositions related to prenylation of polymers such as peptides.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 2 shows the tru pathway to patellins and trunkamide. (a), The precursor peptide variants TruE1-E3 are shown. Product-coding sequences are in blue and underlined while recognition sequences are in red and bold. TruE1 encodes for patellins 2 and 3, TruE2 encodes for patellin 6 and trunkamide, and TruE3 encodes for three copies of trunkamide. (b) and (c), The tru pathway was expressed in *E. coli* and broth was analyzed by high resolution mass spectrometry. Top: *E. coli* broth; bottom: standard of patellins 2 and 3. Data are shown for patellin 2 and a similar pattern was observed for patellin 3 (FIG. 5). (a), A total ion chromatogram filtered for m/z=733 corresponding to patellin 2 is shown. Both the standard and the recombinant product eluted at exactly the same time. (b), The mass of the recombinant product exactly matched that of the standard to four decimal places.

DETAILED DESCRIPTION

Figure 1A:
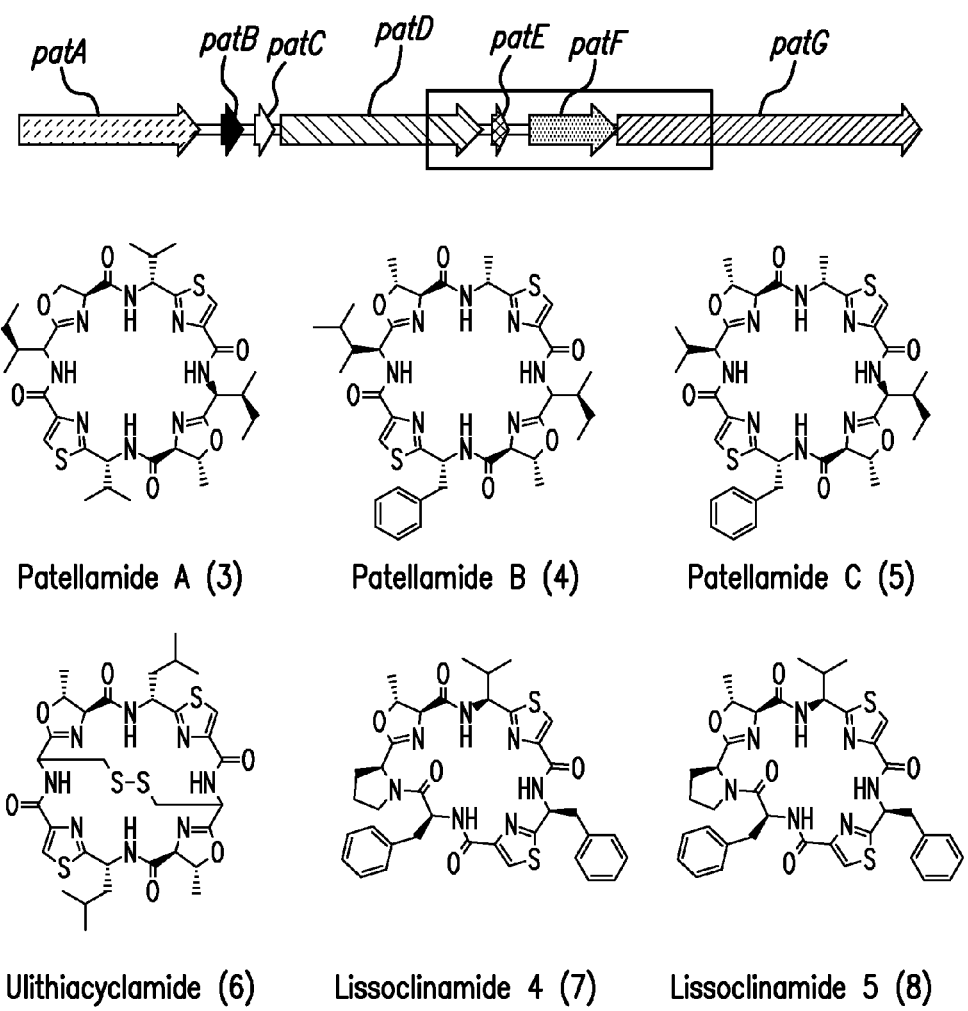
FIG. 1 shows cyanobactin pathways in cyanobacteria. Five cyanobactin gene clusters are represented by arrows, while their associated small molecule products are shown below. Conserved genes are indicated as identically colored arrows in the pathways. (a), pat cluster and biosynthetically identified products from the patellamide, lissoclinamide and ulithiacyclamide families of compounds. (b), tru cluster and identified products from the patellin and trunkamide families. The part of the pathway where pat and tru differ is boxed in blue. (c), ten and identified products tenuecyclamide A and C. (d), tri cluster and identified product trichamide. (e), lyn cluster and predicted products. (f), The amino acid sequences of the encoded cyanobactin products are shown in blue and underlined, while probable recognition sequences are shown in red and bold. PatE1 encodes for patellamides C and A; TruE1 encodes for patellins 2 and 3; TenE encodes for two tandem copies of each of tenuecyclamides C and A; LynE encodes for two predicted products; TriG encodes for trichamide.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

A "cyclic polypeptide" is a type of conformationally restrained polypeptide that, as its name suggests, contains a cyclic polymer of amino acids. The term "cyclic polypeptide" is used to describe a polypeptide (including a cyclic peptide) that is circularized via a peptide bond between the N and C terminal amino acids of a linear polypeptide (as described in U.S. published patent application 20040014100, for example).

The term "randomized amino acid sequence" refers to a polypeptide having an amino acid sequence that is at least partially randomized, including fully randomized. When made recombinantly, a library of polypeptides having randomized amino acid sequences usually contains polypeptides having any of the naturally occurring amino acids, or any subset thereof, present into at least one or all positions (e.g., at last 1, 2, 3, 4, 5, about 8, about 10, about 15, about 20, usually up to at least 100 or more positions) of the polypeptide. Polypeptides having a randomized amino acid sequence are usually produced using synthetic nucleic acids that contain any of the four nucleotides, or a subset thereof, in at least one or all positions of the polynucleotide.

As used herein, the terms "manage," "managing" and "management" refer to the beneficial effects that a subject derives from administration of a prophylactic or therapeutic agent, which does not result in a cure of the disease or diseases. In certain embodiments, a subject is administered one or more prophylactic or therapeutic agents to "manage" a disease so as to prevent the progression or worsening of the disease or diseases.

As used herein, the terms "prevent", "preventing" and "prevention" refer to the methods to avert or avoid a disease or disorder or delay the recurrence or onset of one or more symptoms of a disorder in a subject resulting from the administration of a prophylactic agent.

As used herein, the term "in combination" refers to the use of more than one prophylactic and/or therapeutic agents. The use of the term "in combination" does not restrict the order in which prophylactic and/or therapeutic agents are administered to a subject with a disorder, e.g., hyperproliferative cell disorder, especially cancer. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to a disorder. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

The term "suitable" as used herein refers to a group that is compatible with the compounds, products, or compositions as provided herein for the stated purpose. Suitability for the stated purpose may be determined by one of ordinary skill in the art using only routine experimentation.

As used herein, the terms "administer" when used to describe the dosage of a compound, means a single dose or multiple doses of the compound.

As used herein, the term "cancer treatment" means any treatment for cancer known in the art including, but not limited to, chemotherapy and radiation therapy.

As used herein, "tumor cells" means both cells derived from tumors, including malignant tumors, and cells immortalized in vitro. "Normal" cells refer to cells with normal growth characteristics that do not show abnormal proliferation.

As used herein, the terms "an individual identified as having cancer" and "cancer patient" are used interchangeably and are meant to refer to an individual who has been diagnosed as having cancer. There are numerous well known means for identifying an individual who has cancer. In some embodiments, a cancer diagnosis is made or confirmed using PET imaging. Some embodiments of the invention comprise the step of identifying individuals who have cancer.

As used herein, the term "therapeutically effective amount" is meant to refer to an amount of an active agent or combination of agents effective to ameliorate or prevent the symptoms, shrink tumor size, or prolong the survival of the patient being treated. Determination of a therapeutically effective amount is well within the capabilities of those skilled in the art, especially in light of the detailed disclosure provided herein.

As used herein the term "inhibit" or "inhibiting" refers to a statistically significant and measurable reduction in activity, preferably a reduction of at least about 10% versus control, more preferably a reduction of about 50% or more, still more preferably a reduction of about 80% or more.

As used herein the term "increase" or "enhancing" refers to a statistically significant and measurable increase in activity, preferably an increase of at least about 10% versus control, more preferably an increase of about 50% or more, still more preferably an increase of about 80% or more.

The terms "antagonist" and "inhibitor" are used interchangeably to refer to an agent that decreases or suppresses a biological activity.

An "effective amount" of, e.g., an inhibitor, with respect to the subject method of treatment, refers to an amount of the inhibitor in a preparation which, when applied as part of a desired dosage regimen brings about a desired clinical or functional result. When a particular functional activity is only readily observable in an in vitro assay, the ability of a compound to inhibit in that in vitro assay serves as a reasonable proxy for the activity of that compound.

The term "prevent" or "preventing" when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The terms "pool" or "mixture", as used herein, refers to a combination of elements, e.g., cells or polypeptides, that are interspersed in two or three dimensions and not in any particular order. A mixture is homogeneous and not spatially separable into its different constituents. Examples of mixtures of elements include a number of different polypeptides that are present in the same solution (e.g., an aqueous solution). In other words, a mixture is not addressable. To be specific, an arrayed library of polypeptides, as is commonly known in the art, is not a mixture of polypeptides because the elements of the library are spatially distinct and the array is addressable.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a receptor modulator that can provide for enhanced or desirable effects in the subject (e.g., reduction of pathogen load, beneficial increase in a physiological parameter of the subject, reduction of disease symptoms, etc.).

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. General

Figure 3:
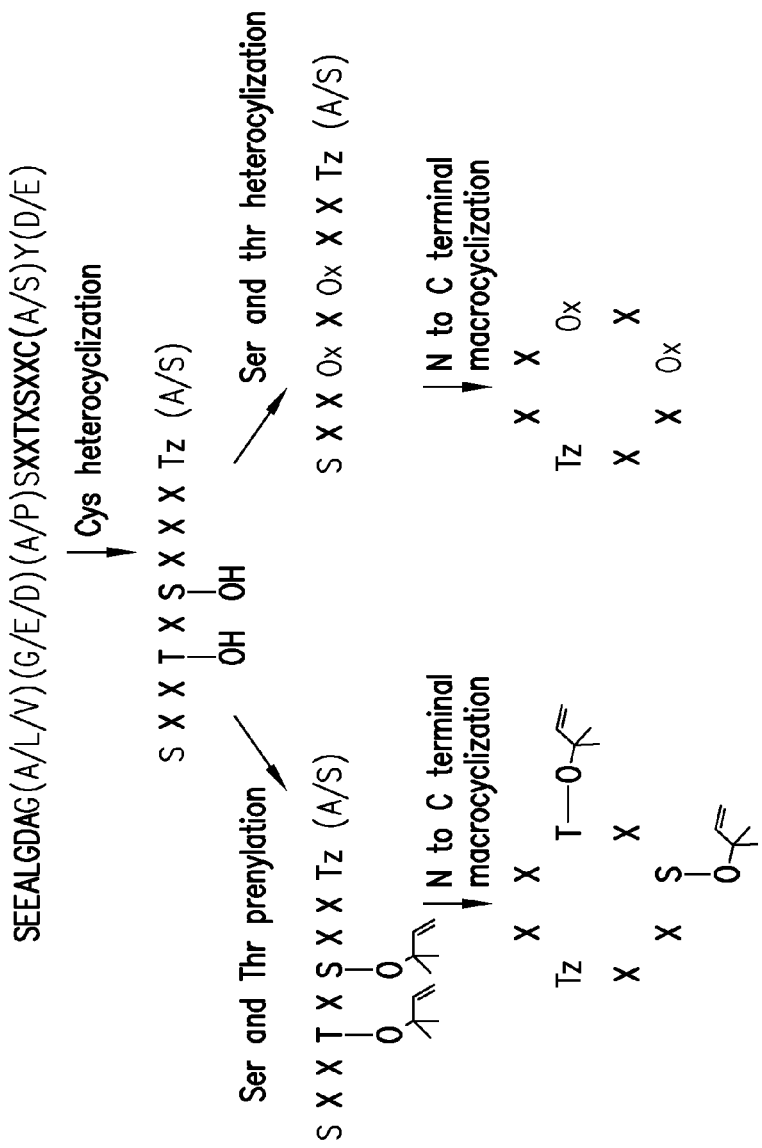
FIG. 3 shows the general schematic of cyanobactins biosynthesis. Cyanobactin precursors can be heterocyclized or prenylated at Ser/Thr during the post-translational modification process. Probable recognition sequences are shown in red and bold. An example product-coding sequence is highlighted in yellow. X indicates any amino acid while other letters indicates the universal amino acid code. Tz=thiazole or thiazoline and Ox=oxazole or oxazoline.

Numerous patellamide relatives have been isolated from marine invertebrates, including some with unprecedented chemical motifs. For example, a large number of patellins and derivatives have been isolated from ascidians (FIG. 1, peptides 9-12) (Carroll, A. R. et al. Aust. J. Chem. 49, 659-667 (1996); Zabriskie, T. M., Foster, M. P., Stout, T. J., Clardy, J. & Ireland, C. M. J. Am. Chem. Soc. 112, 8080-8084 (1990)). These metabolites are prenylated at serine and threonine rather than being heterocyclized and were proposed to be of cyanobacterial origin (FIG. 3). In addition, heterocyclized cysteine residues remain at the reduced thiazoline stage (Carroll 1996; Zabriskie 1990). Like patellamides, the patellin family has been isolated only from *Prochloron*-containing ascidians. They are known to be cytotoxic, and one member of this group, trunkamide, was a preclinical antitumor candidate (Salvatella, X., Caba, J. M., Albericio, F. & Giralt, E. J. Org. Chem. 68, 211-215 (2003)). Many patellamide-like compounds have also been reported from free-living cyanobacteria (Tan, L. T. Phytochemistry 68, 954-979 (2007)) Examples include the tenuecyclamides (FIG. 1, peptides 13, 14), which potently inhibit the division of sea urchin embryos (Banker, R. & Carmeli, S. J. Nat. Prod. 61, 1248-1251 (1998)). Because tenuecyclamide-like peptides are common in free-living cyanobacteria, and because of the prenylation event found in trunkamide and related ascidian compounds, a study of their biosynthesis was undertaken. These pathways have conserved features that warrant their inclusion in a new family of cyanobacteria-specific compounds, the cyanobactins.

1. Patellamides

Patellamides are a family of N—C terminally cyclized peptide natural products isolated from marine ascidians (Ireland, C. M.; Durso, Jr., A. R.; Newman, R. A.; Hacker, M. P. J. Org. Chem. 1982, 47, 1807-1811) (FIG. 1). These peptides and their relatives often contain thiazole, thiazoline, and oxazoline heterocycles derived from Cys, Thr, and Ser. They form a large family of molecules, some of which are relatively unrelated to the parent patellamide structure (Davidson, B. S. Chem. Rev. 1993, 93, 1771-1791; Sings et al. Ind. Mirobiol. 1996, 17, 385-396; Schmidt et al. J. Nat. Prod. 2004, 67, 1341-1345). To investigate the biosynthesis and biotechnological utility of this family, the patellamide A/C biosynthetic gene cluster, pat, was cloned and synthesized from an uncultivated bacterial symbiont of ascidians (FIG. 1). When expressed in *E. coli*, pat led to the production of very small amounts of patellamides (Long et al. ChemBioChem, 2005, 6, 1-7). This represented the first fully validated natural product pathway from uncultured symbionts.

pat is composed of seven coding sequences, patA-G, which had little to no similarity with other characterized gene clusters. PatE encoded the cyclic peptides, patellamides A and C, directly on a single prepeptide (FIG. 1). Putative start- and stop-cyclization recognition sequences were found, leading to the speculation that the coding sequences themselves could be modified to produce new, cyclic peptides.

pat was originally cloned from an environmental (uncultured) bacterial sample, and the intact pathway produced low levels of patellamides. Therefore, patA-G were cloned and expressed in compatible DUET vectors in *E. coli*. On the basis of sequence analysis, it was predicted that PatA, PatD, PatE, and PatG would be required for patellamide biosynthesis. PatE, as the direct patellamide prepeptide, is obviously a required precursor. PatD has low sequence similarity to a series of enzymes involved in thiazole formation in a group of microcins, (Roy et al. Nat. Prod. Rep. 1999, 16, 249-263; Milne et al. Biochemistry 1999, 38, 4768-4781; Kelleher et al. Biochemistry, 1999, 38, 15623-15630) indicating that it is likely required for the same function in pat. PatA and PatG both contained serine protease domains that were predicted to be involved in maturation (Chatterje et al. A. Chem. Rev. 2005, 105, 633-683) and cyclization of patellamides. In addition, PatG harbored an N-terminal domain with homology to FAD-dependent oxidases, indicating that it would likely be required to synthesize thiazole from thiazoline. The other three predicted coding sequences, PatB, PatC, and PatF, had no significant similarity to any protein with known function.

It was discovered that patE2, which was identical to patE except that the nucleotides encoding patellamide A were neatly replaced with those encoding the known compound, ulithiacyclamide. patE2 was used for the studies described, in part because ulithiacyclamide was much more readily detected in comparison to patellamide A or C. In order to achieve better production with patE2, all pat genes were removed from their native context and placed under control of individual T7 promoters in *E. coli*. Production of patellamides and ulithiacyclamide was monitored by HPLC-ESI-MS, using an authentic standard of ulithiacyclamide as a positive control.

Co-expression of the full gene set patA-G followed by subtraction of genes one at a time led to the discovery that PatADE2G was required, but that PatF was also required for patellamide C/ulithiacyclamide production. PatB and PatC, by contrast, were not necessary for the production of the patellamides, although PatB increased the detected yield. Strains that lacked any of the proteins PatADE2FG did not make patellamides. On this basis, the minimal gene set was defined as patADEFG (FIG. 2).

A series of pat relatives encoding both new and known products were identified. Only the patellamide-like coding sequences were mutated, while other sequences remained identical. However, most of the mutations were relatively conservative, in that aliphatic amino acids could be swapped, and Thr and Ser were interchangeable. Thus, it was sought whether less conservative mutations could be tolerated by the pat system.

A mutant, patEdm, was synthesized in which the entire ulithiacyclamide sequence was swapped with a sequence encoding "eptidemnamide". This new peptide sequence has no biosynthetic precedent in the literature, is not related in any way to known patellamide relatives, and was meant to be an amide-cyclized relative of the clinically used disulfide-bridged anticoagulant, eptifibatide (Curran, M. P.; Keating, G. M. Drugs 2005, 65, 2009-2035). In contrast to patellamides, eptidemnamide contains charged and polar residues and new hydrophobic amino acids Trp and Gly. This new peptide was designed in order to define the sequence tolerance of PatADFG in one step.

patEdm was synthesized in a single round of mutational PCR, (Kunkel, T. A. Proc. Nat. Acad. Sci. USA 1985, 82, 488-492) and its identity was verified by sequencing. In addition, a mutant patEdm* was discovered in a clone library that was very similar to patEdm but contained a $P^{56}$-Q mutation in the recognition sequence immediately upstream of eptidemnamide. Both patEdm and patEdm* were cloned into pRSF-DUET vector and co-expressed with patABDFG. By HPLC-ESI-MS analysis, the strain containing patEdm produced eptidemnamide, while the patEdm* strain did not produce any detectable new compound. From the patEdm-expressing strain, eptidemnamide was isolated, and its structure verified by NMR and ESI-FTMS. These experiments demonstrate the crucial nature of the recognition region in controlling peptide cyclization, while also showing that the coding sequences of these peptides can be varied greatly.

The absolute configuration of the new compound can be all L, based upon the following consideration: In all cases, patellamides and relatives contain L-amino acids except adjacent to thiazole, in which case D- or L-amino acids are present. As noted by numerous synthetic and natural products chemists, this position is notoriously labile, undergoing racemization under many different conditions (Milne et al. Org. Biomol. Chem. 2006; Wipf et al. J. Am. Chem. Soc. 1998, 120, 4105-4112).

The experiments described above are useful in the enzymatic synthesis of cyclic peptide libraries by allowing the rapid construction of C—N terminally amide-linked cyclic peptides on a reasonable scale. In addition, the biosynthetic gene set has been defined, facilitating a complete biochemical analysis of the unique steps involved in the synthesis of this family of compounds. Finally, numerous compounds have been isolated from marine invertebrates, many with novel architectures and functional groups (Blunt et al. Nat. Prod. Rep. 2006, 23, 26-78; Newman et al. J. Nat. Prod. 2004, 67, 1216-1238; et al. Mol. Cancer. Ther. 2005, 4, 333-342).

Also disclosed is the enzymatic synthesis of prenylated peptide libraries using those peptides disclosed herein.

2. Trichamide

A gene cluster for the biosynthesis of a new small cyclic peptide, dubbed trichamide, was discovered in the genome of the global, bloom-forming marine cyanobacterium *Trichodesmium erythraeum* ISM101 because of striking similarities to the previously characterized patellamide biosynthesis cluster. The tri cluster consists of a precursor peptide gene containing the amino acid sequence for mature trichamide, a putative heterocyclization gene, an oxidase, two proteases and hypothetical genes. Based upon detailed sequence analysis, a structure was predicted for trichamide and confirmed by Fourier-transform mass spectrometry. Trichamide consists of 11 amino acids, including two cysteine-derived thiazole groups, and is cyclized by an N—C terminal amide bond.

*Trichodesmium* is a genus of marine diazotrophic, non-heterocysteous cyanobacteria. It occurs throughout the open waters of oligotrophic tropical and subtropical oceans and forms filaments (trichomes) of 20-200 cells that can further aggregate into colonies several millimeters across. *Trichodesmium* can form enormous blooms in excess of 100,000 $km^2$ (Karl et al. 2002. Dinitrogen fixation in the world's oceans. *Biogeochemistry* 57/58: 47-98), which are most commonly composed of *T. erythraeum* and *T. thiebautii*. *Trichodesmium* sp. have been the subject of intense research mainly for two reasons. First, they contribute a significant portion (40% or more) to global oceanic nitrogen fixation, thereby directly affecting the biogeochemical carbon flux in tropical oceans with implications for the world's climate.

Second, massive coastal *Trichodesmium* blooms have been reported to have toxic effects, both directly on invertebrates (Guo C., P. A. Tester. 1994. Toxic effect of the bloom-forming *Trichodesmium* sp. (Cyanophyta) to the copepod *Acartia tonsa*. *Nat. Toxins* 2: 222-227; Hawser S. P., J. M. O'Neil, M. R. Roman, G. A. Codd. 1992. Toxicity of blooms of the cyanobacterium *Trichodesmium* to zooplankton. *J. Appl. Phycol*. 4: 79-86) and on humans ("*Trichodesmium* or Tamandare fever", (Sato et al. *Trab. do Instil. Oceanogr. Univ. Fed. de Pernambuco Recife* 5/6: 7-50) as well as indirectly by inducing blooms of other organisms (Devassy et al 1979. Indian J. Mar. Sci. 8: 88-93; Lenes et al. 2001. Limnol. Oceanogr. 46: 1261-1277) that can be potentially harmful. While cyanobacteria are a prolific source of diverse natural products and toxins (Carmichael W. W. 1992. 72: 445-459; Gerwick et al. 2001. Alkaloids Chem. Biol. 57: 75-184; Namikoshi et al. 1996. Bioactive compounds produced by cyanobacteria. J. Ind. Microbiol. 17: 373-384), a toxic compound (or any natural product) has not been isolated from a *Trichodesmium* species despite some efforts (Hawser et al. 1991. *Toxicon* 29: 277-278].

BLAST searches in GenBank with the pat genes revealed homologs in *T. erythraeum* IMS101. This led to the investigation of a potential patellamide-like biosynthesis cluster as well as its product, a small cyclic peptide, dubbed trichamide in *T. erythraeum*.

3. Trunkamide/Prenylation

Prenylated peptides can also be formed using the peptides disclosed herein. Prenylation can be useful for a variety of reasons. For example, it can be useful in the synthesis of peptide libraries with an unprecedented modification. This can be used in drug discovery, for example. Prenylation can also be useful in the synthesis of peptide libraries with other prenyl modifications, including farnesylation and geranylation. Such modifications are important in cell signaling, especially as related to cancers.

Prenylation provides a unique handle for chemical modification of peptides, either individually or in library format. For example, this modification is useful in fluorescent labeling of peptides, for surface labeling, or for addition of specific functional groups. In the case of fluorescent labeling, modified peptides are used to determine a drug's mechanism of action, to probe cellular events by microscopy, as reagents or components in fluorescent detection kits (for metals, drug interactions, etc.), or as clinical diagnostic agents. Surface labeled peptides can also find use as arrayed libraries for drug discovery. Surfaces are labeled via metathesis or by other well known reactions involving terminal olefins. For the addition of specific functional groups, terminal olefins provide a robust chemical platform. Examples of functionalization include fluorescent labeling, surface labeling, addition of hydrophobic or hydrophilic groups, addition of drugs or other small molecules, addition of specific functional groups to increase drug interactions via avidity effects, and many others which are known to those of skill in the art and herein contemplated.

Prenylation was an ancestral function, and the enzymes gradually evolved to catalyze the other function (heterocyclization). Prenylation is a new type of posttranslational modification, and the regioselectivity of prenylation is a useful aspect. Posttranslational modifications include phosphorylation, acetylation, glycosidation, and other extremely important events in cell biology.

Disclosed herein is a method for diagnosing a disease in a subject, the method comprising: obtaining a sample from the subject, contacting the sample with a prenylated peptide library, wherein the prenylated peptide library is specific for the disease; identifying interaction between the sample and the prenylated peptide library, wherein such interaction indicates diagnosis of the disease. The disease can be cancer, or can be an infectious disease, such as that caused by a virus, fungi, or bacteria.

The sample which is contacted with the prenylated peptides can be a from any biological fluid or mass, such as sera, blood, sputum, or tissue culture. In one example, the sample is from a tumor. The diagnostic assay can comprise the recognition of an antibody, which would indicate the presence of a given disease or disorder. For example, an antibody which is associated with a given disease or disorder can interact with the prenylated peptide library, thereby indicating that a diseased state is present in the subject from which the sample was obtained.

The prenylated peptide library can immobilized on a substrate, such as an array, and the array can be high-throughput. Such arrays are known in the art and are described herein. The array can comprise prenylated peptides, or can comprise test samples which are then contacted with prenylated peptides in solution. In either case, the prenylated peptide interacts with a test sample, such as binding to a surface molecule of the test sample. In one example, the surface molecule can comprise a cell surface protein, a lipid, a carbohydrate, an envelope protein or an envelope glycoprotein. Either the test sample or the prenylated peptide can comprise a detectable marker. Again, such markers are known to those of skill in the art.

Also disclosed is a prenylated peptide library. Such a library is comprised of prenylated peptides which can be specific for a known disease or condition, or which are randomly generated. The creation of such libraries is generally known in the art, and can be applied to prenylated peptide libraries. Further disclosed are kits comprising such prenylated peptide libraries. These kits can be specific for a known pathogen or disease (such as a given cancer marker), or can be randomly generated. In one example, the prenylated peptide library can interact with an antibody which is known to be associated with a given disease or disorder. The antibody, for instance, can comprise a detectable label.

Also disclosed is a method for screening for a prenylated peptide that interacts with a given composition, the method comprising exposing the given composition to a prenylated peptide, and determining interaction between the prenylated peptide and the given composition. The prenylated peptide can be produced by the methods disclosed herein for prenylating peptides. The prenylated peptide c an be part of a library, or can be used individually. The given composition can a protein, antibody, or nucleic acid, for example. This method can be used to screen for drugs that interact with a given composition, thereby inhibiting or enhancing its activity. The given composition can be associated with a disease or disorder, such as cancer or an infectious disease. Such disease and disorders are enumerated throughout. Interaction between the prenylated peptide and given composition can indicate that the prenylated peptide is useful in treating the disease or disorder.

Also disclosed is a method of treating a disease or disorder, comprising contacting a subject with a prenylated peptide made or identified by the methods disclosed herein. The prenylated peptide can be used to treat or prevent a disease or disorder associated therewith. For example, the prenylated peptide can be used to inhibit a given protein, or to interact with a pathogen, thereby inhibiting its ability to infect. The prenylated peptide can be given in conjunction with a second composition known to treat the disease or disorder, for example. An example of a second composition is a known drug or antibiotic, or an antibody.

The prenylated peptides disclosed herein can also be used to enhance the effectiveness of a second composition. This can done by increasing the effectiveness of the second composition, such as enhancing delivery of the second composition to the target, or by both the prenylated peptide and the second composition working in concert on different aspects of the disease or disorder. Such methods of enhanced effectiveness by combination therapy are known to those of skill in the art.

Also disclosed is a method of enhancing the effectiveness of a known peptide, the method comprising prenylating the known peptide. Such methods of prenylation are disclosed herein. The peptide can be known already to have effectiveness in treating a given disease or disorder, and prenylation of the peptide can increase the effectiveness by enhancing delivery, or by increasing the efficacy of the peptide. The known peptide can an antitumor or an antimicrobial composition, for example.

Figure 4:
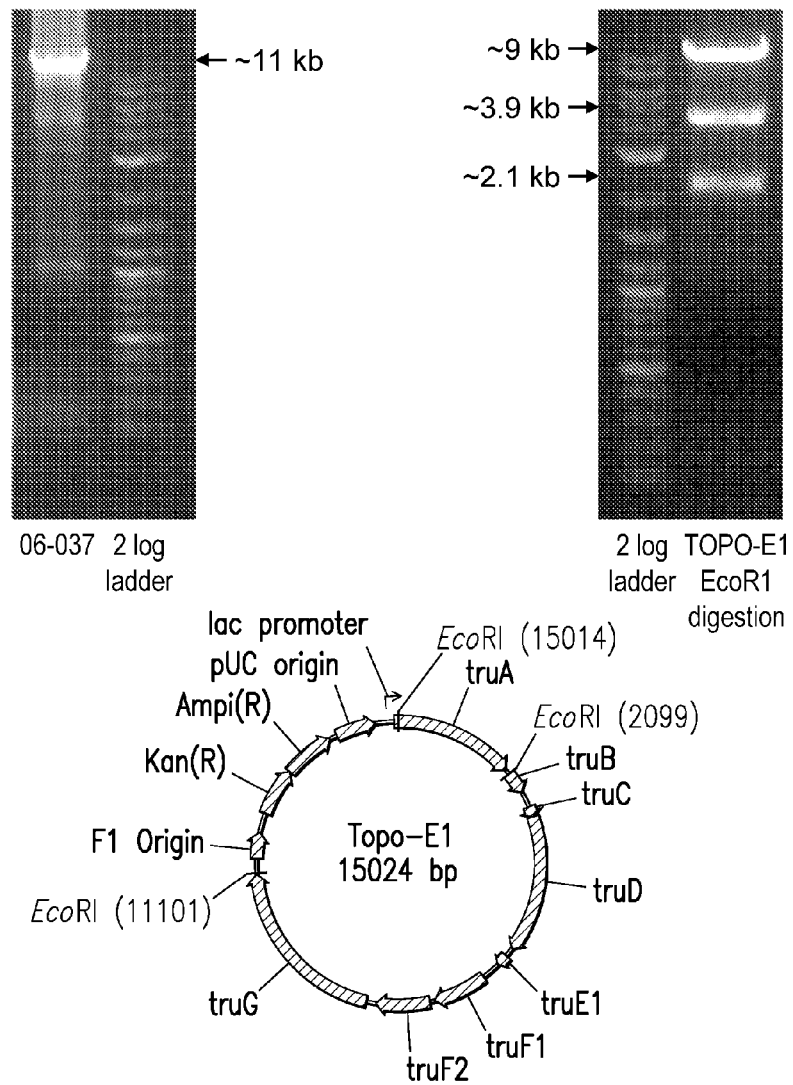
FIG. 4 shows TOPO-E1 vector construction, validation and expression. Left, gel electrophoresis of the ~11 kb PCR product harboring the full tru1 cluster amplified from DNA from sample 06-037. Right, an EcoR1 restriction digest of the vector TOPO-E1 where the full tru1 cluster is cloned upstream of the lac promoter. Middle, a map of the resulting vector where the EcoR1 cut sites are shown.
Figure 5:
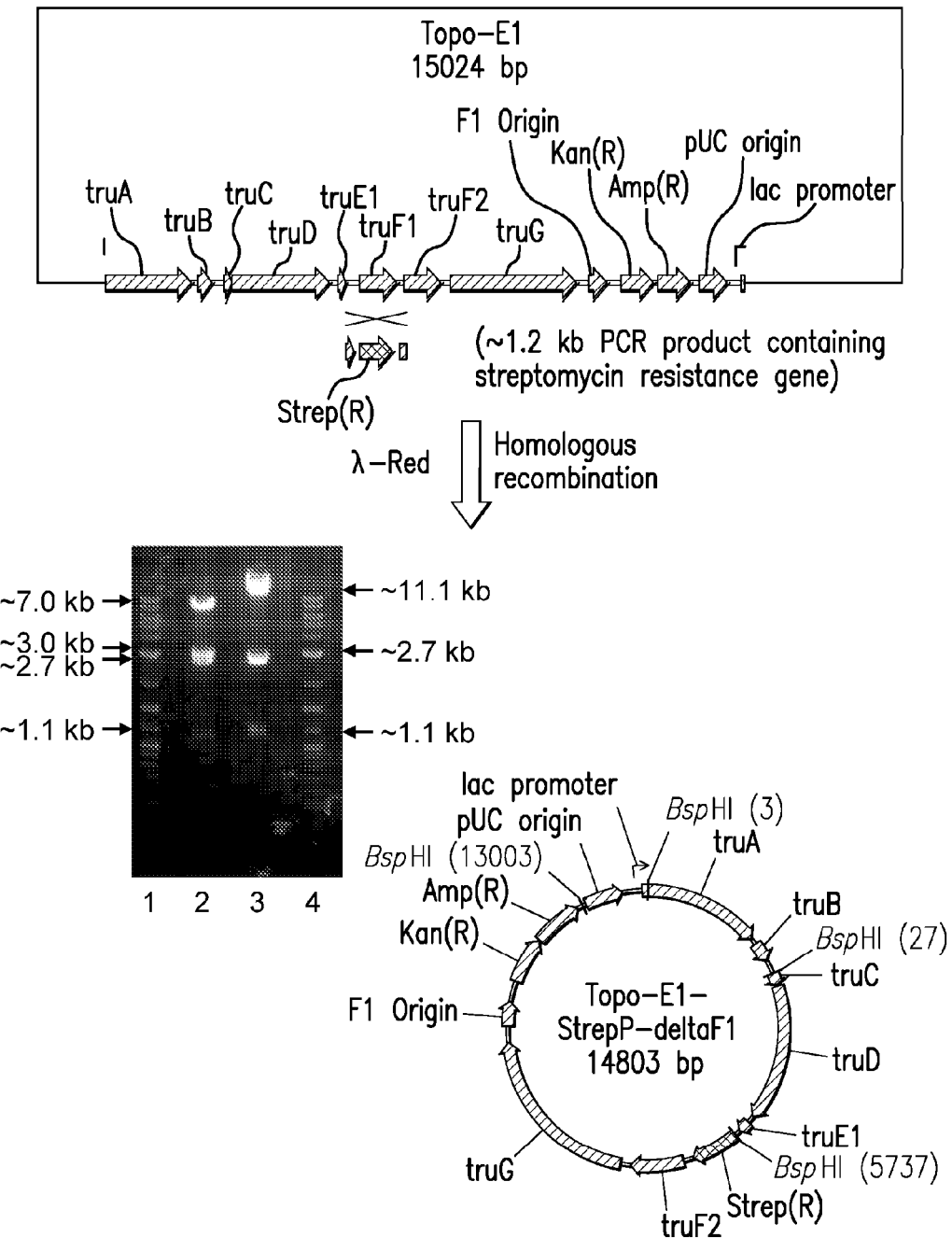
FIG. 5 shows TOPO-E1 map is shown on top and was crossed over by a 1.2 kb PCR product containing the streptomycin resistance gene to yield the truF1 knock out vector TOPO-E1-Strep-ΔF1 (map shown at the bottom). Agarose gel lane 1, 4: 2-log ladder; lane 2: BspH1 digest of TOPO-E1-Strep-ΔF1; lane 3, BspH1 digest of TOPO-E1.

In order to determine whether *Prochloron* bacteria synthesize prenylated peptides within ascidians, several candidate ascidians were collected in Fiji and the Solomon Islands (Methods section). After chemical screening, prenylated cyclic peptides were found in three samples: *Lissoclinum patella* and *Didemnum molle* from adjacent locations in the Solomon Islands; and *L. patella* from Fiji. *Prochloron* cells were enriched from the Fiji sample and a fosmid library was constructed, leading to the discovery of the patellin pathway tru on a single fosmid (FIG. 1b). This fosmid was sequenced and found to contain a patellamide-like biosynthetic pathway directly encoding patellins 2 and 3 on a precursor gene (similar to patE in the pat cluster, FIG. 1f). This observation was consistent with the chemical analysis of the ascidian sample. To further demonstrate that the tru cluster is necessary and sufficient for the biosynthesis of the prenylated products, the cluster was transferred to *E. coli*. The ~11 kb cluster was amplified by PCR, cloned, and expressed in *E. coli*. The fractionated expression broth was analyzed by mass spectrometry and compared to authentic standards. Both patellins 2 and 3—isolated originally from the ascidian sample—were detected in an approximate yield of 100 μg $L^{-1}$ in three separate experiments (FIG. 2 and FIG. 4). These results show that the tru cluster is responsible for the biosynthesis of the patellins, including the prenylation. To further demonstrate the involvement of the cluster in patellin 2 and 3 biosynthesis and to develop tools for pathway engineering, a knockout vector was constructed using the tru expression plasmid in which the truF1 gene was cleanly replaced with a streptomycin resistance gene (FIG. 5). The resulting construct was transferred to *E. coli*, and the extract was analyzed for the presence of cyclic peptides. No products were detected from a 10 L fermentation, further validating the tru operon.

The precursor peptide TruE (FIG. 1f) directly encodes the amino acid sequence of the octapeptide patellin 3 and the hexapeptide patellin 2. Putative recognition sequences were similar to those found in the patellamide precursor protein, PatE (FIG. 1f). However, the presence of products with different sizes (octamer and hexamer) on a single precursor had not been observed in any of the 29 patellamide pathway variants previously described (Donia 2006).

Figure 1B:
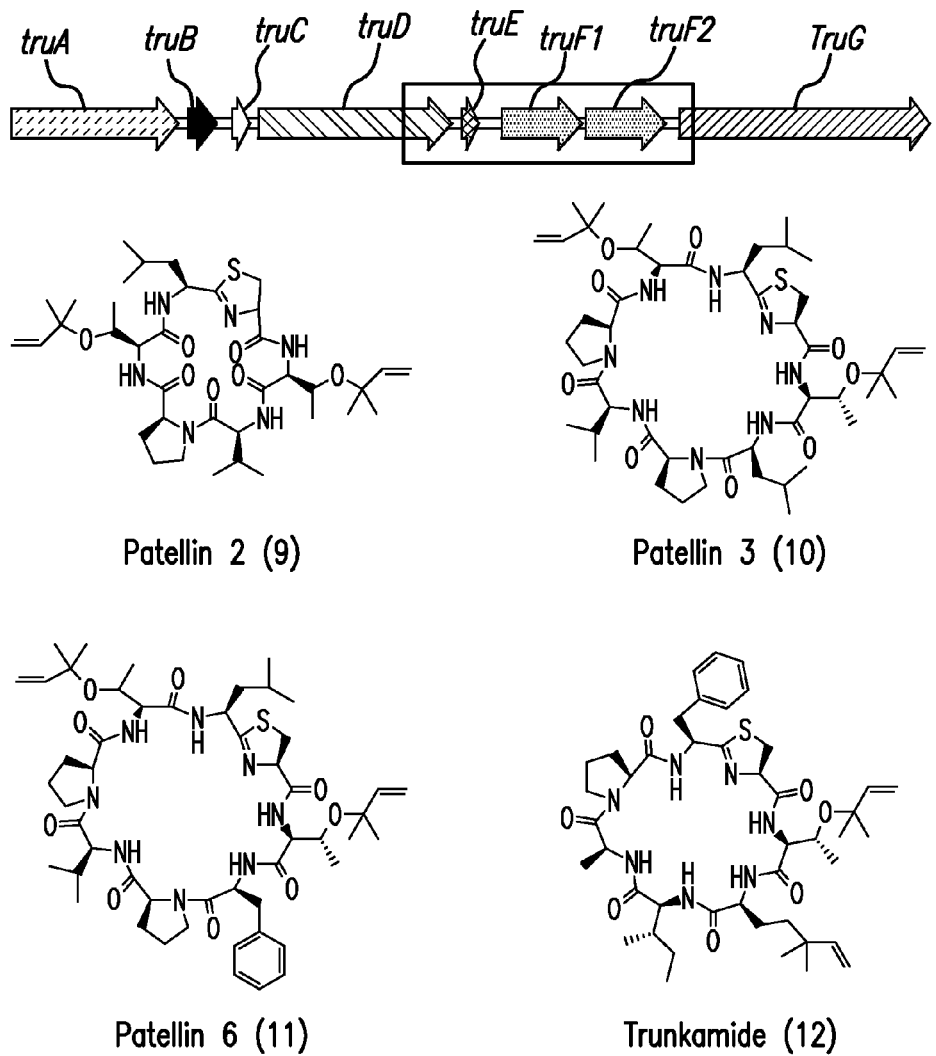

Comparative sequence analysis of the tru cluster shows that it is syntenic to pat (FIG. 1a,b). The two clusters share 98.2-99.1% DNA sequence identity over half of the pathway. A region with lower identity spans the last 980 by of truD, truE, truF1, truF2 and the first 1806 nucleotides of truG. In this 5.8 kb region (FIG. 1a,b), predicted proteins share 41-74% identity with their homolgs in the pat cluster. However, two major differences were observed that are consistent with the unique chemical features of the patellins. First, TruG does not contain an oxidase domain, unlike its patellamide homolog, PatG. This is rationalized by the fact that patellins harbor thiazolines, while patellamides are oxidized to thiazoles. Second, two copies of truF are found adjacent to each other and syntenic to the location of patF. TruF1 and TruF2 are 41 and 46% identical to PatF, respectively, but only 35% identical to each other. truD and patD are virtually identical throughout their first 1360 bps (97% identity in the DNA and the resulting amino acid sequence). However, in their last 980 bp, the genes only share 72% identity. Because the pat and tru clusters were shown to be sufficient for the biosynthesis of the patellamides and the patellins, respectively, detailed comparative analysis sheds light on the individual proteins' functional evolution. For example, the main differences between the two clusters are found in patF/(truF1-truF2) and patD/truD (3' end). It appears that at least one set of these proteins is involved in the heterocyclization of serine and threonine in the patellamides and their prenylation in the patellins.

Figure 6:
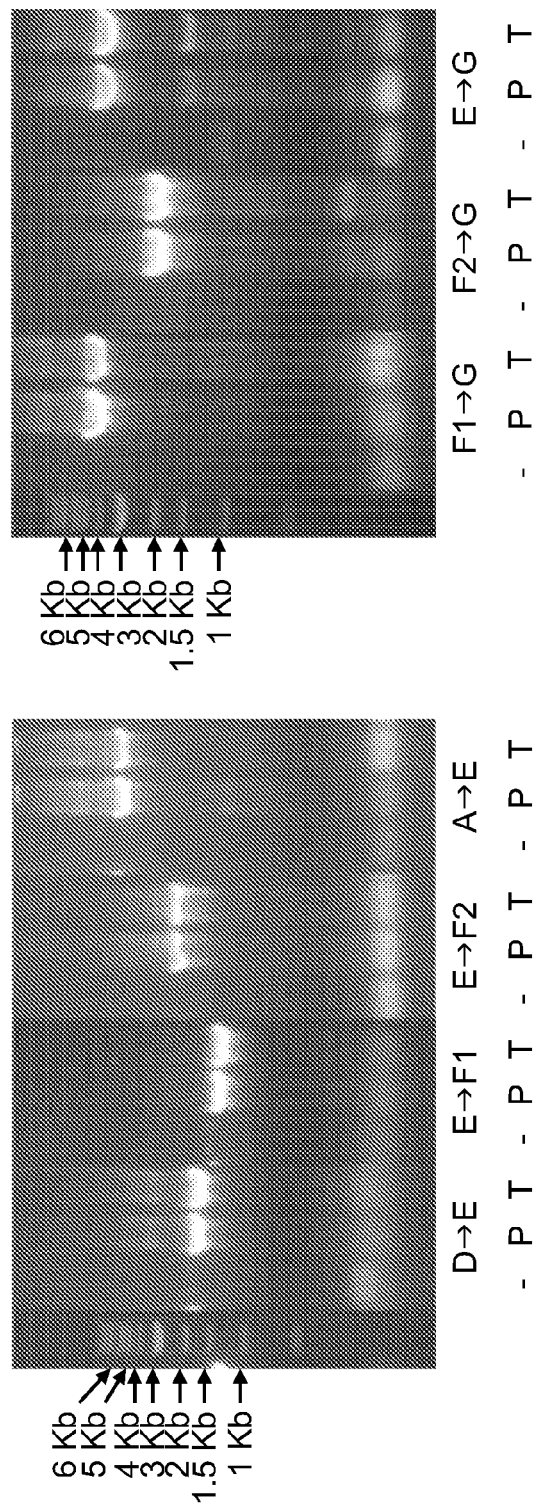
FIG. 6 shows the orientation and integrity of tru2 pathway. Gel electrophoresis of the PCR products from the PCR experiments explained in Table 4=negative control (sterile water), P=product from the patellin pathway (tru1, sample 06-037), T=product from the trunkamide pathway (tru2, sample 06-027). Letters refer to tru genes (A to G). 2-log DNA ladder is used to determine product sizes. No matter what region is examined, an exact size product is produced from both pathways.

In the patellamides, hypervariability in small cassettes in PatE lead to natural cyclic peptide libraries (Donia 2006). To see whether this is also the case for TruE, variants were cloned from ascidian samples containing patellins and trunkamide, revealing two novel genes: truE2 and truE3 (FIG. 2a). While TruE2 encodes the octapeptide patellin 6 and the heptapeptide trunkamide, TruE3 encodes 3 copies of trunkamide, representing the first PatE variant encoding more or less than 2 product peptides. PCR and sequencing experiments were used to compare the tru1 and tru2 clusters and showed that they are identical, with the exception of hypervariable cassettes in truE in the exact product-coding regions (FIG. 6). These results show that the evolution of the tru pathway mimicked that of the pat pathways. Single point mutations in short cassettes generated a library of prenylated cyclic peptides.

4. Evolution of Biosynthetic Pathways

Biosynthetic pathways to bacterial secondary metabolites are extremely complex, and an understanding of their evolution allows for the engineering of new pharmaceuticals. Symbiotic bacteria offer an ideal model to follow this evolution because relationships can be precisely defined. The evolution of the pat pathway was examined, from *Prochloron* spp. cyanobacterial symbionts of ascidians collected in the tropical Pacific. Six variants of the 70-amino acid patellamide precursor protein, PatE, were discovered from tropical Pacific *Prochloron* samples. In all cases, amino acid and DNA sequences were virtually identical except in the 16-amino acid regions encoding the actual patellamides, which had highly diverse DNA and amino acid sequences. By contrast, *Prochloron* spp. were found to be >99% identical by molecular methods. Thus, the coding sequences for patellamide biosynthesis have rapidly diversified by recombination that is unprecedented in bacterial metabolic pathways.

Bacteria living symbiotically with higher organisms provide a potential mechanism to more readily discern important events in the evolution of complex secondary metabolites. Often, bacteria-host relationships can be rigorously defined because of vertical transmission of symbionts, (Baumann, P. Annu Rev. Microbiol. 59, 155-1589 (2005)) simplifying evolutionary scenarios. In addition, the common relationship of microscopic organisms with macroscopic, chemically defined animals or plants provides a platform for the study of pathway evolution.

*Prochloron* spp. are common symbiotic cyanobacteria that are intimately associated with marine animals, especially ascidians of the Family Didemnidae (Withers et al. Phycologia 17, 167-171 (1978); Lewin et al. *Prochloron*: A Microbial Enigma (Chapman and Hall, New York, 1989)). They are also found associated with stromatolites (bacterial mat structures), but they have not yet been found outside of these structured, metabolically active environments. Numerous cyclic peptides, especially those of the patellamide class, have been isolated from didemnid ascidians, forming overlapping families of evolutionarily related metabolites. (Sings et al. Journal of Industrial Microbiology & Biotechnology 17, 385-396 (1996); Schmidt et al. J. Nat. Prod. 67, 1341-1345 (2004)).

C. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular patellamide is disclosed and discussed and a number of modifications that can be made to a number of molecules of the patellamide are discussed, specifically contemplated is each and every combination and permutation of those and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed herein are sets of recombinant proteins that catalyze the prenylation of peptides. This prenylation event does not depend upon the sequence of the prenylated peptide; rather, recognition sequences in a prepeptide surrounding the peptide of interest dictate the prenylation. Disclosed herein are various prepeptides (also referred to as recognition sequences). While the polymer, such as a peptide, to be prenylated (also referred to as the coding sequence) can vary greatly and still be prenylated, and can, in fact, be any peptide capable of being prenylated, the recognition sequence is much more specific.

As discussed above, any type of polymer, including peptides, can be prenylated using the recognition sequences disclosed herein, including organic polymers such as biopolymers that contain amino acid or nucleotide monomers, or a mixture of different types of monomers. Accordingly, polypeptides, polynucleotides, or a polymer containing both amino acid and nucleotide monomers, for example, may be prenylated using the subject methods. In many embodiments of the invention, the polymer used is a biopolymer containing amino acids, i.e., a polypeptide. Polymers that may be employed herein may not contain any peptide bonds. However, in certain embodiments, the polymers may contain peptide bonds in between the first and second monomers of one or both ends of the polymer to be prenylated.

For example, below, the sequences in bold are the recognition sequences, and the intervening underlined sequences are prenylated by the described enzymes. The combination of coding sequence and recognition sequence is referred to throughout the application as a "fusion polypeptide.":

SEQ ID NO: 54
MNKKNILPQLGQPVIRLTAGQLSSQLAELSEEALGGVDASTLPVPTLC
SYDGVDASTVPTLCSYDD

SEQ ID NO: 55
MNKKNILPQLGQPVIRLTAGQLSSQLAELSEEALGGVDASTFPVPTVC
SYDGVDASTSIAPFCSYDD

SEQ ID NO: 56
MNKKNILPQLGQPVIRLTAGQLSSQLAELSEEALGGVDASTSIAPFCS
YDGVDASTSIAPFCSYDGVDASTSIAPFCSYDD

The sequences in bold are the recognition sequences, and the intervening underlined sequences are prenylated. Disclosed herein are isolated peptides that can act as "recognition sequences", and function as prepeptides to allow for the formation of prenylated peptides. For example, disclosed herein is an isolated peptide comprising an amino acid segment comprising the amino acid sequence of SEQ ID NOS: 57 and 58 (MNKKNILPQLGQPVIRLTAGQLSSQLAELSEEAL-GGVDASN$^1$SYDGVDASN$^2$SYDD and MNKKNILPQL-GQPVIRLTAGQLSSQLAELSEEALGGVDAS N$^1$SYDG-VDASN$^2$SYDGVDASN$^3$SYDD, respectively) where N is the coding sequence and can be any length, as discussed above. For example, the coding sequence can be 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 amino acids in length, or any amount in between, for example. There are numerous examples given throughout of various peptides that can be prenylated by the recognition sequences disclosed herein.

As discussed in greater detail below, the isolated peptide can comprise an amino acid sequence at least about 90% identical to the amino acid sequence of SEQ ID NO: 57 or 58, or the amino acid sequence of SEQ ID NO: 57 or 58 can have one or more conservative amino acid substitutions.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

3. Nucleic Acids

There are a variety of molecules disclosed herein that are nucleic acid based, including for example the nucleic acids that encode, for example, patellamides and trichamide as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to, for example, patellamides and trichamides as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

c) Primers and Probes

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

4. Vectors and Fusion Polypeptides

Disclosed herein are vectors comprising a nucleotide sequence encoding a fusion polypeptide. These vectors can be used to produce a cyclized or prenylated peptide of interest, are useful with libraries and combinatorial chemistry techniques (discussed below), and are useful with in vivo systems.

For example, disclosed herein is a vector comprising, from N-terminus to C-terminus: a) a C-terminal domain comprising SEQ ID NO: 59 (GVDAS); b) a peptide; c) an N-terminal domain comprising SEQ ID NO: 60 (SYDGVDAS); wherein the fusion polypeptide is able to cyclize the peptide to produce a cyclic peptide in a mammalian cell.

Also disclosed is a vector comprising a nucleotide sequence encoding a fusion polypeptide comprising, from N-terminus to C-terminus: a) a C-terminal domain comprising SEQ ID NO: 61 (SYDD); b) a peptide; c) an N-terminal domain comprising SEQ ID NO: 60 (SYDGVDAS); wherein the fusion polypeptide is able to cyclize the peptide to produce a cyclic peptide in a cell. This cell can be prokaryotic, such as E. coli, or eukaryotic, such as a mammalian cell.

The vectors disclosed above can comprise a random peptide, which are discussed in greater detail below. The peptide of interest (the coding sequence) can be derived from a cDNA library. For example, each vector in the library can encode a different fusion polypeptide. In a further example, the peptide of interest of each different fusion polypeptide can be different. The peptide of interest can be a random peptide at least 3 amino acids in length, as discussed below.

Also disclosed is a cell comprising the vectors discussed above, or progeny thereof. This cell can be prokaryotic, or eukaryotic, such as a mammalian cell. Examples of such cells include a tumor cell, a liver cell, a hepatocyte, a mast cell and a lymphocyte cell. The cell can also be a human cell.

There are a number of compositions and methods which can be used to deliver nucleic acids, such as those encoding the prenylated peptides disclosed herein, to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as those encoding prenylated peptides, into the cell without degradation and include a promoter yielding expression of the gene in the cells into which it is delivered. In some embodiments the peptides are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Feigner et al. *Proc. Natl. Acad. Sci. USA* 84:7413-7417

(1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129: 57-80, (1992); and Roffler, et al., *Biochem. Pharmacol,* 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

5. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell. Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell. Bio.* 4: 1293 (1984)). They are usually between 10 and 300 by in length, and they function in cis. Enhancers function to increase transcription from nearby promoters.

Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

6. Peptides a) Protein Variants

As discussed herein, the coding sequence of the peptides disclosed herein can vary widely and still be prenylated. Furthermore, the recognition sequences, which must have more specificity but which can still have some degree of variance and remain functional, are also disclosed herein. For example, there are numerous variants of the coding sequences that are known and herein contemplated. In addition, to the known functional strain variants there are derivatives of the these proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by crosslinking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations
TABLE 1: Amino Acid Abbreviations

| Amino Acid | Abbreviations |
|---|---|
| alanine | Ala (A) |
| allosoleucine | AIle |
| arginine | Arg (R) |
| asparagine | Asn (N) |
| aspartic acid | Asp (D) |
| cysteine | Cys (C) |
| glutamic acid | Glu (E) |
| glutamine | Gln (K) |
| glycine | Gly (G) |
| histidine | His (H) |
| isolelucine | Ile (I) |
| leucine | Leu (L) |
| lysine | Lys (K) |
| phenylalanine | Phe (F) |
| proline | Pro (P) |
| pyroglutamic acid | PGlu |
| serine | Ser (S} |
| threonine | Thr (T) |
| tyrosine | Tyr (Y) |
| tryptophan | Trp (W) |
| valine | Val (V_ |

TABLE 2

Amino Acid Substitutions
Original Residue Exemplary Conservative Substitutions, others are known in the art.

Ala; ser
Arg; lys, gln
Asn; gln; his
Asp; glu
Cys; ser
Gln; asn, lys
Glu; asp
Gly; pro
His; asn; gln
Ile; leu; val
Leu; ile; val
Lys; arg; gln
Met; leu; ile
Phe; met; leu; tyr
Ser; thr
Thr; ser
Trp; tyr
Tyr; trp; phe
Val; ile; leu Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences.

Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is understood that while no amino acid sequence indicates what particular DNA sequence encodes that protein within an organism, where particular variants of a disclosed protein are disclosed herein, the known nucleic acid sequence that encodes that protein in the particular sequence from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH$=$CH$— (cis and trans), —$COCH_2$—$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CH H_2$—S); Hann J. Chem. Soc Perkin Trans. 1307-314 (1982) (—$CH$—$CH$—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—$CH(OH)CH_2$—); Holladay et al. Tetrahedron. Lett 24:4401-4404 (1983) (—$C(OH)CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

7. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pieterz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including prenylated peptides, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

The disclosed compositions and methods can also be used for example as tools to isolate and test new drug candidates for a variety of diseases.

8. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

9. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein.

10. Compositions Identified by Screening with Disclosed Compositions/Combinatorial Chemistry a) Combinatorial Chemistry/Libraries The prenylated of the invention can comprise random peptides. By "random peptides" herein is meant that each peptide consists of essentially random amino acids. Since generally these random peptides (or nucleic acids, discussed below) are chemically synthesized, they may incorporate any amino acid at any position. The synthetic process can be designed to generate randomized proteins to allow the formation of all or most of the possible combinations over the length of the sequence, thus forming a library of randomized peptides.

This invention provides libraries of prenylated polypeptides. By "library" herein is meant a sufficiently structurally diverse population of randomized expression products to effect a probabilistically sufficient range of cellular responses to provide one or more cells exhibiting a desired response. Accordingly, an interaction library must be large enough so that at least one of its members will have a structure that gives it affinity for some molecule, protein, or other factor whose activity is of interest. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$-$10^8$ is sufficient to find structures with affinity for the target. A library of all combinations of a peptide 7 to 20 amino acids in length, such as proposed here for expression in retroviruses, has the potential to code for $20^7$ ($10^9$) to $20^{20}$. Thus, with libraries of $10^7$-$10^8$ per ml of retroviral particles the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different expression products are simultaneously analyzed in the subject methods. Preferred methods maximize library size and diversity.

In a preferred embodiment, libraries of all combinations of a peptide 3 to 30 amino acids in length are synthesized and analyzed as outlined herein. Libraries of smaller prenylated peptides, i.e., 3 to 4 amino acid in length, are advantageous because they are more constrained and thus there is a better chance that these libraries possess desirable pharmocokinetics properties as a consequence of their smaller size. Accordingly, the libraries of the present invention may be one of any of the following lengths: 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids, 25 amino acids, 26 amino acids, 27 amino acids, 28 amino acids, 29 amino acids and 30 amino acids in length.

The invention further provides fusion nucleic acids encoding the fusion polypeptides of the invention. As will be appreciated by those in the art, due to the degeneracy of the genetic code, an extremely large number of nucleic acids may be made, all of which encode the fusion proteins of the present invention. Thus, having identified a particular amino acid sequence, those skilled in the art could make any number of different nucleic acids, by simply modifying the sequence of one or more codons in a way which does not change the amino acid sequence of the fusion protein.

Using the nucleic acids of the present invention which encode a fusion protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the fusion protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The fusion nucleic acids are introduced into cells to screen for prenylated peptides capable of altering the phenotype of a cell. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include liposome fusion, Lipofectin®, electroporation, viral infection, etc. The fusion nucleic acids may stably integrate into the genome of the host cell, or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

The fusion nucleic acids can be part of a retroviral particle which infects the cells, as described above. Generally, infection of the cells is straightforward with the application of the infection-enhancing reagent polybrene, which is a polycation that facilitates viral binding to the target cell. Infection can be optimized such that each cell generally expresses a single construct, using the ratio of virus particles to number of cells. Infection follows a Poisson distribution.

The fusion nucleic acids can be introduced into cells using retroviral vectors. This is described in more detail above, however, is reviewed briefly again. Currently, the most efficient gene transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153-159 (1993), hereby incorporated by reference). Such helper-defective packaging lines are capable of producing all the necessary trans proteins—gag, pol, and env—that are required for packaging, processing, reverse transcription, and integration of recombinant genomes. Those RNA molecules that have in cis the psi packaging signal are packaged into maturing virions. Retroviruses are preferred for a number of reasons. First, their derivation is easy. Second, unlike Adenovirus-mediated gene delivery, expression from retroviruses is long-term (adenoviruses do not integrate). Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express.

A particularly well suited retroviral transfection system is described in Mann et al, supra: Pear et al., PNAS USA 90(18): 8392-6 (1993); Kitamura et al., PNAS USA 92:9146-9150 (1995); Kinsella et al., Human Gene Therapy 7:1405-1413; Hofmann et al., PNAS USA 93:5185-5190; Choate et al., Human Gene Therapy 7:2247 (1996); and WO 94/19478; and references cited therein, all of which are incorporated by reference.

The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed herein, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function.

It is understood that the disclosed methods for identifying molecules can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, TIBS 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94 (23) 12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptidyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94 (23) 12997-302 (1997)).

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, Nature 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example an extracellular portion, is attached to a DNA binding domain of a transcriptional activation protein, such as Gal 4. By performing the Two-hybrid technique on this type of system, molecules that bind the extracellular portion can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in interative processes.

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions are also disclosed. Thus, the products produced using the molecular modeling approaches that involve the disclosed compositions, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

11. Kits

Disclosed herein are kits that are drawn to reagents that can be used in practicing the methods disclosed herein. For example, the kits can comprise reagents for generating libraries of prenylated peptides. The kits can include any reagent or combination of reagent discussed herein or that would be understood to be required or beneficial in the practice of the disclosed methods. For example, the kits could include the recognition sequences, such as those found in SEQ ID NOS: 54-58, as well as the buffers and enzymes required to use the sequences as intended.

12. Compositions with Similar Functions

It is understood that the compositions disclosed herein have certain functions, such as prenylated peptides. Disclosed herein are certain structural requirements for performing the disclosed functions, and it is understood that there are a variety of structures which can perform the same function which are related to the disclosed structures, and that these structures will ultimately achieve the same result, for example prenylation. These compositions are also contemplated herein.

D. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used in vectors can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed peptides, such as SEQ ID NO: 1, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Process Claims for Making the Compositions

Disclosed are processes for making the compositions as well as making the intermediates leading to the compositions. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth herein and a sequence controlling the expression of the nucleic acid.

Also disclosed are nucleic acid molecules produced by the process comprising linking in an operative way a nucleic acid molecule comprising a sequence having 80% identity to the given sequence, and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth herein and a sequence controlling the expression of the nucleic acid.

Disclosed are nucleic acid molecules produced by the process comprising linking in an operative way a nucleic acid molecule comprising a sequence encoding a peptide set forth herein and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

E. Methods of Using the Compositions

1. Methods of Using the Compositions as Research Tools

The disclosed compositions can be used in a variety of ways as research tools. For example, the disclosed polypeptide sequences can be used to identify compositions useful as pharmaceuticals.

For example, disclosed herein are methods for prenylating a polypeptide comprising inserting the polypeptide to be prenylated in the coding region of a fusion polypeptide. For example, SEQ ID NO: 57 or 58, shows two or three "N" regions, $N^1$-$N^3$. Into any, or all three, of these regions can be inserted a coding sequence, such as a sequence encoding a peptide to by prenylated. The entire sequence is known as a fusion polypeptide.

Although the coding region is often referred to herein as a peptide, it can be any polymer capable of being prenylated. It is known in the art that any type of polymer can be prenylated using the methods disclosed herein, including organic polymers such as biopolymers that contain amino acid or nucleotide monomers, or a mixture of different types of monomers. Accordingly, polypeptides, polynucleotides, or a polymer containing both amino acid and nucleotide monomers, for example, may be prenylated using the subject methods. In many embodiments of the invention, the polymer used is a biopolymer containing amino acids, i.e., a polypeptide. Polymers that may be employed in the subject methods may not contain any peptide bonds. However, in certain embodiments, the polymers may contain peptide bonds in between the first and second monomers of one or both ends of the polymer to be prenylated.

A polymer of interest may be at least 2, 3, 4, 5, 6, 7, 8, 9, 10, 11 or 12 monomers, or more than 12 monomers in length, usually up to about 20, 30, 40, 50 or 100 or 1000 or more monomers in length. Accordingly, a peptide employed in the subject methods may contain at least 2, 3, 4, 5, 6, 7, 8, 9, 10, 11 or 12 amino acids, or more than 12 amino acids, usually up to about 20, 30, 40 or 50 amino acids (e.g., non-naturally occurring amino acids, naturally occurring amino acids or a mixture thereof). Polymers of particular interest are 2-50, 3-40, 4-30, 3-8, 5-20 or 6-10 monomers in length, and typically range from 500-5000 Da, 600-4000 Da, 700-2000 Da in molecular weight.

The compositions can be used for example as targets in combinatorial chemistry protocols or other screening protocols to isolate molecules that possess desired functional properties, as discussed above.

The disclosed compositions can also be used diagnostic tools related to diseases. The disclosed compositions can be used as discussed herein as either reagents in micro arrays or as reagents to probe or analyze existing microarrays. The disclosed compositions can be used in any known method for isolating or identifying single nucleotide polymorphisms.

The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

Disclosed herein is a method for diagnosing a disease in a subject, the method comprising: obtaining a sample from the subject, contacting the sample with a prenylated peptide library, wherein the prenylated peptide library is specific for the disease; identifying interaction between the sample and the prenylated peptide library, wherein such interaction indicates diagnosis of the disease. The disease can be cancer, or can be an infectious disease, such as that caused by a virus, fungi, or bacteria.

The sample which is contacted with the prenylated peptides can be a from any biological fluid or mass, such as sera, blood, sputum, or tissue culture. In one example, the sample is from a tumor. The diagnostic assay can comprise the recognition of an antibody, which would indicate the presence of a given disease or disorder. For example, an antibody which is associated with a given disease or disorder can interact with the prenylated peptide library, thereby indicating that a diseased state is present in the subject from which the sample was obtained.

Identification of one or more markers for the prognosis, diagnosis, and detection of disease has been described previously. Suitable methods for identifying such diagnostic, prognostic, or disease-detecting markers are described in detail in U.S. Pat. No. 6,658,396, U.S. patent application Ser. No. 09/611,220, and U.S. provisional patent application Ser. No. 10/948,834, each of which patents and parent applications is hereby incorporated by reference in its entirety, including all tables, figures, and claims. These general methods of prognosing and diagnosing disease can be used with the methods disclosed herein.

a) Hormone Receptors

Estrogen binds to and mediates homodimerization of estrogen receptor alpha (ESR1/ER). The activated ERs can then bind to a variety of coactivators or corepressors and modulate transcription of various genes through promoter interactions, thereby stimulating growth. Tamoxifen inhibits this activity by competing with estrogen for binding to the ERs and modifying their transcriptional regulation activity [C K Osborne, et al. Breast 12:362]. The presence of ER is currently the primary predictor of tamoxifen treatment response. Some studies indicate that the higher the level of this marker, the greater the benefit of the treatment [Lancet 351:1451; L E Rutqvist, et al. J Clin Oncol 7:1474].

Progesterone receptor (PGR) is an estrogen-regulated gene product [B M Arafah, et al. Endocrinology 111:584]. Thus, the presence of PGR may be a surrogate indicator of a functional estrogen response pathway. This could provide predictive information in cases where ER is present at functional levels that are too low to detect (false negative), or where ER is detected but is a non-functional mutant or variant (false positive) [V J Bardou, et al. J Clin Oncol 21:1973; C K Osborne. N Engl Med 339:1609]. Alternatively, PGR negativity may result from signaling through EGFR/ERBB2 or IGF-R [X Cui, et al. Mol Endocrinol 17:575; M Dowsett, et al. Cancer Res 61:8452]. Several studies have demonstrated independent significance of PGR levels [V J Bardou, et al. J Clin Oncol 21:1973; M J Ellis, et al. J Clin Oncol 19:3808; M Ferno, et al. Breast Cancer Res Treat 59:69], although others have not [Lancet 351:1451], potentially based on limitations in the PGR assay.

b) ERBB Growth Factor Receptors and Interactors

It is now widely recommended that ERBB2 (HER2/neu) levels be assessed in breast cancer, as this marker helps predict treatment response to trastuzumab. It also may help predict response to anthracycline-based cytotoxic therapies [R C Bast, Jr., et al. J Clin Oncol 19:1865]. In addition, there is emerging evidence that both ERBB2 and its family member EGFR (HER1/ERBB1) may help predict response to tamoxifen. A majority of clinical studies have shown an association between the presence of elevated EGFR or ERBB2 in ER-/PGR-positive tumors and resistance to endocrine therapies (particularly tamoxifen), although not all studies agree [M Piccart, et al. Oncology 61 Suppl 2:73; S De Placido, et al. Clin Cancer Res 9:1039; R K Gregory, et al. Breast Cancer Res Treat 59:171; A Makris, et al. Clin Cancer Res 3:593; A E Pinto, et al. Ann Oncol 12:525; J G Klijn, et al. Endocr Rev 13:3; G Arpino, et al. Clin Cancer Res 10:5670; M J Ellis, et al. J Clin Oncol 19:3808; S J Houston, et al. Br J Cancer 79:1220; C Wright, et al. Br J Cancer 65:118; S Sjogren, et al. J Clin Oncol 16:462].

ERBB2 and EGFR are growth factor receptor tyrosine kinases that initiate cell survival and proliferation signaling cascades. In the presence of the appropriate peptide growth factors, activation of these pathways may overcome the growth inhibitory effects of tamoxifen on the ER pathway. In addition, there is substantial crosstalk between the ER pathway and the ERBB2 and EGFR growth factor pathways [C K Osborne, et al. Breast 12:362]. For example, there is evidence that various downstream members in these pathways (e.g., ERK 1,2 and AKT) can directly activate ER. Reciprocally, there is evidence that ER can directly activate members of the ERBB2 and EGFR pathways [M P Haynes, et al. J Biol Chem 278:2118; E R Levin. Mol Endocrinol 17:309; M Razandi, et al. J Biol Chem 278:2701]. Interestingly, binding of ER by either estrogen or tamoxifen may be sufficient for this activation. In fact, a preclinical study indicates that tamoxifen can actually stimulate cell proliferation in ERBB2-positive breast cancer cells, shifting tamoxifen from an antagonist to an agonist role [J Shou, et al. J Natl Cancer Inst 96:926]. Consistent with this finding, a clinical study found that ERBB2-positive patients given tamoxifen had higher rates of recurrence than untreated patients [C Carlomagno, et al. J Clin Oncol 14:2702; S De Placido, et al. Clin Cancer Res 9:1039]. Clinical trials showing that aromatase inhibitors are more effective than tamoxifen in ERBB2-positive cancers further supports this model [M J Ellis, et al. J Clin Oncol 19:3808; I E Smith, et al. J Clin Oncol 23]. It has been suggested that ER/PGR-positive patients with elevated EGFR and/or ERBB2 should be treated simultaneously with a combination of tamoxifen and inhibitors of the growth factor receptor pathways (e.g., trastuzumab for ERBB2, gefitinib for EGFR, or the dual inhibitor GW572016).

ERBB2 levels are typically determined by either fluorescence in situ hybridization (FISH) or IHC, but the reliability and concordance of these assays is highly variable [M Bilous, et al. Mod Pathol 16:173]. While FISH seems to be a better predictor of response to trastuzumab, gene amplification may not always correlate with protein level or localization, so IHC may prove to be superior. Elevated ERBB2 is evident in approximately 25% of primary breast cancers [M D Pegram, et al. Breast Cancer Res Treat 52:65]. Levels of ER and ERBB2 tend to be inversely related, so when ER is present in ERBB2-positive tumors, it is frequently relatively low.

Family members ERBB3 and ERBB4 may also contribute to growth of breast cancer cells and can contribute to patient prognosis, particularly when assessed in combination with all family members [D M Abd El-Rehim, et al. Br J Cancer 91:1532].

NRG1 (neuregulin alpha) and NRG2 (neuregulin beta) interact with ERBB receptors and can induce growth and differentiation of epithelial and other cell types [D L Falls. Exp Cell Res 284:14].

c) General Tumor Suppressors and Oncogenes

Inactivation of tumor suppressors and activation of oncogenes are frequent events during tumorigenesis. In response to various cellular stresses, the tumor suppressor TP-53 can induce growth arrest or apoptosis through either transcription-dependent or -independent mechanisms. Tamoxifen may activate TP-53 and apoptosis by directly inducing DNA damage [S Shibutani, et al. Carcinogenesis 19:2007; P A Ellis, et al. Int J Cancer 72:608]. Tamoxifen may also activate the anti-proliferative transforming growth factor beta pathway and decrease plasma insulin-like growth factor I levels. Mutant TP-53 can interfere with these, and other, pathways [E M Berns, et al. J Clin Oncol 16:121]. Mutations in TP-53, most of which lead to elevated basal levels of the protein, are observed in 25-30% of breast cancers. Most studies show that mutant TP-53 is associated with resistance to endocrine therapies, including tamoxifen [J Bergh, et al. Nat Med 1:1029; E M Berns, et al. Cancer Res 60:2155; R Silvestrini, et al. J Clin Oncol 14:1604; E M Berns, et al. Clin Cancer Res 9:1253; E M Berns, et al. J Clin Oncol 16:121; H B Burke, et al. Cancer 82:874; P D Pharoah, et al. Br J Cancer 80:1968]. Other studies show no association [S G Archer, et al. Br J Cancer 72:1259; R M Elledge, et al. J Clin Oncol 15:1916]. However, this may be due to different techniques of determining TP-53 status, different subsets of patients studied, or complex interactions with other markers. Although mutations that lead to loss of TP-53 function are well-characterized, there is also evidence that some TP-53 mutants exert gain-of-function effects. Such mutants have altered transcriptional activities and/or protein binding targets, favoring growth and/or apoptosis resistance.

The FHIT tumor suppressor is involved in regulation of cell growth and may be a prognostic factor in breast cancer [S Ingvarsson. Semin Cancer Biol 11:361]. PARK2 (parkin) is a putative tumor suppressor in breast cancer due to the frequency of loss of heterozygosity [R Cesari, et al. Proc Natl Acad Sci USA 100:5956]. The hepatocyte growth factor receptor (MET oncogene) is an independent prognostic factor in breast cancer [R A Ghoussoub, et al. Cancer 82:1513]. Then amplified, the MYC oncogene can inappropriately stimulate cell division through its functions in metabolism, replication, differentiation, and apoptosis [S L Deming, et al. Br J Cancer 83:1688].

Several studies indicate that a low BCL2 level is associated with worse outcome in tamoxifen-treated breast cancers [M G Daidone, et al. Br J Cancer 82:270; M McCallum, et al. Br J Cancer 90:1933; Q Yang, et al. Oncol Rep 10:121; R M Elledge, et al. J Clin Oncol 15:1916; G Gasparini, et al. Clin Cancer Res 1:189; R Silvestrini, et al. J Clin Oncol 14:1604]. This is counter-intuitive, as BCL2 is an anti-apoptotic factor that might be expected to inhibit drug-induced apoptosis in the tumor cells. However, there is evidence that, similar to PGR, the BCL2 gene itself is ER-regulated. Thus, high BCL2 may be indicative of an intact ER pathway that is driving tumor growth and should be sensitive to endocrine therapy [B Perillo, et al. Mol Cell Biol 20:2890]. In addition, BCL2 may predict tamoxifen treatment outcome, because, in those tumors in which it is highly expressed, it may be the leading anti-apoptotic factor, and tamoxifen would be expected to block its expression. Alternatively, it has been proposed that BCL2 may be a surrogate marker for other biological processes that occur during tamoxifen treatment and/or that higher levels of BCL2 may be indicative of more indolent, differentiated tumors [M G Daidone, et al. Br J Cancer 82:270; R M Elledge, et al. J Clin Oncol 15:1916].

d) Membrane/Adhesion Factors

A number of membrane proteins are involved in adhesion and/or cell signaling pathways, and alterations in the expression of these proteins may increase invasive capability and/or growth signaling during tumorigenesis. CAV1 (caveolin) is a plasma membrane protein that has been implicated as a tumor suppressor involved in the modulation of integrin-related cell signaling through the Ras-ERK pathway, and it may play roles in inhibiting invasion and metastasis [E K Sloan, et al. Oncogene 23:7893]. MLLT4 (AF-6/afadin) is involved in the organization of epithelial cell junctions, including E-cadherin-based adherens and claudin-based tight junctions [Y Takai, et al. J Cell Sci 116:17]. MME (CD10) is a transmembrane glycoprotein neutral endopeptidase, and its expression in stromal cells may have prognostic relevance in breast cancer [K Iwaya, et al. Virchows Arch 440:589]. MSN (moesin) is in a family of proteins that includes ezrin and radixin (ERMs) that link plasma membranes with actin filaments, it is likely involved in cell adhesion and motility and may play a role in tumorigenesis [A I McClatchey. Nat Rev Cancer 3:877]. Overexpression of MUC1 may interfere with cell adhesion and protect tumor cells from recognition by the immune system [S von Mensdorff-Pouilly, et al. Int J Biol Markers 15:343].

e) Angiogenesis Factors

Growth of primary tumors, as well as metastases, relies in part on formation of new blood vessels adjacent to the cancer cells. VEGF (vascular endothelial growth factor) acts on endothelial cells to induce vascular permeability, angiogenesis, vasculogenesis, and cell growth, thereby promoting cell migration and inhibiting apoptosis. It has been implicated in the progression of and prognosis of several cancer types, including breast [D Coradini, et al. Br J Cancer 89:268]. Basic fibroblast growth factor (FGF2) and its receptor (FGFR1) have been implicated in cancer-associated angiogenesis [A Bikfalvi, et al. Angiogenesis 1:155]. ANGPT1 (angiopoietin) is also involved in the promotion of angiogenesis, and its levels have been associated with breast cancer prognosis [A J Hayes, et al. Br J Cancer 83:1154]. In contrast, THBS1 (thrombospondin) is an anti-angiogenic factor.

f) Cell Cycle/Proliferation Markers

Cyclin protein levels rise and fall during the cell cycle. CCND1 (cyclin D1) and CCNE1 (cyclin E) levels increase during late G1 phase and mediate the G1-S phase transition through binding and regulation of cyclin-dependent kinases, such as CDK2, CDK4, and CDK6. Cyclin overexpression is observed frequently in breast cancer, and there is evidence that they are prognostic factors [H Kuhling, et al. J Pathol 199:424; Y Umekita, et al. Int J Cancer 98:415]. CDKN1B (p27/Kip1) is an inhibitor of CCNE1-CDK2 and cyclin CCND1-CDK4 complexes, preventing cell cycle progression in G1 [A Alkarain, et al. Breast Cancer Res 6:13].

MKI67 (MIB1/Ki-67) is a nuclear protein that is only expressed in cells progressing through the cell cycle. As such, it is used as a proliferation marker, and numerous studies show that it can be used to stratify breast cancer patients into good (low staining) and poor (high staining) prognostic categories [P L Fitzgibbons, et al. Arch Pathol Lab Med 124: 966].

g) Catenin-Based Invasion/Metastasis Factors

Cadherin-catenin complexes perform important roles in cell adhesion, loss of which can contribute to tumor invasion and metastasis [I R Beavon. Eur J Cancer 36:1607]. Cadherins (CDHs) are transmembrane proteins directly involved in cell adhesion through their extracellular domains. Loss of expression of CDH1 (epithelial-cadherin) or gain of expression of CDH3 (placental-cadherin) are indicative of a basal phenotype with a worse prognosis. Catenins (CTNNs) bind to the intracellular domains of cadherins and mediate growth signaling to the nucleus. Aberrant accumulation of catenins like CTNNA1 (alpha-catenin) or CTNNB1 (beta-catenin) can be associated with poor prognosis.

SCRIB (the human homolog of *Drosophila* scribbled) is recruited to cell-cell junctions in an E-cadherin-dependent manner and is differentially expressed in different histological types of breast cancer [C Navarro, et al. Oncogene 24:4330].

h) Other Invasion/Metastasis Factors

Degradation of the extracellular matrix by proteases is a critical step for both local invasion and establishment of metastases during cancer progression. MMP9 is a member of a large family of matrix metalloproteinases (MMPs) and PLAU (UPA) is a serine protease that are capable of degrading extracellular matrix, and the levels of these proteins may be prognostic in breast cancer patients [J M Pellikainen, et al. Clin Cancer Res 10:7621; F Janicke, et al. Lancet 2:1049]. TIMP1 is an inhibitor of matrix metalloproteinases that is also prognostic in breast cancer [A S Schrohl, et al. Clin Cancer Res 10:2289]. CTSD (cathepsin D) is an estrogen-induced lysosomal protease that may also impact degradation and be prognostic in breast cancer [A K Tandon, et al. N Engl J Med 322:297]. CD44 is a cell-surface glycoprotein involved in cell-cell interactions, cell adhesion and migration that also interacts with MMPs, and it has been implicated in tumor metastasis and breast cancer prognosis [L K Diaz, et al. Clin Cancer Res 11:3309].

MTA1 (metastasis associated 1) was identified as an over-expressed gene in a metastatic breast cancer cell screen, MTA1 may regulate transcription, including ER-mediated transcription [A Mazumdar, et al. Nat Cell Biol 3:30]. NME1 (NM23) was identified as an under-expressed gene in metastatic cells that is in a region that undergoes high-frequency loss of heterozygosity in breast cancer [C S Cropp, et al. J Natl Cancer Inst 86:1167]. S100 is a calcium-binding factor implicated in tumor metastasis.

i) Cytoskeletal/Differentiation Factors

Gene expression microarray analysis of breast cancers has revealed multiple tumor classes, including the luminal and basal classes. The basal class, which tends to have a worse prognosis, is so-named because of similarities in the expression patterns with basal epithelial cells elsewhere in the body, particularly the expression of several cytoskeletal factors. Cytokeratins are a family of intermediate filament structural proteins. Some, such as basal KRT5, KRT6, and KRT17, are normally expressed only in basal epithelial cells, and their presence has been associated with worse prognosis in breast cancer [C M Perou, et al. Nature 406:747]. Others, such as glandular KRT8, KRT18, and KRT19, are typically expressed in normal luminal epithelial cells, and their absence, as well as the absence of smooth muscle actin (ACTC/SMA), has been associated with worse prognosis in breast cancer [W Bocker, et al. Lab Invest 82:737]. These changes are also considered by some to represent an epithelial-mesenchymal or cancer stem cell transition. VIM (vimentin) is an intermediate filament also specific to mesenchymal tissue that can be activated by the catenin pathway [C Gilles, et al. Cancer Res 63:2658].

j) Transcription Factors

GATA3 is a transcriptional activator that is highly expressed in luminal breast epithelium, and its down-regulation is an indicator of worse prognosis [R Mehra, et al. Cancer Res 65:11259]. GATA4 is a related transcription factor that has been implicated in ERBB receptor-based signaling [F Bertucci, et al. Oncogene 23:2564]. HIF1A (hypoxia-inducible factor-1) is a transcription factor that is elevated under the reduced oxygen tension that occurs in tumors, and this has been associated with poor prognosis in breast cancer patients [R Bos, et al. Cancer 97:1573].

k) Centrosomal Proteins

Cells must accurately segregate their duplicated chromosomes at cell division in order to maintain normal ploidy. This requires precise formation of microtubule-based spindles at two poles, which is organized by structures called centrosomes. Disruption of this process has been associated with tumorigenesis, and alterations in expression of the involved proteins has been correlated with tumor grade. AURKA (aurora kinase A) localizes to centrosomes and is involved in microtubule formation and/or stabilization at the spindle pole during chromosome segregation. AURKB (aurora kinase B) localizes directly to the microtubules near the kinetochores.

Transforming acidic coiled-coil proteins (TACCs) are a family of proteins that interact with centrosome- and microtubule-interacting proteins, and they have been implicated in breast tumorigenesis and prognosis, as well as other cancers [F Gergely. Bioessays 24:915]. TACC1 is associated with AURKB during cytokinesis and is amplified in some breast cancers. TACC2 is induced by erythropoietin and localizes to centrosomes throughout the cell cycle. TACC3 is associated with AURKA and may be involved in microtubule assembly.

l) Other Markers

ABCG2 (BCRP; breast cancer resistance protein) is a membrane-associated protein in the White subfamily of ATP-binding cassette (ABC) transporters that functions as a xenobiotic transporter which may be involved in mitoxantrone and anthracycline resistance [A Ahmed-Belkacem, et al. Anticancer Drugs 17:239].

PTGS2 (COX2; cyclooxygenase 2) is induced by inflammation and hormonal signaling in solid tumors, and it may play roles in angiogenesis, invasion, metastasis, and/or hormone therapy resistance [C Denkert, et al. Clin Breast Cancer 4:428].

m) Method for Defining Panels of Markers

In practice, data may be obtained from a group of subjects. The subjects may be patients who have been tested for the presence or level of certain polypeptides and/or clinicopathological variables (hereafter 'markers' or 'biomarkers'). Such markers and methods of patient extraction are well known to those skilled in the art. A particular set of markers may be relevant to a particular condition or disease. The method is not dependent on the actual markers. The markers discussed in this document are included only for illustration and are not intended to limit the scope of the invention. Examples of such markers and panels of markers are described above in the instant invention and the incorporated references.

Well-known to one of ordinary skill in the art is the collection of patient samples. A preferred embodiment of the instant invention is that the samples come from two or more different sets of patients, one a disease group of interest and the other(s) a control group, which may be healthy or diseased in a different indication than the disease group of interest. For instance, one might want to look at the difference in markers between patients who have had endocrine therapy and had a recurrence of cancer within a certain time period and those who had endocrine therapy and did not have recurrence of cancer within the same time period to differentiate between the two populations.

When obtaining tumor samples for testing according to the present invention, it is generally preferred that the samples represent or reflect characteristics of a population of patients or samples. It may also be useful to handle and process the samples under conditions and according to techniques common to clinical laboratories. Although the present invention is not intended to be limited to the strategies used for processing tumor samples, we note that, in the field of pathology, it is often common to fix samples in buffered formalin, and then to dehydrate them by immersion in increasing concentrations of ethanol followed by xylene. Samples are then embedded into paraffin, which is then molded into a "paraffin block" that is a standard intermediate in histologic processing of tissue samples. The present inventors have found that many useful antibodies to biomarkers discussed herein display comparable binding regardless of the method of preparation of tumor samples; those of ordinary skill in the art can readily adjust observations to account for differences in preparation procedure.

In preferred embodiments of the invention, large numbers of tissue samples are analyzed simultaneously. In some embodiments, a tissue array is prepared. Tissue arrays may be constructed according to a variety of techniques. According to one procedure, a commercially-available mechanical device (e.g., the manual tissue arrayer MTA1 from Beecher Instruments of Sun Prairie, Wis.) is used to remove an 0.6-micron-diameter, full thickness "core" from a paraffin block (the donor block) prepared from each patient, and to insert the core into a separate paraffin block (the recipient block) in a designated location on a grid. In preferred embodiments, cores from as many as about 400 patients can be inserted into a single recipient block; preferably, core-to-core spacing is approximately 1 mm. The resulting tissue array may be processed into thin sections for staining with interaction partners according to standard methods applicable to paraffin embedded material. Depending upon the thickness of the donor blocks, as well as the dimensions of the clinical material, a single tissue array can yield about 50-150 slides containing>75% relevant tumor material for assessment with interaction partners. Construction of two or more parallel tissue arrays of cores from the same cohort of patient samples can provide relevant tumor material from the same set of patients in duplicate or more. Of course, in some cases, additional samples will be present in one array and not another.

The tumor test samples are assayed by one or more techniques, well-known for those versed in ordinary skill in the art for various polypeptide levels. Briefly, assays are conducted by binding a certain substance with a detectable label to the antibody of the protein in question to be assayed and bringing such in contact with the tumor sample to be assayed. Any available technique may be used to detect binding between an interaction partner and a tumour sample. One powerful and commonly used technique is to have a detectable label associated (directly or indirectly) with the antibody. For example, commonly-used labels that often are associated with antibodies used in binding studies include fluorochromes, enzymes, gold, iodine, etc. Tissue staining by bound interaction partners is then assessed, preferably by a trained pathologist or cytotechnologist. For example, a scoring system may be utilised to designate whether the antibody to the polypeptide does or does not bind to (e.g., stain) the sample, whether it stains the sample strongly or weakly and/or whether useful information could not be obtained (e.g., because the sample was lost, there was no tumor in the sample or the result was otherwise ambiguous). Those of ordinary skill in the art will recognise that the precise characteristics of the scoring system are not critical to the invention. For example, staining may be assessed qualitatively or quantitatively; more or less subtle gradations of staining may be defined; etc.

It is to be understood that the present invention is not limited to using antibodies or antibody fragments as interaction partners of inventive tumour markers. In particular, the present invention also encompasses the use of synthetic interaction partners that mimic the functions of antibodies. Several approaches to designing and/or identifying antibody mimics have been proposed and demonstrated (e.g., see the reviews by Hsieh-Wilson et al., Acc. Chem. Res. 29:164, 2000 and Peczuh and Hamilton, Chem. Rev. 100:2479, 2000). For example, small molecules that bind protein surfaces in a fashion similar to that of natural proteins have been identified by screening synthetic libraries of small molecules or natural product isolates (e.g., see Gallop et al., J. Med. Chem. 37:1233, 1994; Gordon et al., J. Med. Chem. 37:1385, 1994; DeWitt et al., Proc. Natl. Acad. Sci. U.S.A. 90:6909, 1993; Bunin et al., Proc. Natl. Acad. Sci. U.S.A. 91:4708, 1994; Virgilio and Ellman, J. Am. Chem. Soc. 116:11580, 1994; Wang et al., J. Med. Chem. 38:2995, 1995; and Kick and Ellman, J. Med. Chem. 38:1427, 1995). Similarly, combinatorial approaches have been successfully applied to screen libraries of peptides and polypeptides for their ability to bind a range of proteins (e.g., see Cull et al., Proc. Natl. Acad. Sci. U.S.A. 89:1865, 1992; Mattheakis et al., Proc. Natl. Acad. Sci. U.S.A. 91:9022, 1994; Scott and Smith, Science 249:386, 1990; Devlin et al., Science 249:404, 1990; Corey et al., Gene 128:129, 1993; Bray et al., Tetrahedron Lett. 31:5811, 1990; Fodor et al., Science 251:767, 1991; Houghten et al., Nature 354:84, 1991; Lam et al., Nature 354:82, 1991; Blake and Litzi-Davis, Bioconjugate Chem. 3:510, 1992; Needels et al., Proc. Natl. Acad. Sci. U.S.A. 90:10700, 1993; and Ohlmeyer et al., Proc. Natl. Acad. Sci. U.S.A. 90:10922, 1993). Similar approaches have also been used to study carbohydrate-protein interactions (e.g., see Oldenburg et al., Proc. Natl. Acad. Sci. U.S.A. 89:5393, 1992) and polynucleotide-protein interactions (e.g., see Ellington and Szostak, Nature 346:818, 1990 and Tuerk and Gold, Science 249:505, 1990). These approaches have also been extended to study interactions between proteins and unnatural biopolymers such as oligocarbamates, oligoureas, oligosulfones, etc. (e.g., see Zuckermann et al., J. Am. Chem. Soc. 114:10646, 1992; Simon et al., Proc. Natl. Acad. Sci. U.S.A. 89:9367, 1992; Zuckermann et al., J. Med. Chem. 37:2678, 1994; Burgess et al., Angew. Chem., Int. Ed. Engl. 34:907, 1995; and Cho et al., Science 261:1303, 1993). Yet further, alternative protein scaffolds that are loosely based around the basic fold of antibody molecules have been suggested and may be used in the preparation of inventive interaction partners (e.g., see Ku and Schultz Proc. Natl. Acad. Sci. U.S.A. 92:6552, 1995). Antibody mimics comprising a scaffold of a small molecule such as 3-aminomethylbenzoic acid and a substituent consisting of a single peptide loop have also been constructed. The peptide loop performs the binding function in these mimics (e.g., see Smythe et al., J. Am. Chem. Soc. 116:2725, 1994). A synthetic antibody mimic comprising multiple peptide loops built around a calixarene unit has also been described (e.g., see U.S. Pat. No. 5,770,380 to Hamilton et al.).

Any available strategy or system may be utilised to detect association between an antibody and its associated polypeptide molecular marker. In certain embodiments, association can be detected by adding a detectable label to the antibody. In other embodiments, association can be detected by using a labeled secondary antibody that associates specifically with the antibody, e.g., as is well known in the art of antigen/antibody detection. The detectable label may be directly detectable or indirectly detectable, e.g., through combined action with one or more additional members of a signal producing system. Examples of directly detectable labels include radioactive, paramagnetic, fluorescent, light scattering, absorptive and calorimetric labels. Examples of indirectly detectable include chemiluminescent labels, e.g., enzymes that are capable of converting a substrate to a chromogenic product such as alkaline phosphatase, horseradish peroxidase and the like.

Once a labeled antibody has bound a tumor marker, the complex may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In general, association between an antibody and its polypeptide molecular marker may be assayed by contacting the antibody with a tumor sample that includes the marker. Depending upon the nature of the sample, appropriate methods include, but are not limited to, immunohistochemistry (IHC), radioimmunoassay, ELISA, immunoblotting and fluorescence activates cell sorting (FACS). In the case where the polypeptide is to be detected in a tissue sample, e.g., a biopsy sample, IHC is a particularly appropriate detection method. Techniques for obtaining tissue and cell samples and performing IHC and FACS are well known in the art.

In general, the results of such an assay can be presented in any of a variety of formats. The results can be presented in a qualitative fashion. For example, the test report may indicate only whether or not a particular protein biomarker was detected, perhaps also with an indication of the limits of detection. Additionally the test report may indicate the subcellular location of binding, e.g., nuclear versus cytoplasmic and/or the relative levels of binding in these different subcellular locations. The results may be presented in a semi-quantitative fashion. For example, various ranges may be defined and the ranges may be assigned a score (e.g., 0 to 5) that provides a certain degree of quantitative information. Such a score may reflect various factors, e.g., the number of cells in which the tumor marker is detected, the intensity of the signal (which may indicate the level of expression of the tumor marker), etc. The results may be presented in a quantitative fashion, e.g., as a percentage of cells in which the tumor marker is detected, as a concentration, etc. As will be appreciated by one of ordinary skill in the art, the type of output provided by a test will vary depending upon the technical limitations of the test and the biological significance associated with detection of the protein biomarker. For example, in the case of certain protein biomarkers a purely qualitative output (e.g., whether or not the protein is detected at a certain detection level) provides significant information. In other cases a more quantitative output (e.g., a ratio of the level of expression of the protein in two samples) is necessary.

The resulting set of values are put into a database, along with outcome, also called phenotype, information detailing the treatment type, for instance tamoxifen plus chemotherapy, once this is known. Additional patient or tumour test sample details such as patient nodal status, histological grade, cancer stage, the sum total called patient clinicopathological information, are put into the database. The database can be simple as a spreadsheet, i.e. a two-dimensional table of values, with rows being patients and columns being filled with patient marker and other characteristic values.

From this database, a computerized algorithm can first perform pre-processing of the data values. This involves normalisation of the values across the dataset and/or transformation into a different representation for further processing. The dataset is then analysed for missing values. Missing values are either replaced using an imputation algorithm, in a preferred embodiment using KNN or MVC algorithms, or the patient attached to the missing value is excised from the database. If greater than 50% of the other patients have the same missing value then value can be ignored.

Once all missing values have been accounted for, the dataset is split up into three parts: a training set comprising 33-80% of the patients and their associated values, a testing set comprising 10-50% of the patients and their associated values, and a validation set comprising 1-50% of the patients and their associated values. These datasets can be further sub-divided or combined according to algorithmic accuracy. A feature selection algorithm is applied to the training dataset. This feature selection algorithm selects the most relevant marker values and/or patient characteristics. Preferred feature selection algorithms include, but are not limited to, Forward or Backward Floating, SVMs, Markov Blankets, Tree Based Methods with node discarding, Genetic Algorithms, Regression-based methods, kernel-based methods, and filter-based methods.

Feature selection is done in a cross-validated fashion, preferably in a naive or k-fold fashion, as to not induce bias in the results and is tested with the testing dataset. Cross-validation is one of several approaches to estimating how well the features selected from some training data is going to perform on future as-yet-unseen data and is well-known to the skilled artisan. Cross validation is a model evaluation method that is better than residuals. The problem with residual evaluations is that they do not give an indication of how well the learner will do when it is asked to make new predictions for data it has not already seen. One way to overcome this problem is to not use the entire data set when training a learner. Some of the data is removed before training begins. Then when training is done, the data that was removed can be used to test the performance of the learned model on "new" data.

Once the algorithm has returned a list of selected markers, one can optimize these selected markers by applying a classifier to the training dataset to predict clinical outcome. A cost function that the classifier optimizes is specified according to outcome desired, for instance an area under receiver-operator curve maximising the product of sensitivity and specificity of the selected markers, or positive or negative predictive accuracy. Testing of the classifier is done on the testing dataset in a cross-validated fashion, preferably naive or k-fold cross-validation. Further detail is given in U.S. patent application Ser. No. 09/611,220, incorporated by reference. Classifiers map input variables, in this case patient marker values, to outcomes of interest, for instance, prediction of stroke subtype. Preferred classifiers include, but are not limited to, neural networks, Decision Trees, genetic algorithms, SVMs, Regression Trees, Cascade Correlation, Group Method Data Handling (GMDH), Multivariate Adaptive Regression Splines (MARS), Multilinear Interpolation, Radial Basis Functions, Robust Regression, Cascade Correlation+Projection Pursuit, linear regression, Non-linear regression, Polynomial Regression, Regression Trees, Multilinear Interpolation, MARS, Bayes classifiers and networks, and Markov Models, and Kernel Methods.

The classification model is then optimised by for instance combining the model with other models in an ensemble fashion. Preferred methods for classifier optimization include, but are not limited to, boosting, bagging, entropy-based, and voting networks. This classifier is now known as the final predictive model. The predictive model is tested on the validation data set, not used in either feature selection or classification, to obtain an estimate of performance in a similar population.

The predictive model can be translated into a decision tree format for subdividing the patient population and making the decision output of the model easy to understand for the clinician. The marker input values might include a time since symptom onset value and/or a threshold value. Using these marker inputs, the predictive model delivers diagnostic or prognostic output value along with associated error. The instant invention anticipates a kit comprised of reagents, devices and instructions for performing the assays, and a computer software program comprised of the predictive model that interprets the assay values when entered into the predictive model run on a computer. The predictive model receives the marker values via the computer that it resides upon.

Once patients are exhibiting symptoms of cancer, for instance breast cancer, a tissue tumor sample is taken from the patient using standard techniques well known to those of ordinary skill in the art and assayed for various tumor markers of cancer by slicing it along its radial axis and placing such slices upon a substrate for molecular analysis by assaying for various molecular markers. Assays can be preformed through immunohistochemistry or through any of the other techniques well known to the skilled artisan. In a preferred embodiment, the assay is in a format that permits multiple markers to be tested from one sample, such as the Aqua Platform™, and/or in a quantitative fashion, defined to within 10% of the actual value and in the most preferred enablement of the instant invention, within 1% of the actual value. The values of the markers in the samples are inputted into the trained, tested, and validated algorithm residing on a computer, which outputs to the user on a display and/or in printed format on paper and/or transmits the information to another display source the result of the algorithm calculations in numerical form, a probability estimate of the clinical diagnosis of the patient. There is an error given to the probability estimate, in a preferred embodiment this error level is a confidence level. The medical worker can then use this diagnosis to help guide treatment of the patient.

In another embodiment, the present invention provides a kit for the analysis of markers. Such a kit preferably comprises devises and reagents for the analysis of at least one test sample and instructions for performing the assay. Optionally the kits may contain one or more means for using information obtained from immunoassays performed for a marker panel to rule in or out certain diagnoses. Marker antibodies or antigens may be incorporated into immunoassay diagnostic kits depending upon which marker autoantibodies or antigens are being measured. A first container may include a composition comprising an antigen or antibody preparation. Both antibody and antigen preparations should preferably be provided in a suitable titrated form, with antigen concentrations and/or antibody titers given for easy reference in quantitative applications.

The kits may also include an immunodetection reagent or label for the detection of specific immunoreaction between the provided antigen and/or antibody, as the case may be, and the diagnostic sample. Suitable detection reagents are well known in the art as exemplified by radioactive, enzymatic or otherwise chromogenic ligands, which are typically employed in association with the antigen and/or antibody, or in association with a second antibody having specificity for first antibody. Thus, the reaction is detected or quantified by means of detecting or quantifying the label. Immunodetection reagents and processes suitable for application in connection with the novel methods of the present invention are generally well known in the art.

The reagents may also include ancillary agents such as buffering agents and protein stabilizing agents, e.g., polysaccharides and the like. The diagnostic kit may further include where necessary agents for reducing background interference in a test, agents for increasing signal, software and algorithms for combining and interpolating marker values to produce a prediction of clinical outcome of interest, apparatus for conducting a test, calibration curves and charts, standardization curves and charts, and the like.

The prenylated peptide library can immobilized on a substrate, such as an array, and the array can be high-throughput. Such arrays are known in the art and are described herein. The array can comprise prenylated peptides, or can comprise test samples which are then contacted with prenylated peptides in solution. In either case, the prenylated peptide interacts with a test sample, such as binding to a surface molecule of the test sample. In one example, the surface molecule can comprise a cell surface protein, a lipid, a carbohydrate, an envelope protein or an envelope glycoprotein. Either the test sample or the prenylated peptide can comprise a detectable marker. Again, such markers are known to those of skill in the art.

Also disclosed is a prenylated peptide library. Such a library is comprised of prenylated peptides which can be specific for a known disease or condition, or which are randomly generated. The creation of such libraries is generally known in the art, and can be applied to prenylated peptide libraries. Further disclosed are kits comprising such prenylated peptide libraries. These kits can be specific for a known pathogen or disease (such as a given cancer marker), or can be randomly generated. In one example, the prenylated peptide library can interact with an antibody which is known to be associated with a given disease or disorder. The antibody, for instance, can comprise a detectable label.

Also disclosed is a method for screening for a prenylated peptide that interacts with a given composition, the method comprising exposing the given composition to a prenylated peptide, and determining interaction between the prenylated peptide and the given composition. The prenylated peptide can be produced by the methods disclosed herein for prenylating peptides. The prenylated peptide c an be part of a library, or can be used individually. The given composition can a protein, antibody, or nucleic acid, for example. This method can be used to screen for drugs that interact with a given composition, thereby inhibiting or enhancing its activity. The given composition can be associated with a disease or disorder, such as cancer or an infectious disease. Such disease and disorders are enumerated throughout. Interaction between the prenylated peptide and given composition can indicate that the prenylated peptide is useful in treating the disease or disorder.

Also disclosed is a method of treating a disease or disorder, comprising contacting a subject with a prenylated peptide made or identified by the methods disclosed herein. The prenylated peptide can be used to treat or prevent a disease or disorder associated therewith. For example, the prenylated peptide can be used to inhibit a given protein, or to interact with a pathogen, thereby inhibiting its ability to infect. The prenylated peptide can be given in conjunction with a second composition known to treat the disease or disorder, for example. An example of a second composition is a known drug or antibiotic, or an antibody.

The prenylated peptides disclosed herein can also be used to enhance the effectiveness of a second composition. This can done by increasing the effectiveness of the second composition, such as enhancing delivery of the second composition to the target, or by both the prenylated peptide and the second composition working in concert on different aspects of the disease or disorder. Such methods of enhanced effectiveness by combination therapy are known to those of skill in the art.

Prophylactic and therapeutic compounds that may be used in the methods and compositions of the invention include, but are not limited to, proteinaceous molecules, including, but not limited to, peptides, polypeptides, proteins, including post-translationally modified proteins, antibodies, etc.; small molecules (less than 1000 daltons), inorganic or organic compounds; nucleic acid molecules including, but not limited to, double-stranded or single-stranded DNA, double-stranded or single-stranded RNA, as well as triple helix nucleic acid molecules. Prophylactic and therapeutic compounds can be derived from any known organism (including, but not limited to, animals, plants, bacteria, fungi, and protista, or viruses) or from a library of synthetic molecules. In certain embodiments, one or more compounds of the invention are administered to a mammal, preferably a human, concurrently with one or more other therapeutic agents useful for the treatment of cancer or a disorder. The term "concurrently" is not limited to the administration of prophylactic or therapeutic agents at exactly the same time, but rather it is meant that compounds of the invention and the other agent are administered to a subject in a sequence and within a time interval such that the compounds of the invention can act together with the other agent to provide an increased benefit than if they were administered otherwise. For example, each prophylactic or therapeutic agent may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route.

In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

A "chemotherapeutic agent" or "chemotherapeutic compound" is a chemical compound useful in the treatment of cancer. Chemotherapeutic cancer agents that can be used in combination with those disclosed herein include, but are not limited to, mitotic inhibitors (vinca alkaloids). These include vincristine, vinblastine, vindesine and Navelbine™ (vinorelbine,5'-noranhydroblastine). In yet other embodiments, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that may be used in the methods and compositions of the invention are podophyllotoxin derivatives, such as etoposide, tenipo-side and mitopodozide. The invention further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The invention encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions of the invention include antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The invention further encompasses other chemotherapeutic cancer agents including without limitation anti-tumor antibodies, dacarbazine, azacytidine, amsacrine, melphalan, ifosfamide and mitoxantrone.

The compositions disclosed herein can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/antineoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the invention include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin;

cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A;

placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Also disclosed is a method of enhancing the effectiveness of a known peptide, the method comprising prenylating the known peptide. Such methods of prenylation are disclosed herein. The peptide can be known already to have effectiveness in treating a given disease or disorder, and prenylation of the peptide can increase the effectiveness by enhancing delivery, or by increasing the efficacy of the peptide. The known peptide can an antitumor or an antimicrobial composition, for example.

2. Method of Treating Cancer

The disclosed compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Compounds disclosed herein may also be used for the treatment of precancer conditions such as cervical and anal dysplasias, other dysplasias, severe dysplasias, hyperplasias, atypical hyperplasias, and neoplasias.

3. Methods of Treating Pathogenic Diseases

F. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

A Minimal Gene Set for In Vivo Production of Cyclic Peptide Libraries

To demonstrate the engineering potential of the cloned tru pathway, homologous recombination in yeast was used to replace truE1 with truE2. A ~4 kb piece harboring truE2 was amplified by PCR and used to cross over the tru1 pathway. The recombinant construct now contained truE2 encoding patellin 6 and trunkamide, in place of the original patellins 2 and 3. In an *E. coli* fermentation experiment, no peaks corresponding to patellins 2 or 3 were detected while a new peak for trunkamide was clearly observed and compared to authentic standards using high resolution mass analysis (FIG. 7 and FIG. 8) (Carroll 1996). These experiments serve as a proof of principle for the ability to engineer the tru pathway for the production of clinically important compounds. Recombination also allows the functional rescue of sequences from environmental DNA that may be too rare or degraded for traditional cloning approaches.

Figure 1C:
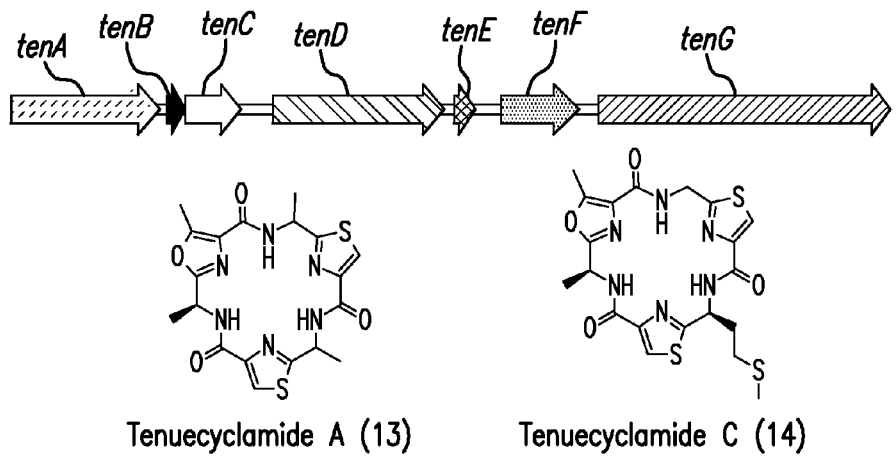
Figure 1D:
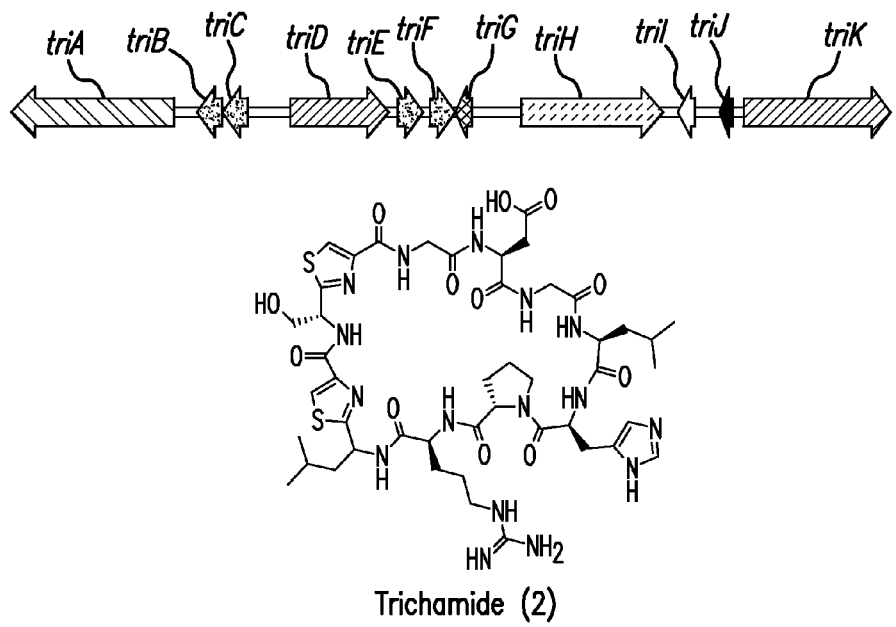

To identify homologs from free living cyanobacteria and observe further functional evolution, the tenuecyclamide-producing strain, *Nostoc spongiaeforme* var. *tenue* was studied (Banker 1998). A homology-based strategy led to the identification of a fosmid containing the ten cluster, a candidate for tenuecyclamide biosynthesis (FIG. 1c). Although the tenuecyclamide- and patellamide-producing strains are distantly related, the ten cluster is highly similar to the pat cluster. It is composed of seven genes encoded on the same strand (tenA to tenG). Most of the ten genes show 70 to 80% identity to their homologous pat genes at the DNA and protein level with the exceptions of TenC and TenF (~50% identity with pat homologs). A unique feature in the ten cluster is its precursor peptide, TenE, which encodes two copies of the primary amino acid sequence of each of the hexapeptides tenuecyclamide A and C, for a total of four copies (FIG. 10. The recognition sequences are similar to those found in PatE.

By mining the genome sequence of *Lyngbya aestuarii* CCY9616, a third patellamide-like pathway type representing a fifth new gene cluster was identified. The lyn cluster contains homologs of all the genes found in the pat cluster (lynA to lynG). However, it contains five additional coding sequences for which no function could be assigned (FIG. 1e). The precursor peptide gene, lynE, was identified and re-annotated (FIG. 10. From LynE sequences, new structures have been found (15,16).

Cyanobactins are widespread in cyanobacteria. About 100 probable cyanobactins have been previously described and are widely distributed through taxonomically distant species. This observation places the cyanobactins assembly line reported here as one of the major routes to small molecule biosynthesis in cyanobacteria, after the polyketide synthases and nonribosomal peptide synthetases.

TABLE 3

Sequence of primers used.

| Primer's name | Primer's sequence (5'-3') |
|---|---|
| PatAf-BspH1 | ATCATGAATAGAGATATTTTGCGAAC |
| PatAr-Eag1 | TCGGCCGTTCCTTAGTAAGAAGAAGACCAAG |
| PatDf-BspH1 | TTCATGAACCCAACCGCGCTCCAAATTAAG |
| PatDr-Not1 | GCCGCGGCCGCAAACTTGAAAATGCTTAAAACG |
| PatEf-Ndel | CCAACCAACATATGAACAAGAAGAACATTCTACCCC |
| PatEr-Kpn1 | TTCTTCTTGGTACCCTTATTCACCATC |
| PatFf-Ndel | AACATATGGACTTAAATTGACAGGCTTC |
| PatFr-Kpn1 | ATGACTAGGTACCTGAGTCAATGCAAATG |
| PatGf-Ndel | CCATATGATCACGATAGACTACCCTTTC |
| PatGr-Kpn1 | CGGTACCCCAATAACTACTTTGAGACGGTG |
| PN-W-D-1-F | GAAAGCTCATCCTCTGAGCCGA |
| PatEpnr-Kpn1 | AATTCGGTACCTTAGTCGTCGTAAGAGCAGAG |
| pat(G9216PN)R | AAACTCCAAAGCCCGCGCCATAT |
| patF1pn-f | CACCATGATTATGACTACTACTTGGC |
| patF1pn-r | TACCGCCTTGCGATAATAGA |
| patF2pn-f | CACCATGGTTTTGAGTCAATTATCTAA |
| patF2pn-r | GACTCTCATCATTCTTGACTCATCA |
| pat(G9939)R | TGGAGGGGGCGATCACCATCT |
| TruEpn-StrepResis-F | TGGATGCCTCGACCGTTCCTACCCTCTGCTCTTACG ACGACTAAATGTGTCCGCAGCGCCCGC |
| StrepResis- | TTTATTTCTATAATTCACATTAAGCGTAATCCAAAA ATCTCGATT |
| TruF2-R | TTTAACGACCCTGCCCTGAACCG |
| PatEf-NoRes | ATGAACAAAAAAACATTCTGCCCCAA |

TABLE 4

PCR experiments performed to examine integrity of tru2 pathway.

| Region examined | Forward primer | Reverse primer | Product size | Annealing temp. and extension time |
|---|---|---|---|---|
| truD to truE | PN-W-D-1-F | PatEpnr-Kpn1 | 1760 bp | 52° C., 2 min |
| ° truE to truF1 | PatEf-Ndel | patF1pn-r 50 | 1460 bp | 50° C., 1.5 min |
| truE to truF2 | PatEf-Ndel | patF2pn-r | 2440 bp | 50° C., 2.5 min |
| truA to truE | PatAf-BspH1 | PatEpnr-Kpn1 | 5650 bp | 52° C., 5 min |
| truF1 to truG | patF1pn-f | PatGr-Kpn1 | 5122 bp | 52° C., 5 min |
| truF2 to truG | patF2pn-f | pat(G9216PN)R | 2544 bp | 50° C., 2.5 min |
| truE to truG | PatEf-Ndel | PatGr-Kpn1 | 5643 bp | 52° C., 6 min | a) General Methods.

PCR amplification was performed in a 10 μl reaction mixture containing 10×PCR buffer (Invitrogen), 1.5 mM MgSO$_4$, 0.4 μM dNTP mix (Invitrogen) and 0.5 U Platinum Taq HiFi DNA Polymerase (Invitrogen). The reaction was performed with 1 μl of template DNA (genomic or plasmid DNA) and primers were added to a final concentration of 2 μM each. Thermal cycling was performed in a MiniCycler™ (MJ Research) or Peltier Thermal Cycler (MJ Research). The initial denaturation step at 94° C. for 4 min was followed by 35 cycles of DNA denaturation at 94° C. for 30 s, primer annealing for 30 s at X° C., and DNA strand extension at 68° C. for X min, followed by a final extension step at 68° C. for 10 min. Exact annealing temperatures and extension times are given for each reaction below. PCR experiments were always run with a negative control (sterile water) and a positive control. The PCR products were viewed by agarose gel electrophoresis on a 1% gel and the bands needed for further processing were cut and gel extracted using the QIAquick Gel Extraction Kit (Qiagen) or TOPO-XL cloning kit (Invitrogen). Top 10 *E. coli* cells (Invitrogen) were used for heterologous expression of the cloned pathways and for propagation of the constructs. LB medium was used for growing the strains supported with appropriate antibiotics. Standard concentrations were: kanamycin and ampicillin, 50 μg/ml; chloramphenicol, 25 μg/ml; and streptomycin, 12.5 μg/ml. Different concentrations used in specific experiments are listed within. High performance liquid chromatography coupled to mass spectrometry (HPLCMS) was as follows. Samples were dissolved in 1:1 water:acetonitrile and injected on a Waters Alliance 2795 HPLC, using an analytical C18 column (Phenomenex) and an acetonitrile/water gradient at a flow rate of 0.2 ml/min. Gradient conditions were initially 50% water, 50% acetonitrile to 1% water, 99% acetonitrile over 15 or 25 minutes and held at 20 that level for another 5 minutes. 1% formic acid was used in the water and/or acetonitrile to enhance ionization. For high resolution HPLC mass spectrometry (HPLC-HRESIMS), a Micromass Q-TOF mass spectrometer was used with a LockSpray running concurrently to ensure higher mass accuracy. For low resolution HPLC mass spectrometry (HPLC-LRESIMS), a Quattro II mass spectrometer was used. All analyses were done in positive ion mode.

Collection and processing of samples. Solomon Islands samples *Lissoclinum patella* 06-027 and *Didemnum molle* 06-028 were collected at a depth of ~5 m off Njanjelakalau, Florida Islands, S 8°57.35' E 159°59.12'. *L. patella* 06-037 was collected from 2-5 m depth in Momi Bay, Fiji, S17°55' E 177°16'. Morphological properties and/or 18S rRNA gene sequence analysis were used for taxonomic identification. Presence of *Prochloron* in the samples was confirmed by visual inspection and/or light microscopy. Samples were aliquoted and stored frozen, in RNALater (Amersham), and in isopropanol. Enriched *Prochloron* cells and purified *Prochloron* DNA were obtained as previously described.

Tenuecyclamide-producing strain *Nostoc spongiaeforme* var. *tenue* was grown using media and conditions as previously described with some minor modifications: it was grown in a 24-hour light cycle with gentle stirring using a magnetic stir bar. Nostoc DNA was isolated using the Maxwell 16 tissue kit (Qiagen) following the manufacturer's protocol.

Fosmid library construction. Genomic DNA from samples 06-037 and *Nostoc* sp. was cloned into the pCC1FOS fosmid vector (Epicentre) following the manufacturer's protocol. A library of about 600 colonies was constructed from each sample. Colonies were then picked into 96-well plates and stored in 30% glycerol.

Fosmid library screening. Both libraries were end-sequenced to screen for pat-like genes. They were also screened with pat-specific and degenerate primers (Table 3). Fosmids FTREC24 and FTRDC74 containing the intact tru and ten clusters were thus identified and sequenced for 6× coverage. Sequence data were analyzed using Sequencher, and BLAST searches were performed on the DNA and protein sequences.

Cloning of the tru cluster encoding patellins 3 and 2. Exact match primers (patAf-BspH1 and patGr-Kpn1) were used to amplify the full tru cluster (Table S1). PCR was performed as described in the general methods with an annealing temperature of 54° C. and an extension time of 10 min. Genomic DNA or fosmid FTREC24 were used as templates. The PCR product (~11 kb) was gel extracted as described in the general methods. The gel extraction product was then cloned into the vector pCR2.1-TOPO (Invitrogen) following the manufacturer's protocol. Ligated product was chemically transformed into TOP10-*E. coli* cells (Invitrogen), spread on plates with appropriate antibiotics and grown at 30° C. Transformants were screened by restriction digest for the presence of inserts leading to the identification of the vector TOPO-E1 containing the full cluster (FIG. 4). End sequencing confirmed the presence of tru in frame with the constitutively expressed lacZα gene. Transformants selected at 37° C. did not yield any plasmids with intact inserts, probably due to a rearrangement problem. Thus, the identified vector was propagated and expressed at 30° C. Heterologous expression of the tru cluster. *E. coli* strain Top10 (Invitrogen) was used for constitutive expression of tru via the lac promoter. Fresh colonies were picked and grown overnight at 30° C. in LB/kanamycin to be used as a seed culture. One ml of this culture was used to inoculate 1 L of LB medium containing kanamycin. The expression was allowed to go for about 24 hours at 30° C. in a rotary shaker to allow accumulation of products. The culture was centrifuged at 5000 rpm for 10 min and the broth was removed and subjected to chemical extraction by shaking for about 30 min with diaion resin HP20SS (SUPELCO). The resin was then washed with water (500 ml) and eluted with 100% methanol (250 ml). The methanol fraction was dried by rotary evaporation and the remaining residue was dissolved in water (30 ml). The water fraction was then extracted three times with equal volumes of ethyl acetate. The organic extracts were combined, dried by rotary evaporation and fractionated by C18 chromatography using 25, 50, 75 and 100% acetonitrile in water. HPLC-HRESIMS analyses of the fractions were performed as explained in the general methods. Controls consisted of identical expression and extraction experiments. Positive controls were doped with patellins 2 and 3 before extraction, while negative controls were expressions consisting of various other vectors containing slightly different inserts. Patellins 3 and 2 were readily detected and were compared to standards isolated from sample 06-037. For confirmation of the reproducibility of the system, the entire expression/extraction process was repeated three times and analyzed by HPLC-ESIMS using different instruments and columns. Both products were observed in three replicates and never in negative controls lacking the TOPO-E1 vector (FIG. 3). Moreover, a high-resolution exact mass analysis of the recombinant patellin 2 matched the reported molecular formula within a 1.5 ppm error (FIG. 6).

Discovery of the trunkamide cluster in 06-027 and 06-028. Specific primers (patEf-Nde1 and patEpnr-Kpn1, Table S1) were designed to amplify truE1. PCR experiments using this set of primers were performed on DNA from samples 06-027 and 06-028. Conditions and amounts of components were the same as described above except for the annealing temperature and the extension time Annealing temperature for the truE PCR was 51° C. and extension time was 30 sec. Template DNA was added in 3 dilutions (1×, 1/10× and 1/100×) and PCR experiments were always run with a negative control (sterile water) and a positive control known to have the truE gene. The products were viewed by agarose gel electrophoresis on a 1% gel and the bands of the expected size (~200 bps) were cut and gel extracted using the QIAquick Gel Extraction Kit (Qiagen). The gel-extraction products were adjusted to a concentration of 30 ng/µl and sequenced at the University of Utah core facility. Sequence data were analyzed using Sequencher, and BLAST searches were performed on the DNA and protein sequences. Integrity and orientation of the trunkamide cluster tru2. The full truE2 cluster was amplified with the primers (patAf-Bsph1 and patGr-Kpn1, Table 3) with the same conditions of the truE1 cluster showing a product of the same size. To further investigate if tru1 and tru2 are identical and syntenic, orientation PCR experiments were done. PCR components and conditions are the same as described above except for a few changes. These changes, the genes examined, and product sizes are listed in Table S2 and shown in FIG. 8. Selected products flanking the variable region in truE2 were sequenced to show >99% DNA sequence identity.

Figure 7:
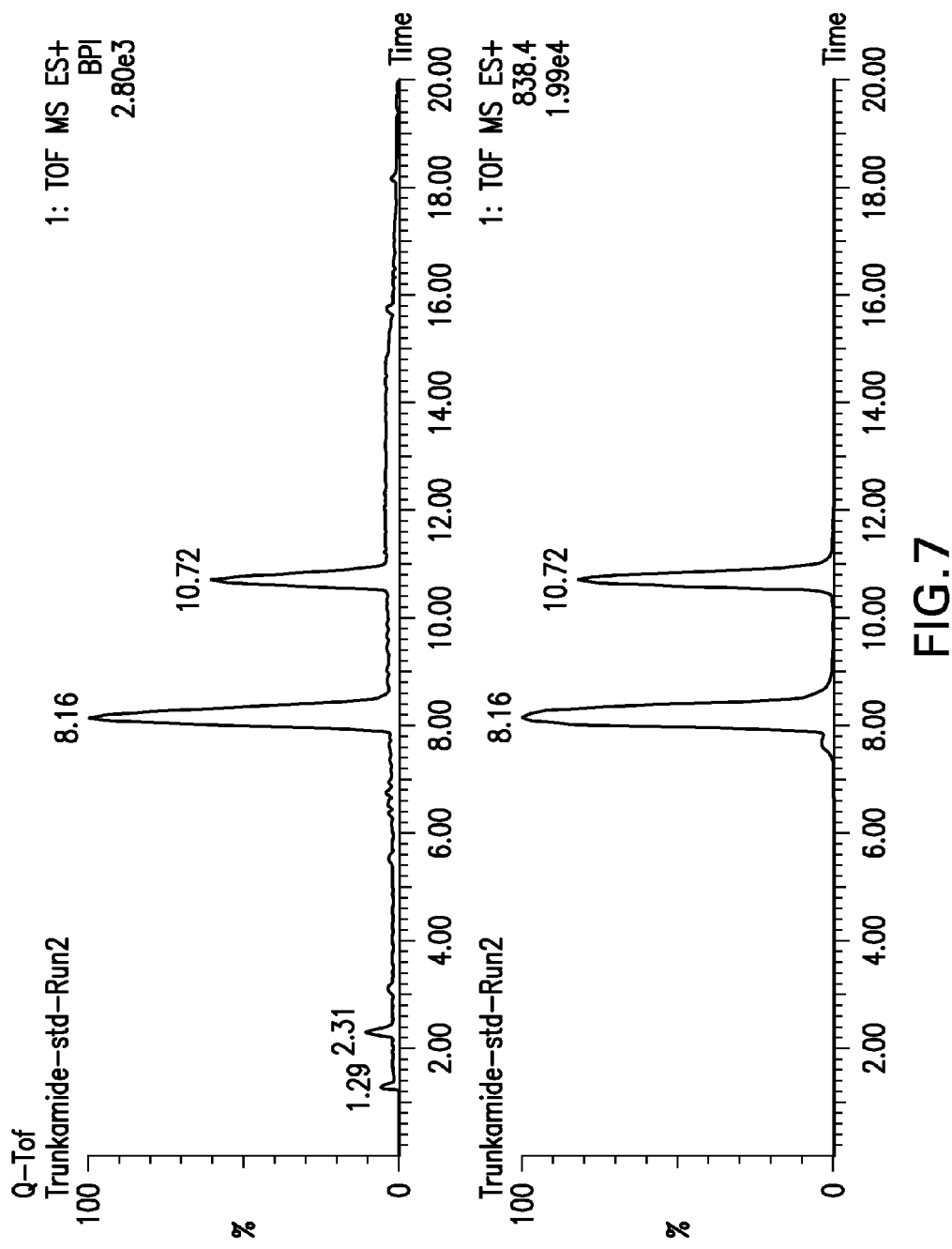
FIG. 7 shows TOPO-E1 map is shown on top and was crossed over by a 1.2 kb PCR product containing the streptomycin resistance gene to yield the truF1 knock out vector TOPO-E1-Strep-ΔF1 (map shown at the bottom). Agarose gel lane 1, 4: 2-log ladder; lane 2: BspH1 digest of TOPO-E1-Strep-ΔF1; lane 3, BspH1 digest of TOPO-E1.
Figure 8:
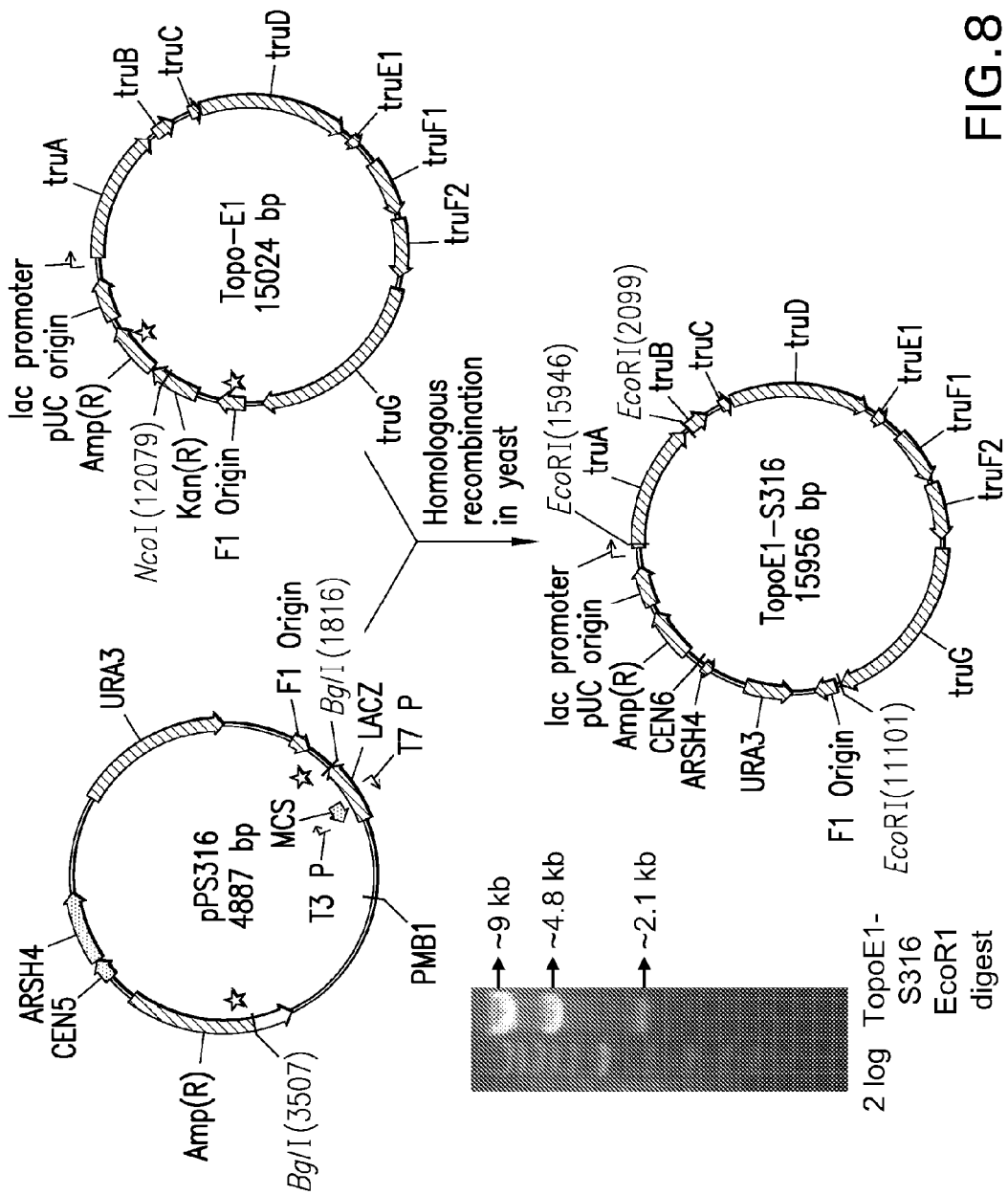
FIG. 8 shows heterologous expression of trunkamide. Generation of the vector Topo-E1-S316 by homologous recombination in yeast. The vectors used to generate the yeast manipulation plasmid are shown. Restriction enzyme and recombination sites used are marked by red stars. The ampicillin resistance gene and the F1 origin of replication were used as the identical sites for the homologous recombination.
Figure 9:
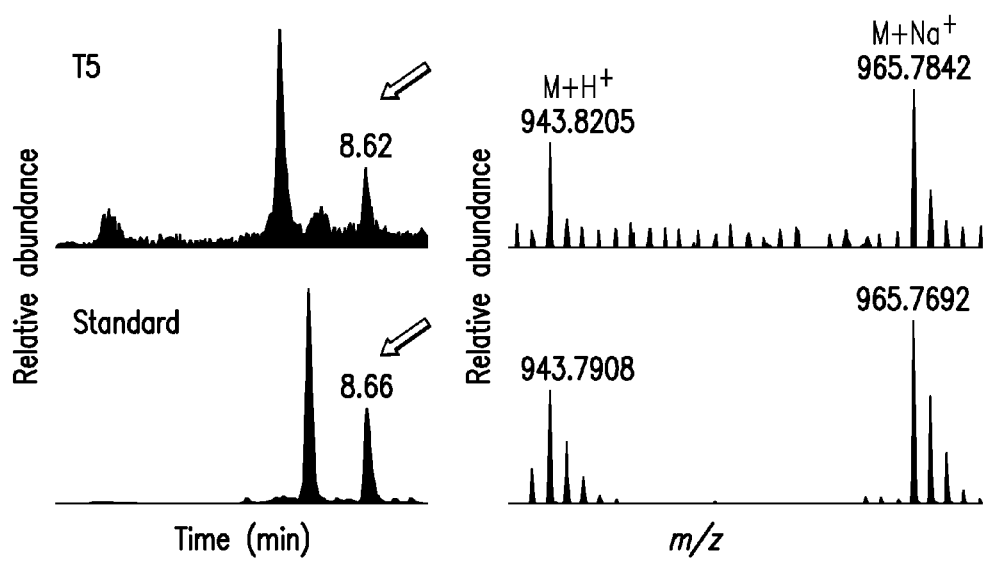
FIG. 9 shows heterologous production of patellin 3. Top: *E. coli* broth; bottom: standard of patellins 3. Data are shown for patellin 3 and a similar pattern was observed for patellin 2. Left, a total ion chromatogram filtered for m/z=943 corresponding to patellin 3. Both the standard and the recombinant products eluted at exactly the same time. Right, the masses of the recombinant and standard patellin 3.
Figure 10:
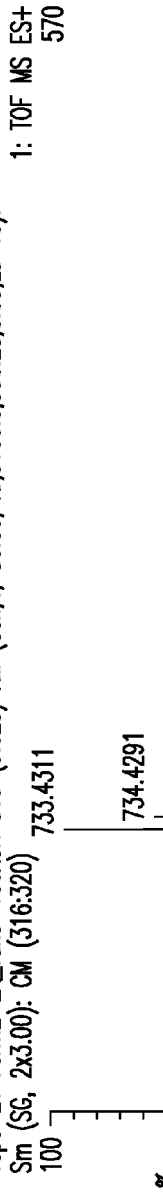
FIG. 10 shows high-resolution exact mass of recombinant patellin 2. The full exact mass and elemental composition report of the recombinant patellin 2 is shown. The exact mass of patellin 2 matches that calculated for its reported molecular formula within a 1.5 ppm error (boxed in red).
Figure 11:
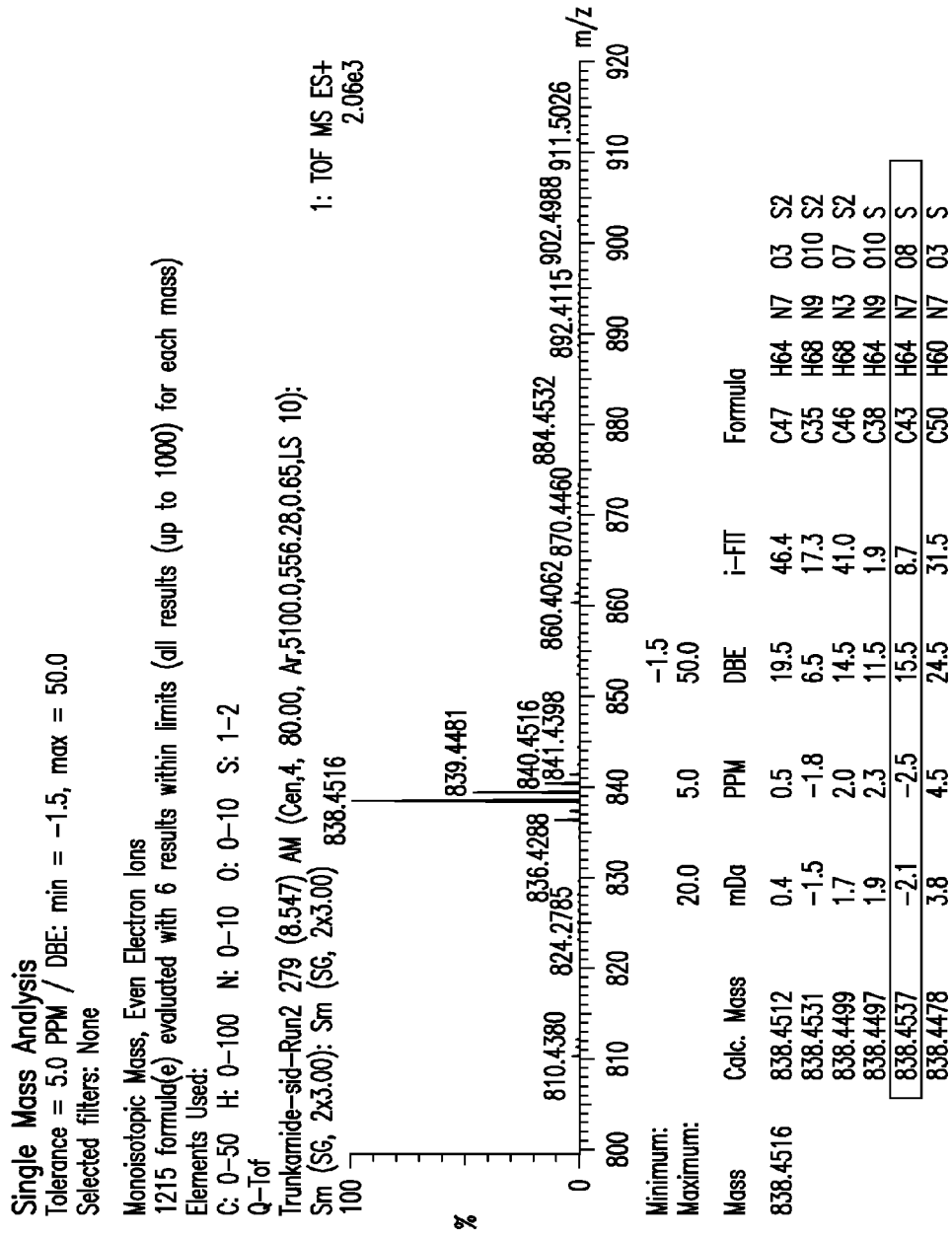
FIG. 11 shows trunkamide isomer 1 exact mass. The full exact mass and elemental composition report of the first isomer of purified trunkamide is shown. Its exact mass matches that calculated for its reported molecular formula within a 2.5 ppm error (boxed in red).
Figure 12:
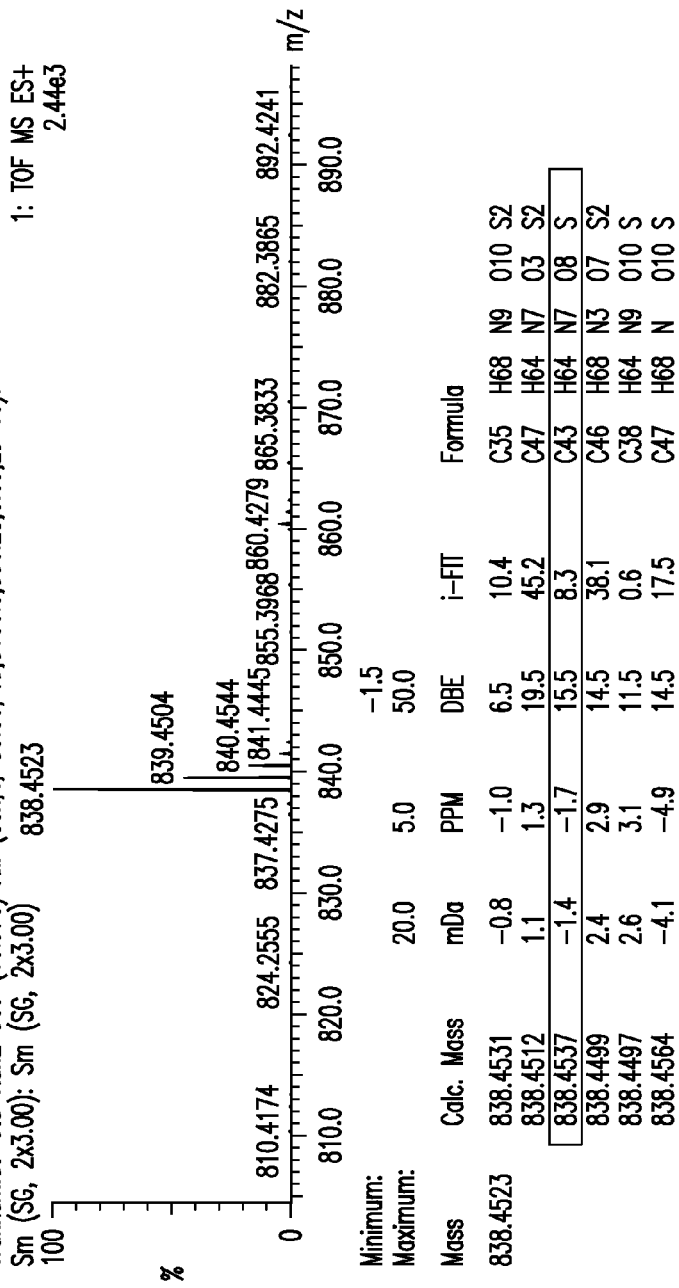
FIG. 12 shows trunkamide isomer 2 exact mass. The full exact mass and elemental composition report of the second isomer of purified trunkamide is shown. Its exact mass matches that calculated for its reported molecular formula within a 1.7 ppm error (boxed in red).
Figure 13:
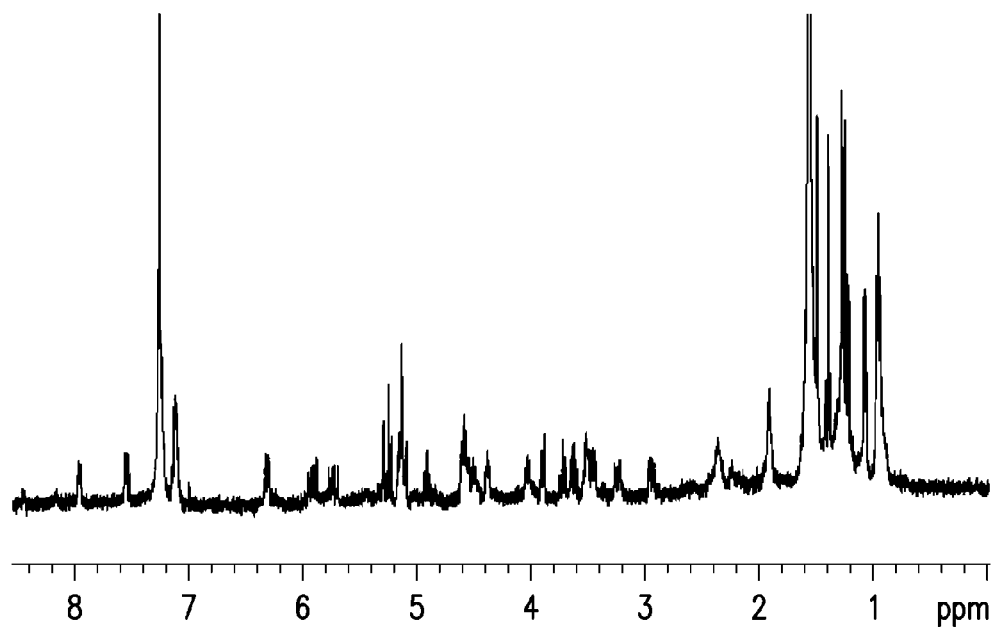
FIG. 13 shows HNMR spectra of purified trunkamide from *D. molle* sample 06-028 in CDCl3.
Figure 14:
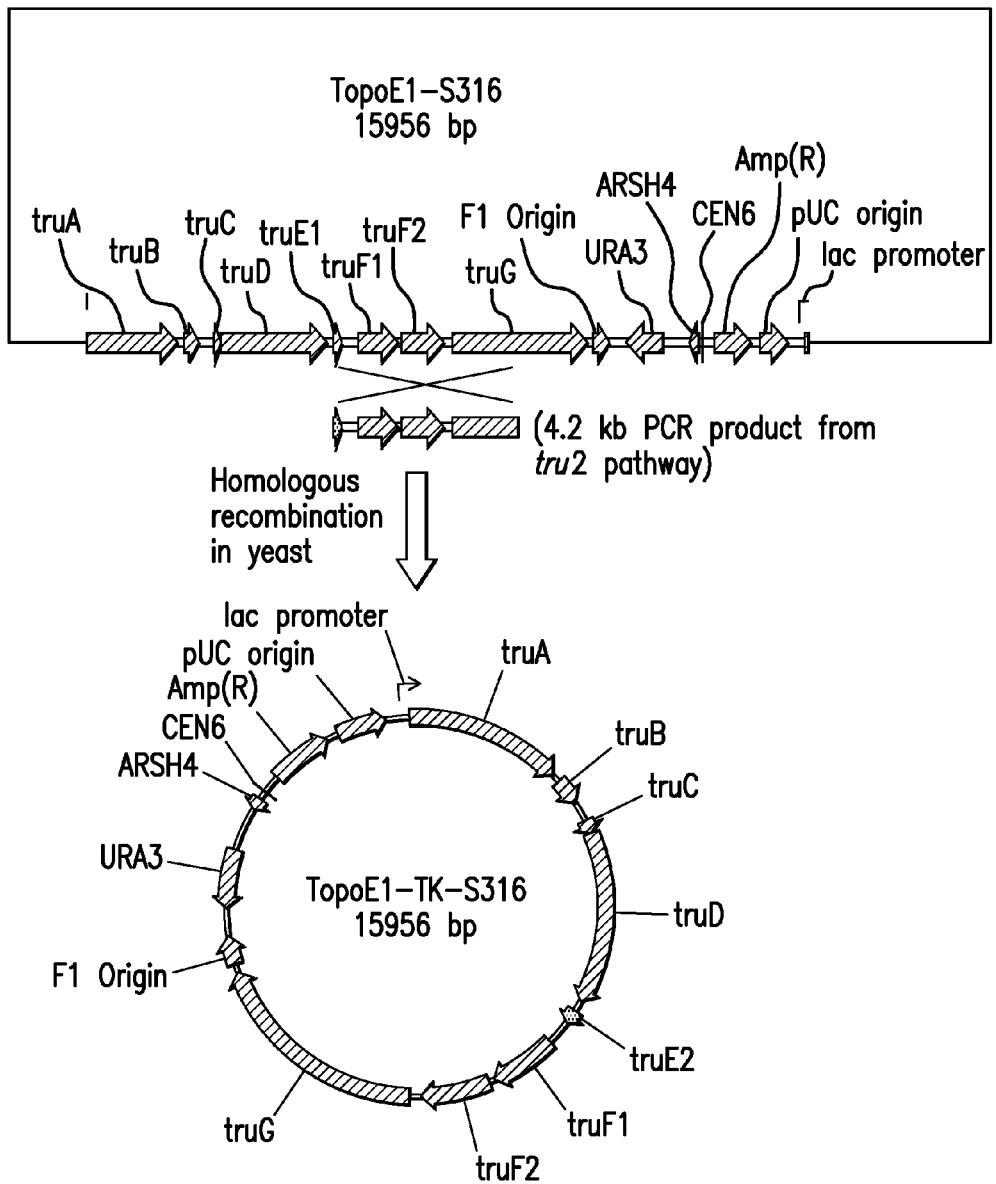
FIG. 14 shows genetic engineering of the trunkamide pathway by homologous recombination in yeast. At top, Topo-E1-S316 containing the full tru1 pathway is shown. This vector was crossed over by a PCR product amplified from the tru2 pathway. Resulting recombinant vector (bottom) differs only in the truE2 region encoding for trunkamide and patellin 6. Insertion was confirmed by sequencing.
Figure 15:
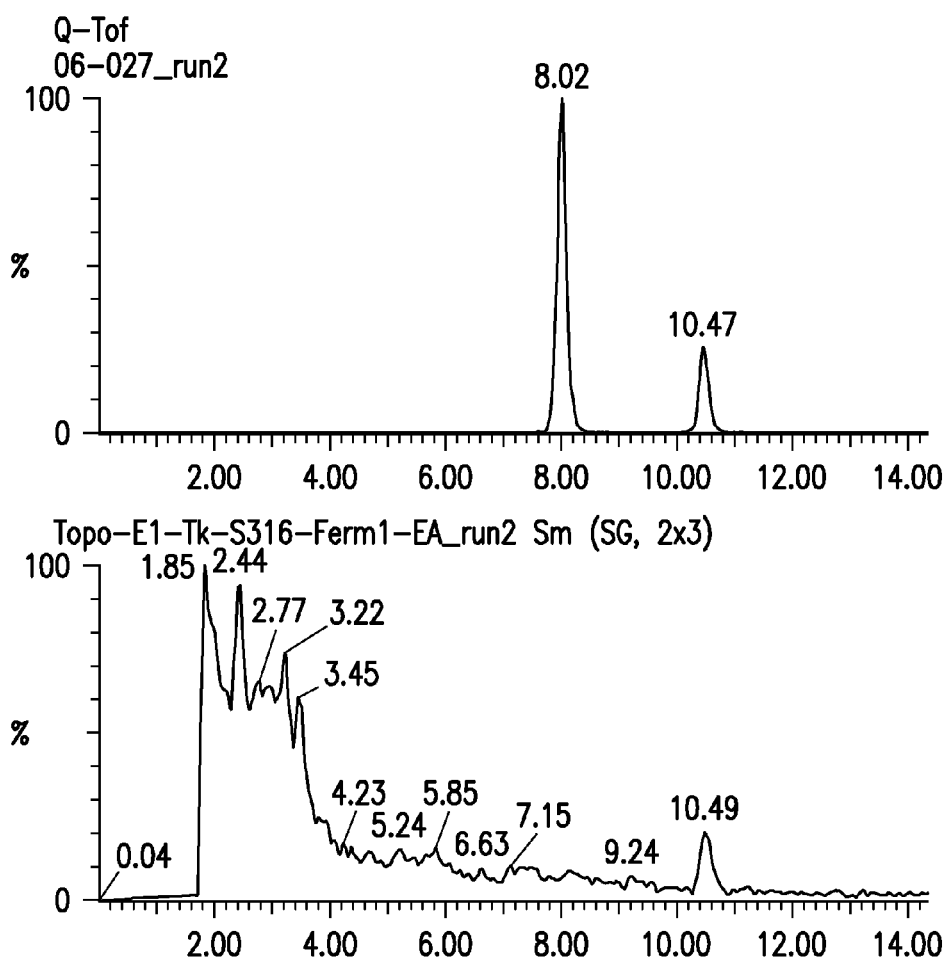
FIG. 15 shows heterologous production of trunkamide in *E. coli* broth. Top and bottom are HPLC-HRESIMS chromatograms filtered for the m/z of 838 corresponding to trunkamide. On top, standard trunkamide from sample 06-027. At the bottom, broth of an *E. coli* fermentation experiment containing the vector Topo-E1-TK-S316 encoding for trunkamide. Both recombinant and standard trunkamide elute at exactly the same time.
Figure 16:
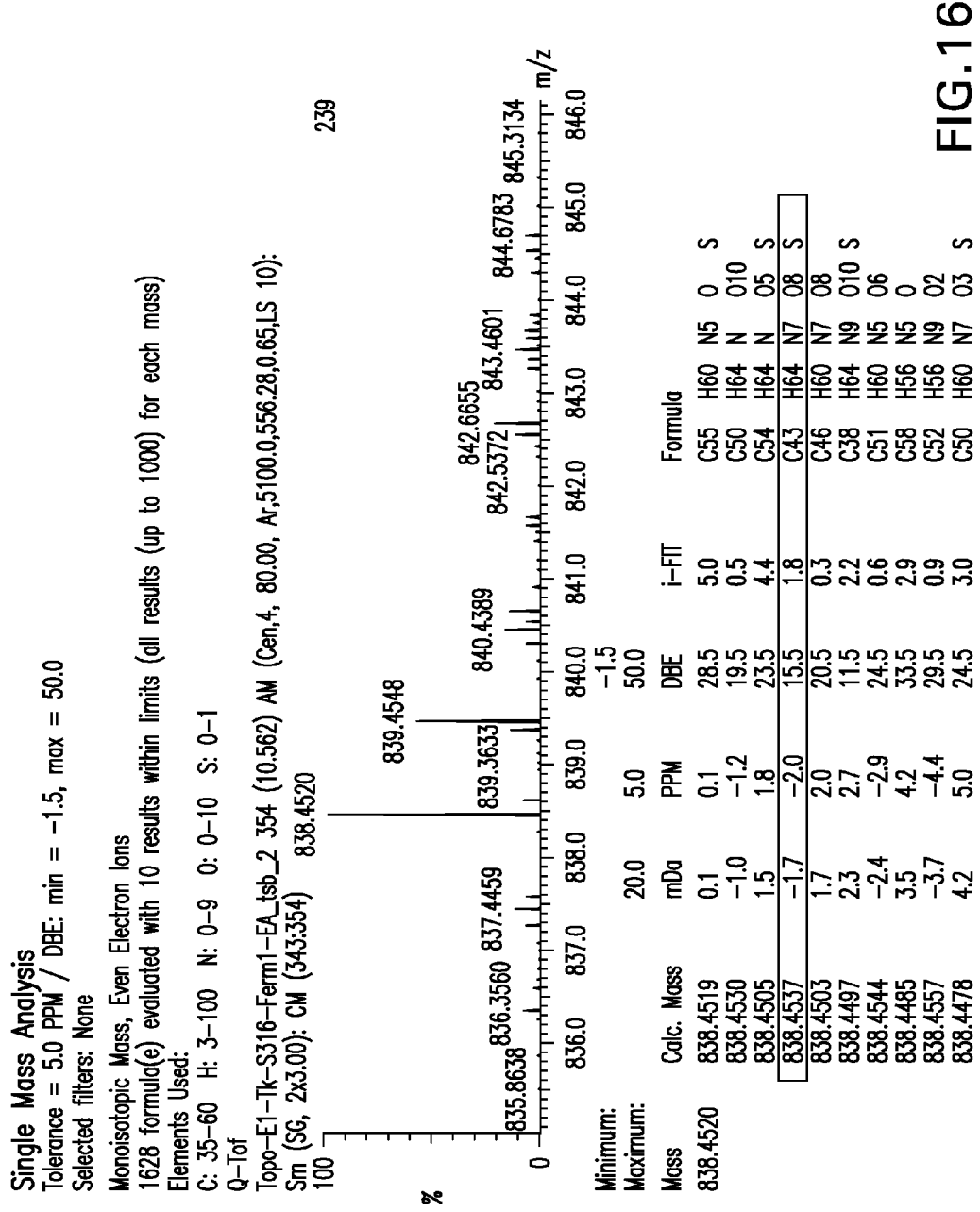
FIG. 16 shows high-resolution exact mass of recombinant trunkamide. The full exact mass and elemental composition report of the recombinant trunkamide is shown. Its exact mass matches that calculated for its reported molecular formula within a 2.0 ppm error.

Chemical analysis of ascidians. For initial screening of the samples, whole ascidians were extracted at least two times with methanol. The dried extracts were combined and dissolved in 1:1 water:acetonitrile solvent mixture and analyzed by HPLC-HRESIMS as described above. For the *L. patella* sample 06-037 containing patellins 2 and 3, the whole organism (32 g) was diced and extracted three times with methanol (50 ml). Extracts were then combined, dried on a rotary evaporator and partitioned three times between hexane (200 ml) and methanol:water (9:1, 200 ml). Water (100 ml) was added to the aqueous layer, which was then extracted three times with chloroform. Following rotary evaporation of the chloroform fraction, an organic extract (200 mg) was obtained. The extract was loaded on a column containing LH20 (30 gm) in 1:1 methanol:chloroform. Fractions (10 ml) were collected and analyzed by TLC and $^1$H NMR. For the *D. molle* sample 06-028 from which trunkamide was purified to homogeneity, the whole organism was freeze-dried prior to extraction. The dry material (~7 g) was extracted five times with freshly distilled dichloromethane (each with 70 ml). The extracts were combined and dried on a rotary evaporator then dissolved in methanol (40 ml). The methanol fraction was extracted five times with equal volumes of hexanes. The methanol fraction was then dried on a rotary evaporator and fractionated on a C18 column. Fractions (10 ml) were collected from a gradient of 100% water to 100% acetonitrile with a 25% increment and were checked by $^1$H NMR after rotary evaporation and/or freeze-drying. The 75% fraction (~2 mg) showed peaks matching the reported 1H NMR spectra of trunkamide. For further purification of trunkamide, an Onyx Monolithic Semi-PREP C18 (100×10 mm, Phenomenex) column was used under the following conditions: gradient from 50:50 acetonitrile:water to 100% acetonitrile in 20 min followed by 100% acetonitrile for 10 min, monitoring at λ=240 nm. Fractions were collected and screened by 1H NMR. The fraction collected at 2.5 to 7 min yielded almost pure trunkamide (1.1 mg, FIG. 12). HPLC-HRESIMS analysis showed that trunkamide existed as two isomers indistinguishable by our HPLC or 1H NMR analyses (FIG. 9). The same pattern existed in other ascidian samples containing trunkamide within the collection. Both isomers showed a distinct trunkamide fragment and had exact masses within 3 ppm of that calculated for trunkamide's molecular formula (FIGS. 10 and 11). This is consistent with the previous observation that trunkamide's phenylalanine residue isomerizes from L to D in solution. Alternatively, this duplication may reflect transient conformational isomerism. truF1 knock out experiment. The overall strategy was inspired by REDIRECT technology (Gust B, Kieser T and Chater K F, John Innes Centre, 2002). Strain BW25113/pIJ790 was obtained directly from John Innes Centre and grown at 30° C. At an OD600~0.4, cells were harvested, washed 3× with ice cold 10% glycerol and used for electroporation with the plasmid TOPO-E1 harboring the full tru1 cluster (FIG. 7).

After selection on LB plates with the appropriate antibiotics, the strain BW25113/pIJ790/TOPO-E1 was grown overnight in 7 ml of LB medium with kanamycin and chloramphenicol. 500 μl of this culture and 500 μl of 1M L-arabinose were then inoculated into 50 ml of SOB medium/20 mM MgSO4 with the same antibiotics. This culture was grown to an OD600~0.4 when it was harvested and prepared for electroporation as described above. The plasmid pCDF-DUET (Novagen) was cut with restriction enzymes EcoR1 and Hpa1 and product was run on a 1% agarose gel. The piece containing the streptomycin resistance gene was excised from the gel, gel extracted using the QIAquick Gel Extraction Kit (Qiagen) and used as a template for PCR. Primers (TruEpn-StrepResis-F and StrepResis-TruF2-R, Table 3) were designed to have ~43 nucleotides (underlined in Table 3) identical to the sequence flanking the truF1 gene. A PCR experiment was run with the components and conditions as described above except for an extension time of 1 min and a gradient annealing temperature from 55° C. to 65° C.

The PCR product (~1.2 kb) from 240 μl reaction was PCR purified using the QIAquick Gel Extraction Kit (Qiagen) and concentrated then electroporated into the strain BW25113/pIJ790/TOPO-E1. Transformants were selected on LB plates containing kanamycin, ampicillin, chloramphenicol and streptomycin in the concentrations 25, 25, 12.5 and 12.5 μg/ml. The correct transformants were grown in liquid media and the plasmids were purified using the QIAprep Spin Miniprep Kit (QIAGEN) to yield a mixture of the original plasmid (TOPO-E1) and the recombinant plasmid (TOPO-E1-Strep-ΔF1) (FIG. 7). The mixture was then electroporated into the Top10 E. coli strain (Invitrogen) and transformants were screened for recombinants by restriction digest.

Expression of the truF1 knock out vector. Strain Top10/TOPO-E1-Strep-ΔF1 was grown overnight in 50 ml of LB with the appropriate antibiotics then transferred to 10 L of LB with the same antibiotics. Fermentation was allowed to go for ~36 hours at 30° C. with stirring at 500 rpm using a BIOFLO 110 fermentor. Cells were pelleted and broth was extracted with HP20 (SUPELCO) as described above. After washing with water (1.5 L), the organics were eluted with 100% methanol (1 L). Following rotary evaporation of the methanol fraction, the residue was dissolved in water (250 ml) and extracted three times with equal amounts of ethyl acetate. The ethyl acetate fraction was dried, dissolved in a 1:1 water:acetonitrile mixture and used directly for HPLC-LRESIMS analysis for the presence of any cyclic peptides.

Genetic engineering of truE2 pathway using homologous recombination in yeast. The plasmid TOPO-E1 harboring the full truE1 cluster and the plasmid pRS316 were used to form the plasmid TOPO-E1-S316 through homologous recombination in yeast (FIG. S12). The plasmid pRS316 was first digested using BglI to give a 3 kb piece which was then gel extracted using the QIAquick Gel Extraction Kit (Qiagen). TOPO-E1 was linearised by an Nco1 digestion. These two pieces were then transformed into the yeast strain BY4741 (Research Genetics) crossing over the F1 origin of replication and the ampicillin resistance gene. The resulting vector was rescued from the yeast cells into E. coli Top 10 strain (Invitrogen) and validated by restriction digests. Yeast transformation and plasmid rescue were performed following standard procedures. Primers (PatEf-NoRes and pat(G9939)R, Table 3) were used to amplify a 4.2 kb piece from DNA isolated from sample 06-027. This piece was identical, except that it contained truE2 which encodes for patellin 6 and trunkamide rather than truE1 encoding patellins 3 and 2. This piece was used to cross over the plasmid TOPO-E1-S316 by homologous recombination in yeast as described above. The resulting vector TOPO-E1-TK-5316 was rescued and validated by selected sequencing reactions.

Heterologous expression of trunkamide from the engineered vector. The plasmid TOPO-E1-TK-S316 was transformed into the expression E. coli strain (Top10, Invitrogen). A 10 L fermentation experiment was performed as described above. Extraction and analysis of produced compounds followed methods described above. A peak with a mass corresponding to trunkamide was observed at the same retention time as the standard trunkamide isolated from the ascidian 06-027. Moreover, the sample was analyzed by HR-LCES-IMS using a Micromass Q-TOF mass spectrometer with a LockSpray running concurrently to ensure higher mass accuracy. The recombinant trunkamide mass was within 2 ppm error of the reported molecular formula 6.

G. Sequences

SEQ ID NO: 1
GLEASN¹AYDGVEPSN²AYDGE
(where N¹ or N² can be any length)

SEQ ID NO: 2
GLEASN¹AYDGVEPS
(where N¹ can be any length)

SEQ ID NO: 3
AYDGVEPSN²AYDGE
(where N² can be any length)

SEQ ID NO: 4
PatC and ulithiacyclamide
GLEASVTACITFCAYDGVEPSCTLCCTLCAYDGE

SEQ ID NO: 5
PatC and eptidenmamide
GLEASVTACITFCAYDGVEPSQGGRGDWPAYDGE

SEQ ID NO: 6
PatA and PatC
GLEASVTACITFCAYDGVEPSITVCISVCAYDGE

G. Sequences

SEQ ID NO: 7
Full-length Trichodesmium
MGKKNIQPNSSQPVFRSLVARPALEELREENLTEGNQGHGPLANGPGP
SGDGLHPRLCSCSYDGDDE

SEQ ID NO: 8
Abbreviated Trichodesmium
GPGPSGDGLHPRLCSCSYDGDDE

SEQ ID NO: 9
Trichodesmium Recognition Sequence
GPGPSNSYDGDDE

SEQ ID NO: 10
GLEAS

SEQ ID NO: 11
AYDGVEPS

SEQ ID NO: 12
AYDGE

SEQ ID NO: 13
GPGPS

SEQ ID NO: 14
SYDGDDE

SEQ ID NO: 15
5'GCATCACTTTTTGCGCTTATGATGGTGTGGAGCCATCTCAGGGCG
GACGCGGTGACTGGCCTGCTTACGATGGTGAATAA;

SEQ ID NO: 16
5'TTATTCACCATCGTAAGCAGGCCAGTCACCGCGTCCGCCCTGAGA
TGGCTCCACACCATCATAAGCGCAAAAAGTGATGC.

SEQ ID NO: 17
GPGPS

SEQ ID NO: 18
SYDGD

SEQ ID NO: 19
GDGLHPRLCSC

SEQ ID NO: 20
CGTGAAAATTGCTCTTTGAATAAAGG

SEQ ID NO: 21
atcatgaatagagatattttgcgaac

SEQ ID NO: 22
gaatcatgagacttccgctactgtc

SEQ ID NO: 23
aaacatatgatggtcactaacaaccc

SEQ ID NO: 24
ttcatgaacccaaccgcgctccaaattaag

SEQ ID NO: 25
ccaaccaacatatgaacaagaagaacattctacccc

SEQ ID NO: 26
aacatatggacttaaattgacaggcttc

SEQ ID NO: 27
ccatatgatcacgatagactacccttc

SEQ ID NO: 28
tcggccgttccttagtaagaagaagaccaag

SEQ ID NO: 29
aaatgcggccgcttaatcagaataagcgtcccatac

SEQ ID NO: 30
aaaggtaccgaaagaagtagccttagagttaag

SEQ ID NO: 31
gccgcggccgcaaacttgaaaatgcttaaaacg

SEQ ID NO: 32
ttcttattggtacccttattcaccatc

SEQ ID NO: 33
atgactaggtacctgagtcaatgcaaatg

SEQ ID NO: 34
cggtaccccaataactactttgagacggtg

SEQ ID NO: 35
GXXXS

SEQ ID NO: 36
XYDG

SEQ ID NO: 37
ACGGCAAAGGGAGTTTAAACGG

SEQ ID NO: 38
CGCAGCTACGAGCAAAACATTG

SEQ ID NO: 39
CCACAGTTGAGGCCAGCAC

SEQ ID NO: 40
G(L/V)E(A/P)S

SEQ ID NO: 41
AYDG(E/V)

SEQ ID NO: 42
GAEPR

SEQ ID NO: 43
(PatE2)
MNKKN(X)$_{31}$GLEASVTACITFCAYDGVEPSCTLCCTLCAYDGE

SEQ ID NO: 44
(PatEdm)
MNKKN(X)$_{31}$GLEASVTACITFCAYDGVEPSQGGRGDWPAYDGE

SEQ ID NO: 45
(PatE)
MNKKINILPQQGQPVIRTAGQLSSQLAELSEEALGDAGLEASVTACIT
FCAYDGVEPSITVCISVCAYDGE

SEQ ID NO: 46
(PatEBS)
MNKKINILPQQGQPVIRTAGQLSSQLAELSEEALGDAGLEASVTACIT
FCAYDGVEPSQGGRGDWPAYDGE

SEQ ID NO: 47
MNKKINILPQQGQPVIRTAGQLSSQLAELSEEALGDAGLEASVTACIT
FCAYDGVEQSQGGRGDWPAYDGE

SEQ ID NO: 48
(PatEBS2)
MNKKINILPQQGQPVIRTAGQLSSQLAELSEEALGDAGLEASVTACIT
FCAYDGVEQSQGGRGDWPAYDGE

SEQ ID NO: 49
GVDASTLPVPTLCSYDGVDASTVPTLCSYDD

SEQ ID NO: 50
GVDASN$^1$SYDGVDASN$^2$SYDD
(where N$^1$ or N$^2$ can be any length)

SEQ ID NO: 51
GVDASTFPVPTVCSYDGVDASTSPLAPLCSYDD

SEQ ID NO: 52
GVDASN1SYDGVDAS
(where N$^1$ can be any length)

G. Sequences

SEQ ID NO: 53
SYDGVDASN²SYDD
(where N² can be any length)

(TruE1)
SEQ ID NO: 54
MNKKINILPQLGQPVIRLTAGQLSSQLAELSEEALGGVDASTLPVPTL
CSYDGVDASTVPTLCSYDD (TruE2)
SEQ ID NO: 55
MNKKINILPQLGQPVIRLTAGQLSSQLAELSEEALGGVDASTFPVPTV
CSYDGVDASTSIAPFCSYDD (TruE3)
SEQ ID NO: 56
MNKKNILPQLGQPVIRLTAGQLSSQLAELSEEALGGVDASTSIAPFCS
YDGVDASTSIAPFCSYDGVDASTSIAPFCSYDD

SEQ ID NO: 57
MNKKNILPQLGQPVIRLTAGQLSSQLAELSEEALGGVDASN¹SYDGVD
ASN²SYDD

SEQ ID NO: 58
MNKKNILPQLGQPVIRLTAGQLSSQLAELSEEALGGVDASN¹SYDGVD
ASN¹SYDGVDASN³SYDD

SEQ ID NO: 59
GYDAS

SEQ ID NO: 60
SYDGVDAS

SEQ ID NO: 61
SYDD

REFERENCES

Davidson, B. S. Chem. Rev. 93, 1771-1791 (1993).
Long, P. F., Dunlap, W. C., Battershill, C. N. & Jaspars, M. ChemBioChem 6, 1760-1765 (2005).
Ireland, C. M., Durso, A. R., Newman, R. A. & Hacker, M. P. J. Org. Chem. 47, 1807-1811 (1982).
Degnan, B. M. et al. J. Med. Chem. 32, 1349-1354 (1989).
Sudek, S., Haygood, M. G., Youssef, D. T. & Schmidt, E. W. Appl. Environ. Microbiol. 72, 4382-4387 (2006).
Li, Y.-M., Milne, J. C., Madison, L. L., Kolter, R. & Walsh, C. T. Science 274, 1188-1193 (1996).
Milne, B. F., Long, P. F., Starcevic, A., Hranueli, D. & Jaspars, M. Org. Biomol. Chem. 4, 631-638 (2006).
Tan, L. T. Phytochemistry 68, 954-979 (2007).
Ziemert, N. et al. Appl. Environ. Microbiol. 74, 1791-1797 (2008).
Yokobori, Kurabayashi, A., Neilan, B. A., Maruyama, T. & Hirose, E. Multiple origins of the ascidian-Prochloron symbiosis: molecular phylogeny of photosymbiotic and non-symbiotic colonial ascidians inferred from 18S rDNA sequences. Mol. Phylogenet. Evol. 40, 8-19 (2006).
Schmidt, E. W. et al. Patellamide A and C biosynthesis by a microcin-like pathway in *Prochloron didemni*, the cyanobacterial symbiont of *Lissoclinum patella*. Proc. Nat. Acad. Sci. USA 102, 7315-7320 (2005).
Donia, M. S. et al. Natural combinatorial peptide libraries in cyanobacterial symbionts of marine ascidians. Nat. Chem. Biol. 2, 729-735 (2006).
Banker, R. & Carmeli, S. Tenuecyclamides A-D, cyclic hexapeptides from the cyanobacterium *Nostoc spongiaeforme* var. *tenue*. J. Nat. Prod. 61, 1248-1251 (1998).
Zabriskie, T. M., Foster, M. P., Stout, T. J., Clardy, J. & Ireland, C. M. Studies on the solution- and solid-state structure of patellin 2. J. Am. Chem. Soc. 112, 8080-8084 (1990).
Carroll, A. R. et al. Patellins 1-6 and trunkamide A: novel cyclic hexa-, hepta- and octa-peptides from colonial ascidians, *Lissoclinum* sp. Aust. J. Chem. 49, 659-667 (1996).
Salvatella, X., Caba, J. M., Albericio, F. & Giralt, E. Solution structure of the antitumor candidate trunkamide A by 2D NMR and restrained simulated annealing methods. J. Org. Chem. 68, 211-215 (2003).
Sikorski, R. S. & Hieter, P. A system of shuttle vectors and yeast host strains designed for efficient manipulation of DNA in *Saccharomyces cerevisiae*. Genetics 122, 19-27 (1989).
Kunes, S., Ma, H., Overbye, K., Fox, M. S. & Botstein, D. Fine structure recombinational analysis of cloned genes using yeast transformation. Genetics 115, 73-81 (1987).

What is claimed is:

1. An isolated polypeptide comprising TruE1, TruE2, or TruE3, or a fragment thereof of at least 10 residues in length.

2. The isolated polypeptide of claim 1, wherein the sequence consists of SEQ ID NO: 54, 55, or 56 or a fragment thereof of at least 10 residues in length.

3. An isolated polypeptide of 10 to 400 amino acids comprising SEQ ID NO: 54, 55, or 56, or a fragment thereof of at least 10 residues in length.

4. An isolated polypeptide of 10 to 400 amino acids comprising an amino acid sequence having at least 80% sequence homology to SEQ ID NO: 54, 55, or 56 or a fragment thereof of at least 10 residues in length.

5. An isolated polypeptide consisting essentially of an amino acid sequence having at least 80% sequence homology to SEQ ID NO: 54, 55, or 56, or an amino acid sequence having at least 90% sequence homology to a fragment of SEQ ID NO: 54, 55, or 56 of at least 10 residues in length.

6. An isolated nucleic acid encoding the polypeptide of any of claims 1-5.

7. A vector comprising the isolated nucleic acid of claim 6.

* * * * *

UNITED STATES PATENT AND TRADEMARK OFFICE
CERTIFICATE OF CORRECTION

PATENT NO. : 8,470,965 B2
APPLICATION NO. : 12/426652
DATED : June 25, 2013
INVENTOR(S) : Eric W. Schmidt et al.

It is certified that error appears in the above-identified patent and that said Letters Patent is hereby corrected as shown below:

IN THE SPECIFICATION

In column 1, lines 17-21, replace "This invention was made with government support under federal grant NIH R01 GM07142501A1 awarded by the NIH and NSF EF-0412226 subcontract from the Institute for Genomic Research. The Government has certain rights to this invention." with -- This invention was made with government support under Grant number R01 GM071425 awarded by National Institutes of Health and Grant number EF-0412226 awarded by National Science Foundation. The government has certain rights in this invention. --

Signed and Sealed this
Twenty-fifth Day of August, 2015

Michelle K. Lee
*Director of the United States Patent and Trademark Office*

SEQUENCE LISTING

```
<160> NUMBER OF SEQ ID NOS: 61

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 1

Gly Leu Glu Ala Ser Asn Ala Tyr Asp Gly Val Glu Pro Ser Asn Ala
1               5                   10                  15

Tyr Asp Gly Glu
            20

<210> SEQ ID NO 2
<211> LENGTH: 14
<212> TYPE: PRT
<213> ORGANISM: Artificial Sequence
```

```
<220> FEATURE:
<223> OTHER INFORMATION: Description of Artificial Sequence:
      note=synthetic construct

<400> SEQUENCE: 2

Gly Leu Glu Ala Ser Asn Ala Tyr Asp Gly Val Glu Pro Ser
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 3

Ala Tyr Asp Gly Val Glu Pro Ser Asn Ala Tyr Asp Gly Glu
1               5                   10

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 4

Gly Leu Glu Ala Ser Val Thr Ala Cys Ile Thr Phe Cys Ala Tyr Asp
1               5                   10                  15

Gly Val Glu Pro Ser Cys Thr Leu Cys Cys Thr Leu Cys Ala Tyr Asp
            20                  25                  30

Gly Glu

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 5

Gly Leu Glu Ala Ser Val Thr Ala Cys Ile Thr Phe Cys Ala Tyr Asp
1               5                   10                  15

Gly Val Glu Pro Ser Gln Gly Gly Arg Gly Asp Trp Pro Ala Tyr Asp
            20                  25                  30

Gly Glu

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 6

Gly Leu Glu Ala Ser Val Thr Ala Cys Ile Thr Phe Cys Ala Tyr Asp
1               5                   10                  15

Gly Val Glu Pro Ser Ile Thr Val Cys Ile Ser Val Cys Ala Tyr Asp
            20                  25                  30

Gly Glu
```

```
<210> SEQ ID NO 7
<211> LENGTH: 67
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 7

Met Gly Lys Lys Asn Ile Gln Pro Asn Ser Ser Gln Pro Val Phe Arg
 1               5                  10                  15

Ser Leu Val Ala Arg Pro Ala Leu Glu Glu Leu Arg Glu Glu Asn Leu
                20                  25                  30

Thr Glu Gly Asn Gln Gly His Gly Pro Leu Ala Asn Gly Pro Gly Pro
            35                  40                  45

Ser Gly Asp Gly Leu His Pro Arg Leu Cys Ser Cys Ser Tyr Asp Gly
        50                  55                  60

Asp Asp Glu
65

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 8

Gly Pro Gly Pro Ser Gly Asp Gly Leu His Pro Arg Leu Cys Ser Cys
 1               5                  10                  15

Ser Tyr Asp Gly Asp Asp Glu
            20

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 9

Gly Pro Gly Pro Ser Asn Ser Tyr Asp Gly Asp Asp Glu
 1               5                  10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 10

Gly Leu Glu Ala Ser
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:
      note=synthetic construct
```

-continued

```
<400> SEQUENCE: 11

Ala Tyr Asp Gly Val Glu Pro Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 12

Ala Tyr Asp Gly Glu
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 13

Gly Pro Gly Pro Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 14

Ser Tyr Asp Gly Asp Asp Glu
1               5

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 15
gcatcacttt ttgcgcttat gatggtgtgg agccatctca gggcggacgc ggtgactggc      60
ctgcttacga tggtgaataa                                                  80

<210> SEQ ID NO 16
<211> LENGTH: 80
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 16
ttattcacca tcgtaagcag gccagtcacc gcgtccgccc tgagatggct ccacaccatc      60
ataagcgcaa aaagtgatgc                                                  80
```

```
<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 17

Gly Pro Gly Pro Ser
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 18

Ser Tyr Asp Gly Asp
 1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 19

Gly Asp Gly Leu His Pro Arg Leu Cys Ser Cys
 1               5                  10

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 20
cgtgaaaatt gctctttgaa taaagg                                      26

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 21
atcatgaata gagatatttt gcgaac                                      26

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 22
gaatcatgag acttccgcta ctgtc                                       25
```

```
<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 23
aaacatatga tggtcactaa caaccc                                         26

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 24
ttcatgaacc caaccgcgct ccaaattaag                                     30

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 25
ccaaccaaca tatgaacaag aagaacattc taccccc                             36

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 26
aacatatgga cttaaattga caggcttc                                       28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 27
ccatatgatc acgatagact acccttc                                        28

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 28
tcggccgttc cttagtaaga agaagaccaa g                                   31
```

```
<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 29
aaatgcggcc gcttaatcag aataagcgtc ccatac                              36

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 30
aaaggtaccg aaagaagtag ccttagagtt aag                                 33

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 31
gccgcggccg caaacttgaa aatgcttaaa acg                                 33

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 32
ttcttattgg taccttatt caccatc                                         27

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 33
atgactaggt acctgagtca atgcaaatg                                      29

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 34 cggtaccca ataactactt tgagacggtg                                      30
```

```
<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:
      note=synthetic construct
<220> FEATURE:
<221> NAME/KEY: VARIANT
<222> LOCATION: 2-4
<223> OTHER INFORMATION: Xaa=any amino acid
<220> FEATURE:
<221> NAME/KEY: VARIANT
<222> LOCATION: 2
<223> OTHER INFORMATION: Xaa=any amino acid
<220> FEATURE:
<221> NAME/KEY: VARIANT
<222> LOCATION: 3
<223> OTHER INFORMATION: Xaa=any amino acid
<220> FEATURE:
<221> NAME/KEY: VARIANT
<222> LOCATION: 4
<223> OTHER INFORMATION: Xaa=any amino acid

<400> SEQUENCE: 35

Gly Xaa Xaa Xaa Ser
 1               5

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence:
      note=synthetic construct
<220> FEATURE:
<221> NAME/KEY: VARIANT
<222> LOCATION: 1
<223> OTHER INFORMATION: Xaa=any amino acid

<400> SEQUENCE: 36

Xaa Tyr Asp Gly
 1

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 37
acggcaaagg gagtttaaac gg                                              22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence:
      note=synthetic construct

<400> SEQUENCE: 38
cgcagctacg agcaaaacat tg                                              22

<210> SEQ ID NO 39
<211> LENGTH: 19
<212> TYPE: DNA
<213> ORGANISM: Artificial Sequence
```

```
<220> FEATURE:
<223> OTHER INFORMATION: Description of Artificial Sequence:
      note=synthetic construct

<400> SEQUENCE: 39
ccacagttga ggccagcac                                                    19

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 40

Gly Leu Val Glu Ala Pro Ser
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 41

Ala Tyr Asp Gly Glu Val
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 42

Gly Ala Glu Pro Arg
1               5

<210> SEQ ID NO 43
<211> LENGTH: 40
<212> TYPE: PRT
<213> ORGANISM: Artificial Sequence
<220> FEATURE:
<223> OTHER INFORMATION: Description of Artificial Sequence:
      note=synthetic construct
<220> FEATURE:
<221> NAME/KEY: VARIANT
<222> LOCATION: 6
<223> OTHER INFORMATION: Xaa=any amino acid

<400> SEQUENCE: 43

Met Asn Lys Lys Asn Xaa Gly Leu Glu Ala Ser Val Thr Ala Cys Ile
1               5                   10                  15

Thr Phe Cys Ala Tyr Asp Gly Val Glu Pro Ser Cys Thr Leu Cys Cys
            20                  25                  30

Thr Leu Cys Ala Tyr Asp Gly Glu
        35                  40

<210> SEQ ID NO 44
<211> LENGTH: 40
<212> TYPE: PRT
<213> ORGANISM: Artificial Sequence
```

```
<220> FEATURE:
<223> OTHER INFORMATION: Description of Artificial Sequence:
      note=synthetic construct
<220> FEATURE:
<221> NAME/KEY: VARIANT
<222> LOCATION: 6
<223> OTHER INFORMATION: Xaa=any amino acid

<400> SEQUENCE: 44

Met Asn Lys Lys Asn Xaa Gly Leu Glu Ala Ser Val Thr Ala Cys Ile
1               5                   10                  15

Thr Phe Cys Ala Tyr Asp Gly Val Glu Pro Ser Gln Gly Gly Arg Gly
            20                  25                  30

Asp Trp Pro Ala Tyr Asp Gly Glu
        35                  40

<210> SEQ ID NO 45
<211> LENGTH: 70
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 45

Met Asn Lys Lys Asn Ile Leu Pro Gln Gln Gly Gln Pro Val Ile Arg
1               5                   10                  15

Thr Ala Gly Gln Leu Ser Ser Gln Leu Ala Glu Leu Ser Glu Glu Ala
            20                  25                  30

Leu Gly Asp Ala Gly Leu Glu Ala Ser Val Thr Ala Cys Ile Thr Phe
        35                  40                  45

Cys Ala Tyr Asp Gly Val Glu Pro Ser Ile Thr Val Cys Ile Ser Val
    50                  55                  60

Cys Ala Tyr Asp Gly Glu
65                  70

<210> SEQ ID NO 46
<211> LENGTH: 70
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 46

Met Asn Lys Lys Asn Ile Leu Pro Gln Gln Gly Gln Pro Val Ile Arg
1               5                   10                  15

Thr Ala Gly Gln Leu Ser Ser Gln Leu Ala Glu Leu Ser Glu Glu Ala
            20                  25                  30

Leu Gly Asp Ala Gly Leu Glu Ala Ser Val Thr Ala Cys Ile Thr Phe
        35                  40                  45

Cys Ala Tyr Asp Gly Val Glu Pro Ser Gln Gly Gly Arg Gly Asp Trp
    50                  55                  60

Pro Ala Tyr Asp Gly Glu
65                  70

<210> SEQ ID NO 47
<211> LENGTH: 70
<212> TYPE: PRT
<213> ORGANISM: Artificial Sequence
<220> FEATURE:
<223> OTHER INFORMATION: Description of Artificial Sequence:
      note=synthetic construct
```

<400> SEQUENCE: 47

Met Asn Lys Lys Asn Ile Leu Pro Gln Gln Gly Gln Pro Val Ile Arg
1               5                   10                  15

Thr Ala Gly Gln Leu Ser Ser Gln Leu Ala Glu Leu Ser Glu Glu Ala
                20                  25                  30

Leu Gly Asp Ala Gly Leu Glu Ala Ser Val Thr Ala Cys Ile Thr Phe
            35                  40                  45

Cys Ala Tyr Asp Gly Val Glu Gln Ser Gln Gly Gly Arg Gly Asp Trp
50                  55                  60

Pro Ala Tyr Asp Gly Glu
65                  70

<210> SEQ ID NO 48
<211> LENGTH: 70
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 48

Met Asn Lys Lys Asn Ile Leu Pro Gln Gln Gly Gln Pro Val Ile Arg
1               5                   10                  15

Thr Ala Gly Gln Leu Ser Ser Gln Leu Ala Glu Leu Ser Glu Glu Ala
                20                  25                  30

Leu Gly Asp Ala Gly Leu Glu Ala Ser Val Thr Ala Cys Ile Thr Phe
            35                  40                  45

Cys Ala Tyr Asp Gly Val Glu Gln Ser Gln Gly Gly Arg Gly Asp Trp
50                  55                  60

Pro Ala Tyr Asp Gly Glu
65                  70

<210> SEQ ID NO 49
<211> LENGTH: 31
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 49

Gly Val Asp Ala Ser Thr Leu Pro Val Pro Thr Leu Cys Ser Tyr Asp
1               5                   10                  15

Gly Val Asp Ala Ser Thr Val Pro Thr Leu Cys Ser Tyr Asp Asp
                20                  25                  30

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 50

Gly Val Asp Ala Ser Asn Ser Tyr Asp Gly Val Asp Ala Ser Asn Ser
1               5                   10                  15

Tyr Asp Asp

```
<210> SEQ ID NO 51
<211> LENGTH: 33
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 51
```

Gly Val Asp Ala Ser Thr Phe Pro Val Pro Thr Val Cys Ser Tyr Asp
 1               5                  10                  15

Gly Val Asp Ala Ser Thr Ser Pro Leu Ala Pro Leu Cys Ser Tyr Asp
                20                  25                  30

Asp

```
<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 52
```

Gly Val Asp Ala Ser Asn Ser Tyr Asp Gly Val Asp Ala Ser
 1               5                  10

```
<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 53
```

Ser Tyr Asp Gly Val Asp Ala Ser Asn Ser Tyr Asp Asp
 1               5                  10

```
<210> SEQ ID NO 54
<211> LENGTH: 66
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 54
```

Met Asn Lys Lys Asn Ile Leu Pro Gln Leu Gly Gln Pro Val Ile Arg
 1               5                  10                  15

Leu Thr Ala Gly Gln Leu Ser Ser Gln Leu Ala Glu Leu Ser Glu Glu
                20                  25                  30

Ala Leu Gly Gly Val Asp Ala Ser Thr Leu Pro Val Pro Thr Leu Cys
            35                  40                  45

Ser Tyr Asp Gly Val Asp Ala Ser Thr Val Pro Thr Leu Cys Ser Tyr
        50                  55                  60

Asp Asp
65

```
<210> SEQ ID NO 55
<211> LENGTH: 67
<212> TYPE: PRT
<213> ORGANISM: Artificial Sequence
<220> FEATURE:
<223> OTHER INFORMATION: Description of Artificial Sequence:
      note=synthetic construct
```

<400> SEQUENCE: 55

```
Met Asn Lys Lys Asn Ile Leu Pro Gln Leu Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Gly Val Asp Ala Ser Thr Phe Pro Val Pro Thr Val Cys
        35                  40                  45

Ser Tyr Asp Gly Val Asp Ala Ser Thr Ser Ile Ala Pro Phe Cys Ser
    50                  55                  60

Tyr Asp Asp
65
```

<210> SEQ ID NO 56
<211> LENGTH: 81
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 56

```
Met Asn Lys Lys Asn Ile Leu Pro Gln Leu Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Gly Val Asp Ala Ser Thr Ser Ile Ala Pro Phe Cys Ser
        35                  40                  45

Tyr Asp Gly Val Asp Ala Ser Thr Ser Ile Ala Pro Phe Cys Ser Tyr
    50                  55                  60

Asp Gly Val Asp Ala Ser Thr Ser Ile Ala Pro Phe Cys Ser Tyr Asp
65                  70                  75                  80

Asp
```

<210> SEQ ID NO 57
<211> LENGTH: 54
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 57

```
Met Asn Lys Lys Asn Ile Leu Pro Gln Leu Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Gly Val Asp Ala Ser Asn Ser Tyr Asp Gly Val Asp Ala
        35                  40                  45

Ser Asn Ser Tyr Asp Asp
    50
```

<210> SEQ ID NO 58
<211> LENGTH: 63
<212> TYPE: PRT
<213> ORGANISM: Artificial Sequence
<220> FEATURE:
<223> OTHER INFORMATION: Description of Artificial Sequence:
      note=synthetic construct

```
<400> SEQUENCE: 58

Met Asn Lys Lys Asn Ile Leu Pro Gln Leu Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Gly Val Asp Ala Ser Asn Ser Tyr Asp Gly Val Asp Ala
        35                  40                  45

Ser Asn Ser Tyr Asp Gly Val Asp Ala Ser Asn Ser Tyr Asp Asp
    50                  55                  60

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 59

Gly Val Asp Ala Ser
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 60

Ser Tyr Asp Gly Val Asp Ala Ser
1               5

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence:
      note=synthetic construct

<400> SEQUENCE: 61

Ser Tyr Asp Asp
1
```